US007960536B2

(12) United States Patent
Schwartz et al.

(10) Patent No.: US 7,960,536 B2
(45) Date of Patent: Jun. 14, 2011

(54) SYNTHETIC CELL-OR TISSUE-SPECIFIC TRANSCRIPTIONAL REGULATORY REGIONS

(75) Inventors: Robert J. Schwartz, Houston, TX (US); Eric M. Eastman, Highland, MD (US); Xuyang Li, Houston, TX (US); Jeff Nordstrom, College Station, TX (US)

(73) Assignee: Genetronics, Inc., San Diego, CA (US)

( * ) Notice: Subject to any disclaimer, the term of this patent is extended or adjusted under 35 U.S.C. 154(b) by 1508 days.

(21) Appl. No.: 11/080,827

(22) Filed: Mar. 14, 2005

(65) Prior Publication Data
US 2005/0164282 A1    Jul. 28, 2005

Related U.S. Application Data

(60) Division of application No. 10/137,216, filed on May 1, 2002, now abandoned, which is a continuation of application No. 09/115,407, filed on Jul. 14, 1998, now Pat. No. 6,410,228.

(60) Provisional application No. 60/052,403, filed on Jul. 14, 1997.

(51) Int. Cl.
*C12N 15/63* (2006.01)
(52) U.S. Cl. .................................. 536/24.1; 435/320.1
(58) Field of Classification Search .................. None
See application file for complete search history.

(56) References Cited

U.S. PATENT DOCUMENTS

| | | | |
|---|---|---|---|
| 4,822,736 | A | 4/1989 | Kellems et al. |
| 5,118,604 | A | 6/1992 | Weissman et al. |
| 5,306,619 | A | 4/1994 | Edwards et al. |
| 5,374,544 | A | 12/1994 | Schwartz et al. |
| 5,403,712 | A | 4/1995 | Crabtree et al. |
| 5,627,058 | A | 5/1997 | Ruley et al. |

FOREIGN PATENT DOCUMENTS

| | | |
|---|---|---|
| WO | 93/10245 | 5/1993 |
| WO | 93/20218 | 10/1993 |
| WO | 93/21347 | 10/1993 |
| WO | 94/01129 | 1/1994 |
| WO | 94/14971 | 7/1994 |
| WO | 97/20931 | 6/1997 |
| WO | 98/07846 | 2/1998 |
| WO | 98/36097 | 8/1998 |

OTHER PUBLICATIONS

Feo et al., Mol. Cell. Biol., vol. 15, 1995, pp. 5991-6002.*
Mader et al., PNAS, vol. 90, 1993, pp. 5603-5607.*
Taylor et al., Development vol. 106,pp. 67-78 (1989).*
MacLellan et al., The Journal of Biochemistry, vol. 269, No. 24, pp. 16754-16760 (1994).*
Baillie et al., "Transient Transfection of Chick-Embryo Hepatocytes," Journal of Nutritional Biochemistry, vol. 4, No. 7, (1993) pp. 431-439.

Blackwell et al., "Differences and Similarities in DNA-Binding Preferences of MyoD and E2A Protein Complexes Revealed by Binding Site Selection," Science, vol. 250, (1990) pp. 1104-1110.
Blackwell et al., "Sequence-Specific DNA Binding by the c-Myc Protein," Science, vol. 250, (1990) pp. 1149-1151.
Brinster et al., "Factors Affecting the Efficiency of Introducing Foreign DNA into Mice by Microinjecting Eggs," Proc. Natl. Acad. Sci. USA, vol. 82, (1985) pp. 4438-4442.
Chow et al., "A Combination of Closely Associated Positive and Negative CIS-Acting Promoter Elements Regulates Transcription of the Skeletal Alpha-Actin Gene," Molecular and Cellular Biol., vol. 10, No. 2, (1990) pp. 528-538.
Cornwell et al., "Description of the Leukocyte Function-Associated Antigen 1 (LFA-1 or CD11A) Promoter," PNAS USA, vol. 90, No. 9. (1993) pp. 4221-4225.
Dent et al., "The DNA Mobility Shift Assay," Transcription Factors: A Practical Approach, D.S. Latchman (ed.) IRL Press, Oxford,(1993) pp. 1-26.
Harrison et al., "Functional Identification of Genes Up- and Down-Regulated by Glucocorticoids in ATT-20 Pituitary Cells Using an Enhancer Trap," Endocrinology, vol. 137 No. 7, (1996) pp. 2758-2765.
Hobson et al., "Use of DNA-Protein Interaction to Isolate Specific Genomic DNA Sequences," Analytical Biochemistry, vol. 193, No. 2, (1991) pp. 220-224.
Huang et al., "Differences Between MyoD DNA Binding and Activation Site Requirements Revealed by Functional Random Sequence Selection," Mol. Cell Biol, vol. 16, (1996) pp. 3893-3900.
Kaufman et al., "Selection and Amplification of Heterologous Genes Encoding Adenosine Deaminase in Mammalian Cells," PNAS, vol. 83, (1986) pp. 3136-3140.
Kaufman, "Selection and Coamplification of Heterologous Genes in Mammalian Cells," Meth. Enzymol., vol. 185, (1990) pp. 537-566.
Kellems, "Adenosine Deaminase: A Dominant Amplifiable Genetic Marker," Gene Amplification in Mammalian Cells, Marcel Dekker, Inc., New York, (1992) pp. 207-221.
Kellems, "Gene Amplification in Mammalian Cells: Strategies for Protein Production," Current Opinion in Biotechnology, vol. 2, (1991) pp. 723-729.
Kellems, "Gene Amplification Strategies for Protein Production in Mammalian Cells," Methods in Molecular Genetics, vol. 5, (1994) pp. 143-155. Kellems et al., "Adenosine Deaminase: a Dominant Amplifiable Genetic Marker for Use in Mammalian Cells," Genetics and Molecular Biology of Industrial Microorganisms, Hershberger et al., (ed.) American Society for Microbiology, Washington, (1989) pp. 215-225.
Nallur et al., "Multiplex Selection Technique (MuST): An Approach to Clone Transcription Factor Binding Sites," PNAS, vol. 93, (1996) pp. 1184-1189.
Oliphant et al., "Defining the Sequence Specificity of DNA-Binding Sites from Random-Sequence Oligonucleotides: Analysis of Yeast GCN4 Protein," Mol. Cellular Biology, vol. 9, No. 7, (1989) pp. 2944-2949.
Pierrou et al., Selection of High-Affinity Binding Sites for Sequence-Specific, DNA Binding Proteins From Random Sequence Oligonucleotides. Anal. Biochem., vol. 229, (1995) pp. 99-105.
Rebatchouk et al., "NOMAD: A Versatile Strategy for In Vitro DNA Manipulation Applied to Promoter Analysis and Vector Designs," PNAS, vol. 93, (1996) pp. 10891-10896.
Scopes et al., Protein Purification, Springer Verlag, NY (1987).

(Continued)

*Primary Examiner* — James S Ketter
(74) *Attorney, Agent, or Firm* — Thomas S. Kim

(57) ABSTRACT

The invention concerns making and evaluating synthetic regulatory regions for controlling gene expression. The invention features a method for identifying transcription factor binding sites and a method for evaluating the regulatory functions of synthetic regulatory regions.

4 Claims, 41 Drawing Sheets

OTHER PUBLICATIONS

Sun et al., "An Inhibitory Domain of E12 Transcription Factor Prevents DNA Binding in E12 Homodomers but Not in E12 Heterodimers," Cell, vol. 64, (1991) pp. 459-470.

Thiesen et al., "Target Detection Assay (TDA): A Versatile Procedure to Determine DNA Binding Sites as Demonstrated on SP1 Protein," Nucleic Acids Research, vol. 18, No. 11, (1990) pp. 3203-3209.

Valdivia et al., "Bacterial Genetics by Flow Cytometry: Rapid Isolation of *Salmonella typhimurium* Acid-Inducible promoters by Differential Fluorescence Induction," Mol. Microbiol., vol. 22, (1996) pp. 367-378.

Yeung et al., "Increased Expression of One of Two Adenosine Deaminase Alleles in a Human Choriocarcinoma Cell Line Following Selection with Adenine Nucleosides," J. Biol. Chem., vol. 258, (1983) pp. 8330-8337.

Yeung et al., "Selective Overproduction of Adenosine Deaminase in Cultured Mouse Cells," J. Biol. Chem., vol. 258, (1983) pp. 8338-8345.

* cited by examiner

C1-28

| | 10 | 20 | 30 | 40 | 50 | 60 |
|---|---|---|---|---|---|---|
| | ATTTTACAAC | AGTACCGGAA | TGCCAAGCTT | GATATCGAAT | TCCTGCAGCC | CGGGGGATCC |
| | 70 | 80 | 90 | 100 | 110 | 120 |
| | ACTAGTTCTA | GAGCTTGGCG | CCTCCCGCTC | CTCCGGGTAG | CTCGTGGGCC | GCCGCCGGCC |
| | 130 | 140 | 150 | 160 | 170 | 180 |
| | CCGGAGCCTT | TTATCGAGGC | GGGCGGGAGC | ACCGCCCGGC | CCCCAGGAAT | GCGGCCCCGG |
| | 190 | 200 | 210 | 220 | 230 | 240 |
| | CCGTCCGCCC | TCGGGAGTTA | TTTTAGANCG | GTGAGGAATG | GTGCCAACAC | CTGCTGCCTG |
| | 250 | 260 | 270 | 280 | 290 | 300 |
| | CCCCGTCGCC | ATATTTGGGT | GTCGTGAGGA | ATGGTGCCGT | CGCCATATTT | CCGTCGCCAT |
| | 310 | 320 | 330 | 340 | 350 | 360 |
| | ATTTGGGTGT | CCACCATTCC | TCACCGCTCT | AAAAATAACT | CCCGGGAGTT | ATTTTAGAG |
| | 370 | 380 | 390 | 400 | 410 | 420 |
| | CGCCGTCGCC | ATATTTGGGT | GTCGTGAGGA | ATGGTGCACC | ATTCCTCACC | GCTCTAAAAA |
| | 430 | 440 | 450 | 460 | 470 | 480 |
| | TAACTCCCCC | AACACCTGCT | GCCTGCCCGC | TCTAAAATAA | CTCCCGACAC | CCAAATATGG |
| | 490 | 500 | 510 | 520 | 530 | 540 |
| | CGACGGCCGC | CACCGGGGTG | GANCTCGGTA | CCTCCCGGGT | TATGTTAACT | CANTTACAGT |
| | 550 | 560 | 570 | 580 | 590 | 600 |
| | ACCATAANAT | .......... | .......... | .......... | .......... | .......... |

Fig. 8

```
C2-27
         10          20          30          40          50          60
ATTTACAAC   TTCGNGAGAN  TGCCAAGCTT  GATATCGAAT  TCCTGCAGCC  CGGGGGATCC
         70          80          90         100         110         120
ACTAGTTCTA  GAGCTTGGCG  CCTCCCGCTC  CTCCGGGTAG  CTCGTGGGCC  GCCGCCGGCC
        130         140         150         160         170         180
CCGGAGCCTT  TTATCGAGGC  GGGCGGGAGC  ACCGCCCGGC  CCCCAGGAAT  GCGGCCCCGG
        190         200         210         220         230         240
CCGTCGCCAT  ATTTGGGTGT  CCCAACACTG  CTGCCTGCCG  ACACCCAAAT  ATGGCGACGG
        250         260         270         280         290         300
GTGAGGAATG  GTGCCAACAC  CTGCTGCCTG  CCGACACCCA  AATATGGCGA  CGGCCGCCAC
        310         320         330         340         350         360
CGCGGGTGGAG CTCGGTACCT  CCCGGGTTAT  GTTAGCTCAG  TTACAGTACC  ATAANATACA
        370         380         390         400         410         420
TTGATGAGTT  TGGACAAACC  ACAACTANAA  TGCAGTGAAA  AAAATGCTTT  ATTTGTGAAA
        430         440         450         460         470         480
TATTGCTTTA  TTTGTAACCA  TTATAAGCTG  CAATAAACAA  GTTAACAACA
        490         500         510         520         530         540
TCATTTTATG  TTTCAAGTTC  AGGGGGANGT  GTGGGAAGTT  TTTTAAAGCA
ACAATTGCAT
        550         560         570         580         590         600
AGTAAAACCT  CCACGTACCT  TAATATTACT  TACTTATCAT  GGTACTTGGG  CTGGGCGTAAT
        610         620         630         640         650         660
...........................................................

Fig. 9A
```

BCM17.CP1
BCM17.CP1

```
1    AATGCCAAGC TTGATATCGA ATTCCTGCAG CCCGGGGGAT CCACTAGTTC TAGAGCTTGG

61   CGCCTCCCGC TCCTCCGGGT AGCTCGTGGG CCGCCGCCGG CCCCGGAGCC TTTTATCGAG

121  GCGGGCGGGA GCACCGCCCG GCCCCCCAGGA ATGCGGGCCCC GGCCGTCGCC ATATTTGGGT
                                                                SRE
181  GTCCCAACAC TGCTGCCTGC CGACACCCAA ATATGGCGAC GGGTGAGGAA TGGTGCCAAC
     MEF-1                        SRE                      TEF-1
241  ACCTGCTGCC TGCGACACC CAAATATGGC GACGGCCGCC ACCGCGGTGG AGCTCGGTAC
     MEF-1
301  CTCCCGGGTT ATGTTAGCTC AGTTACAGTA CCATAAGATA TTATTTGTGA TTTGGACAAA

361  CCACAACTAG AATGCAGTGA AAAAAATGCT TGCAATAAAC AATTTAACAA GCTATTGCTT

421  TATTTGTAA CCATTATAAC TGCAATAAAC AATTTAACAA CAACAATTGC ATTCCATTTT

481  ATTTTTCAAG TTCAAGGGGA
```

Fig. 9B

C5-12
DNASIS
4573-12g.seq

```
              10         20         30         40         50         60
      ATTTTACAAC AGTACGGAAT GCCAAGCTTG ATATCGAATT CCTGCAGCCC GGGGGATCCA
              70         80         90        100        110        120
      CTAGTTCTAG AGCTTGGCGC CTCCCGCTCC TCCGGGTAGC TCGTGGGCCG CCGCCGGCCC
             130        140        150        160        170        180
      CGGAGCCTTT TATCGAGGCG GGCGGGAGCA CCGCCCGGCC CCCAGGAATG CGGCCCCGGC
             190        200        210        220        230        240
      CGAGGGGCGGA CACCCAAATA TGGCGACGGG TGAGGAACCG TCGCCATATT TGGGTGTCCA
             250        260        270        280        290        300
      CCATTCCTCC GCTCTAAAAA TAACTCCCGG GAGTTATTTT TAAAGCGCCA ACACCTGCTG
             310        320        330        340        350        360
      CCTGCCCACC TTCCTCACCG CTCTAAAAAT AACTCCCCAC CATTCCTCAC CCGTCGCCAT
             370        380        390        400        410        420
      ATTTGGGTGT CGTGAGGATG GTGCCGAAGG CGGACGGCCG CCACCGCGGT GGANCTCGGT
             430        440        450        460        470        480
      ACCTCCCGGG TTATGTTANC TCANTTACAN TACCATAANA TACATTGATG AATTTGGACA
             490        500        510        520        530        540
      AACCACAACT ANAATGCATG AAAAAAATGC TTTATTTGTN AAATTTGTNA TGCTATTGCT
             550        560        570        580        590        600
      TTATTTGTTA  ........  ........  ........  ........  ........
```

Fig. 10A

```
DNASIS
4573-16g.seq
           10          20          30          40          50          60
     ATTTTACCAA  CAGTACCGGA  ATGCCAAGCT  TGATATCGAA  TTCCTGCAGC  CCGGGGGATC
           70          80          90         100         110         120
     CACTAGTTCT  AGAGCTTGGC  GCCTCCCGCT  CCTCCGGGTA  GCTCGTGGGC  CGCCGCCGGC
          130         140         150         160         170         180
     CCCGGAGCCT  TTTATCGAGG  CGGGGCGGGAG CACCGCCCGG  CCCCCAGGAA  TGCGGCCCCG
          190         200         210         220         230         240
     GCCGAGGGCG  GACACCAAAT  ATGGGCGACGG  GGCAGGCAGC  AGGTGTTGGG  GCAGGCAGCA
          250         260         270         280         290         300
     GGTGTTGGCC  AACACCTGCT  GCCTGCCGAC  ACCCAAATAT  GGCGACGGGG  CAGGCAGCAG
          310         320         330         340         350         360
     GTGTTGGGGG  AGTTATTTTT  AGAGCGGACA  CCCAAATATG  GCGACGGCCG  CCACCGGGGT
          370         380         390         400         410         420
     GGAGCTCGGT  ACCTCCCGGG  TTATGTTAGC  TCAGTTACAG  TACCATAAGA  TACATTGATG
          430         440         450         460         470         480
     AGTTTGGACA  AACCACAACT  ANAATGCAGT  TGAAAAAAAT  GCTTATTTG  TGAAATTTGT
          490         500         510         520         530         540
     GATGCTATTG  CTTTATTTGT  AACCATTATA  AGCTGCAATA  AACAATTTAA  CAACAACAAT
          550         560         570         580         590         600
     TGCATTCCAT  ..........  ..........  ..........  ..........  ........
```

Fig. 11A

BCM16.CP1
BCM16.CP1

```
  1  GCTTGATATC GAATTCCTGC AGCCCGGGGG CATCCACTAT CTACTAGNGC TTGACNCCTC
 61  CCGCTCCTCC GGGTAGCTCG TGGGCCGCCG CCGGCCCCGG ACCCTATNAT CGAAGCGGGC
121  NGGANCACNG CCCGGCCCCC ACCCAATGCA GTCCCGGCCC GAGGGCNCGA CACCAAATAT
181  GTGTCACAGG GCNGGCACCA GGTGTTGGGG CAAGCNGCAG GTGTTTGCCA ACTCCTGCTG
241  CCTGCCGACA CCCANATATG GCCACNGGGC ACGNAGCACG TGTTNGGGGA GTNATTTTA
301  NACCCNACAC NCANGCCGC CACCGCGGGTN GANCTCGGTA ACTCCCGGGT
361  TATGTTANCT CAATTACAGT ACCATAAATAT NCTTTGATNA ATTTGGACAA ACCACAACTA
421  TAATGCAGTG AAAAAAATGC TTTATTGTG AAATTTGTNA TGCTATTGCT TTTATNTNTT
481  AANCATTANA AGCTCCAATA A
```

*Fig. 11B*

```
DNASIS
4585-1g.seq
         10         20         30         40         50         60
ATTTACAAC  AGTACGGAAT GCCAAGCTTG ATATCGAATT CCTGCAGCCC GGGGGATCCA
         70         80         90        100        110        120
CTAGTTCTAG AGCTTGGCGC CTCCCGCTCC TCCGGGTAGC TCGTGGGCCG CCGCCGGCCC
        130        140        150        160        170        180
CGGAGCCTTT TATCGAGGCG GGCGGGAGCA CCGCCCCGGC CCCAGGAATG CGGCCCCGGC
        190        200        210        220        230        240
CGTCCGCCCT CGGGACACCC AAATATGGCG ACGGGCGCTCT AAAAATAACT CCCCCAACAC
        250        260        270        280        290        300
CTGCTGCCTG CCGACACCCA AATATGGCAA CGGGGCNAGG CAGCAGGTGT TTGGCGCTCT
        310        320        330        340        350        360
AAAAATAACT CCCCCCGAGG GCGGACGGCC CGCCACCGCG GTNGGAGCTC GGTACCTCCC
        370        380        390        400        410        420
GGGTTATGTT TAGCTCCAGT TACAGTACCA TAAGATACAT TGAATGATTT NGGACAAACC
        430        440        450        460        470        480
ACAACTAAAA ATGCAATTGA AAAAAAATGC TTTATTTGTT GAAATTTGTT GAATGCTATT
        490        500        510        520        530        540
GCTTTATTTT GTTAACCATT   ........   ........   ........   ........
```

Fig. 12

```
         10         20         30         40         50         60
ATTTTACAAC AGTACCGGAA TGCCAAGCTT GATATCGAAT TCCTGCAGCC CGGGGGATCC
         70         80         90        100        110        120
ACTAGTTCTA GAGCTTGGCG CCTCCCGCTC CTCCGGGTAG CTCGTGGGCC GCCGCCGGCC
        130        140        150        160        170        180
CCGGAGCCTT TTATCGAGGC GGGCGGGAGC ACCGCCCCGGC CCCCAGGAAT GCGGCCCCGG
        190        200        210        220        230        240
CCGAGGGCCG ACGGCCGA..            ........           ........
```

Fig. 13A

```
     BCM10.CP1
     BCM10.CP1

1  AAGCTTGATA TCGAATTCCT GCAGCCCGGG GGATCCACTA GTTCTAGAGC TTGGCGCCTC
 61  CCGCTCCTCC GGGTAGCTCG TGGGCCGCCG CCGGCCCCGG AGCCTTTTAT CGAGGCGGGC
121  GGGAGCACCG CCCCGGCCCC AGGAATGCGG CCCCGGCCGA TGGCGGACGG CCGAT
```

Fig. 13B

```
         10          20          30          40          50          60
ATTTTACAAC  AGTACGGAAT  GCCAAGCTTG  ATATCGAATT  CCTGCAGCCC  GGGGGAATCC 70          80          90         100         110         120
ACTAGTTCTA  GAGCTTGGCG  CCTCCCGCTC  CTCCGGGTAG  CTCGTGGGCC  GCCGCCGGCC 130         140         150         160         170         180
CCGGAGCCTT  TTATCGAGGC  GGGCGGGAGC  ACCGCCCGGC  CCCCAGGAAT  GCGGCCCCGG 190         200         210         220         230         240
CCGTCGCCAT  ATTTGGGTGT  CCACCATTCC  TCACCGCTCT  AAAAATAACT  CCCGTGAGGA 250         260         270         280         290         300
ATGGTGCACC  ATCCCTCACC  CGTCGCCATA  TTTGGGTGTC  CCGAGGGGCGG  ACGGCCGCCA 310         320         330         340         350         360
CCGCGGGTGGA  GCTCGGGTACC  TCCCGGGTTA  TGTTAGCTCA  GTTACAGTAC  CATAAGATAC 370         380         390         400         410         420
ATTGATGAGT  TTGGACAAAC  CACAACTAGA  ATGCAGTGAA  AAAAATGCTT  TATTTGTGAA 430         440         450         460         470         480
ATTTGTGATG  CTATTGCTTT  ATTTGTAACC  ATTATAAGCT  GCAATAAACA  AGTTAACAAC 490         500         510         520         530         540
AACAATTGCA  TTCATTTTAT  GTTTCANGTT  CAAGGGGAAG  TNTTGGAAGT  TTTTTAAAN 550         560         570         580         590         600
CAATTAAAAC  ..........  ..........  ..........  ..........  ..........
```

*Fig. 14A*

BCM11.CP1
BCM11.CP1

```
1    AAGCTTGATA TCGAATTCCT GCAGCCCGGG GGATCCACTA GTTCTAGAGC TTGGCGCCTC
61   CCGCTCCTCC GGGTAGCTCG TGGGCCGCCG CCGGCCCCGG AGCCTTTTAT CGAGGCGGGC
121  GGGAGCACCG CCCGGCCCCC AGGAATGCGG CCCCGGCCGT CGCCATATTT GGGTGTC|CAC
                                                              SRE
181  CATTCCTCAC|CCAACACCTG CTGCCTGC|C ACC|GGGAGTTA TTTTAGAGC
     TEF-1        MEF-1                  MEF-2
241  G|GACACCCAA ATATGGCGAC GG|GGCAAGCA NCANGTGTTG G|GTNAGGAAT GGTG|GACACC
         SRE          MEF-1                          TEF-1
301  CAAATATGGC GACGG|CCGGG GCCGCATTCC TGGGGGCCGG GCGGTGCTCC CGCCCGCCTC
          SRE
361  GATAAAGCT CCGGGGCCGG CGGCCCCCG GAACTACCCG GANGAACGGG AAGCGCCAAN
421  CTCTANAACT AATGGATCCC CCGGGCTGCA AGAATTCGAT ATCAAGCTTG GCATTCCGGG
481  TACTGTTGGT AA
```

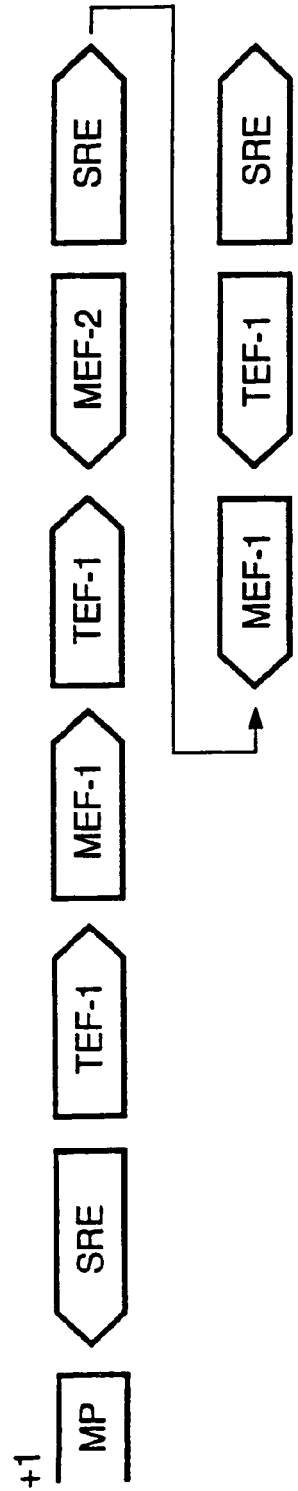

Fig. 14B

```
DNASIS
4573-14g.seq
         10         20         30         40         50         60
ATTTTACAAC AGTACCGGAA TGCCAAGCTT GATATCGAAT TCCTGCAGCC CGGGGATCC 70         80         90        100        110        120
ACTAGTTCTA GAGCTTGGCG CCTCCCGCTC CTCCGGGTAG CTCGTGGGCC GCCGCCGGCC 130        140        150        160        170        180
CCGGAGCCTT TTATCGAGGC GGGCGGGAGC ACCGCCCGGC CCCCAGGAAT GCGGCCCCGG 190        200        210        220        230        240
CCGTCGCCAT ATTTGGGTGT .......... .......... .......... ..........
```

Fig. 15A

BCM14.CP1
BCM14.CP1

```
  1  GATATCGAAT TCNTGCAGCC CGGGGGATCC ACTAGTTCTA GAGCTTGGCG CCTCCCGCTC
 61  CTCCGGGTAG CTCGTGGGCC GCCGCCGGCC CCGGAGCCTT TTATCGAGGC GGGCGGGAGC
121  ACCGCCCGGC CCCCAGGAAT GCGGCCCCCGG CCGTCGCCAT ATTTGGGTGT CGCGTCTAAA
                                                      SRE
181  AATAACTCCC GGCAGGCAGC AGGTGTTGG CAACACCTGC TGCCTGCC GA CACCAAATAT
         MEF-2              MEF-1                    MEF-1
241  GGCGACGG GG CAGGCAGCAG GTGTTGG GAC ACCCAAATAT GGCGACGG CC GCCACCGCGG
              MEF-1                      SRE
301  TGGAGCTCGG TACCTCCCGG GTTATGTTAG CTCAGTTACA GTACCATAAG ATACATTGAT
361  GAGTTTGGAC AAACCACAAC TAGAATGCAG TGAAAAAAAT GCTTTATTTG TGAAATTTGT
421  GATGCTATTG CTTTATTTGT AACCATTATA AGCTGCAATA AACAAGTTAA CAACAACAAT
481  TGCATTCATT TTATTTCA
```

Fig. 15B

+1 [MP] [SRE] [MEF-2] [MEF-1] [SRE] [MEF-1] [MEF-1] [SRE]

```
     10         20         30         40         50         60
ACAACAGTAC CGGAATGCCA AGCTTGATAT CGAATTCCTG CAGCCCGGGG GATCCACTAG
     70         80         90        100        110        120
TTCTAGAGCT TGGCGCCTCC CGCTCCTCCG GGTAGCTCGT GGGCCGGCCGC CGGCCCCGGA
    130        140        150        160        170        180
GCCTTTTATC GAGGCGGGGCG GGAGCACCGC CCGGCCCCCA GGAATGCGGGC CCCGGCCGAG
    190        200        210        220        230        240
GGCGGACACC AATATGGCGA CGGGGCAGGC AGCAGGTGTT GGCGGCTCTAA AATAACTCC
    250        260        270        280        290        300
CGGCAGGCAG CAGGTGTTGG CGCTCTAAAA ATAACTCCCG GCAGGCAGCA GGTGTTGGGA
    310        320        330        340        350        360
CACCCAAATA TGGCGACGGC CGCCACCGCG GTGGAGCTCG GTACCTCCCG GGTTATGTTA
    370        380        390        400        410        420
GCTCAGTTAC AGTACCATAA GATACATTGA TGAGTTTGGA CAAACCACAA CTAGAATGCA
    430        440        450        460        470        480
GTGAAAAAAA TGCTTTATTT GTGAAATTTG TGATGCTATT GCTTATTTG TAACCATTAT
    490        500        510        520        530        540
AAGCTGCAAT AAACAAGTTA ACAACAACAA TTGCATTCAT TTATGTTTC ANGTTCANGG
    550        560        570        580        590        600
GGAAGTGTGG GAAGTTTTTT AAAGCAAGTA AAACTCCACG TACCTTAATA TTACTTACTT
    610        620        630        640        650        660
.......... .......... .......... .......... .......... ..........

Fig. 16A
```

BCM3.CP1
BCM3.CP1

1   GATATCGAAT TCCTGCAGCC CGGGGGATCC ACTAGTTCTA GAGCTTGGCG CCTCCCGCTC
61  CTCCGGGTAG CTCGTGGGCC GCCGCCGGCC CCGGAGCCTT TTATCGAGGC GGGGCGGGAGC
121 ACCGCCCGGC CCCCAGGAAT GCGGCCCCGG CCGAGGGCGG ACACCAATAT GGCGACGGGG
                                              SPI         SRE
181 CAGGCAGCAG GTGTTGGCGC TCTAAAAATA ACTCCGGCA GGCAGCAGGT GTTGGCGCTC
         MEF-2
241 TAAAAATAAC TCCCGGGAGG CAGCAGGTGT TGGGACACCC AAATATGGCG ACGGCCGCCA
       MEF-2        MEF-1                              SRE
301 CCGGCGGTGGA GCTCGGGTACC TCCCGGGTTA TGTTAGCTCA GTTACAGTAC CATAAGATAC
361 ATTGATGAGT TTGGACAAAC CACAACTAAG AATGCAGTGA AAAAAATGCT TTATTTGTTG
421 AAATTTGTTG ATGCTATTGC TTTATTTGTT AACCCATTAT AAGCTTGCCA ATAAACAA

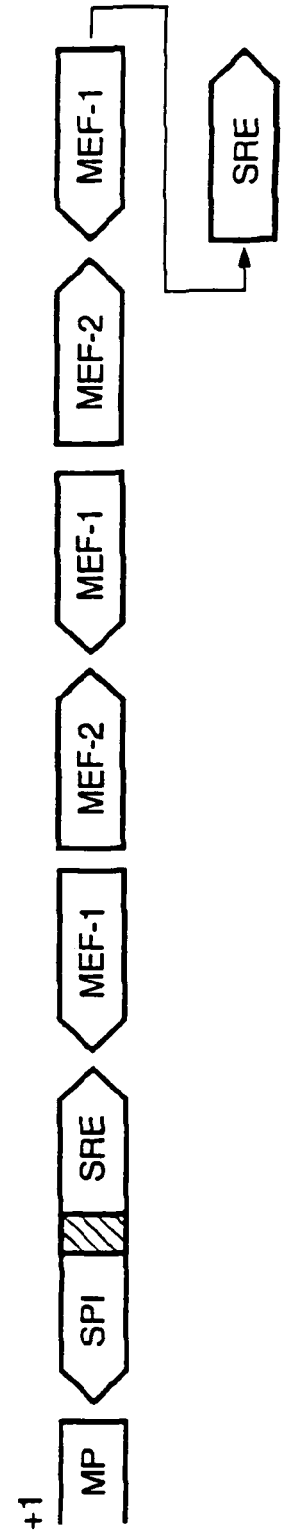

Fig. 16B

```
         10          20          30          40          50          60
ATTTTACAAC  AGTACTGGAA  TGCCAAGCTT  GATATCGAAT  TCCTGCAGCC  CGGGGGNTCC
         70          80          90         100         110         120
ACTAGTTCTA  GAGCTTGGCG  CCTCCCGCTC  CTCCGGGTAG  CTCGTGGGCC  GCCGCCGGCC
        130         140         150         160         170         180
CCGGAGCCTT  TTATCGAGGC  GGGCGGGAGC  ACCGCCCGGC  CCCCAGGAAA  TGCGGCCCCG
        190         200         210         220         230         240
GCCGTCCGCC  CTCGGGCCGTC  GCCATATTTG  GGTGTCCCAA  CACCTGCTGC  CTGCCCACCA
        250         260         270         280         290         300
TCCTCACGGG  AGTTATTTTT  ANAGCGGGGA  GTTATTTTAN  ANCGGGGANT  TATTTTANA.
```

Fig. 17A

BCM5.CP1
BCM5.CP1

```
  1  AAGCTTGATA  TCGAATTCCT  GCAGCCCGGG  GGATCCACTA  GTTCTAGAGC  TTGGCGCCTC
 61  CCGCTCCTCC  GGGTAGCTCG  TGGGCCGCCG  CCGGCCCCGG  AGCCTTTAT   CGAGGCGGGC
121  GGGAGCACCG  CCCGGCCCCC  AGGAATGCGG  NCCCGGCCGT  GCT GCCTGCG CCG
181  TGCCCATATT  TGGGTGTG GG GAGTTATTT  TAGAGCG GGC AGGCANCAGG  TGTTGGG ACA
241  CCCAAATATG  GCGACGG CCG CCACCGCGGT  GGAGCTCGGT  ACCTCCCGGG  TTATGTTAGC
301  TCAGTTACAG  TACCATAAGA  AGTTTGGACA  TACATTGATG  AACCACAACT  AGAATGCAGT
361  GAAAAAAATG  CTTTATTTGT  GAAATTTGTG  GAAATTTGTA  TTTATTTGTA  ACCATTATAA
421  CTGCAATAAA  CAATTTAACA  ACAACAATTG  ATGCTATTGC  ATGTTTCAGG  TTCAGGGGAA
481  GTTTTGGAAG  TTTTTTAAAC  CAATTAAACC  CCAC
```

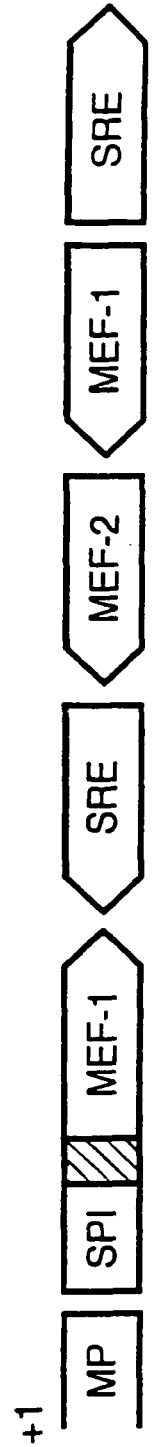

Fig. 18

```
C1-26
         10         20         30         40         50         60
   AGTACCGGAA TGCCAAGCTT GATATCGAAT TCCTGCAGCC CGGGGGATCC ACTAGTTCTA
         70         80         90        100        110        120
   GAGCTTGGCG CCTCCCGCTC CTCCGGGCTC GCCGCCGGCC CCGGAGCCTT
        130        140        150        160        170        180
   TTATCGAGGC GGGCGGGAGC ACCGCCCGGC CCCCAGGAAT GCGGCCCCGG CCGTCGCCAT
        190        200        210        220        230        240
   ATTTGGGTGT CCACCATTCC TCACCGCTCT CCCCGCTCTA AAAATAACTC
        250        260        270        280        290        300
   CCGGCAGGCA GCAGGTGTTG G..........
```

Fig. 20A

```
                 BCM7.CP1
                 BCM7.CP1
C1-26
  1  AAGCTTGATA TCGAATTCCT GCAGCCCGGG GGATCCACTA GTTCTAGAGC TTGGCGCCTC
 61  CCGCTCCTCC GGGTAGCTCG TGGGCCGCCG CCGGCCCCGG AGCCTTTAT  CGAGGCGGGC
121  GGGAGCACCG CCCGGCCCCC AGGAATGCGG NCCCGG CCGT CGCCATATTT GGGTGTC CAC
                                      MEF-2                    SRE
181  CATTCCTCAC GCTCTAAAAA TAACTCCC GG CAGGCAGCAN
        TEF-1    MEF-2
241  GTGT
     +1
```

| MP | SRE | TEF-1 | MEF-2 | MEF-2 | MEF-1 |

| | 10 | 20 | 30 | 40 | 50 | 60 |
|---|---|---|---|---|---|---|
| ACGAGAATGC | NAAGCTTGAT | ATCGAATTCC | NGCAGCCCGG | GGGATNCACT | AGTTCTACAN |

| | 70 | 80 | 90 | 100 | 110 | 120 |
|---|---|---|---|---|---|---|
| CTTGGGGCCT | CCCGCTCCTC | CGGGTACCTC | GTGGGCCGCC | GCCGGCCCCG | GAGCCTTTTA |

| | 130 | 140 | 150 | 160 | 170 | 180 |
|---|---|---|---|---|---|---|
| TCGAGGCGGG | CGGGAGCACC | GCCNGGCCCC | CANGAATGCG | GCCCCGGCCG | TCGCCATATT |

| | 190 | 200 | 210 | 220 | 230 | 240 |
|---|---|---|---|---|---|---|
| TGGGTGTCCC | AACACCTGCT | GCCTGCCCCG | TCGCCATATT | TGGGTGTCGG | GAGTTATTT |

| | 250 | 260 | 270 | 280 | 290 | 300 |
|---|---|---|---|---|---|---|
| TAGANCNGAC | ACCCAAATAT | GGCGACGGCC | GCCACCGCGG | TGGAGCTCGG | TACCTCCCGG |

| | 310 | 320 | 330 | 340 | 350 | 360 |
|---|---|---|---|---|---|---|
| GTTATGTTAN | CTCAGTTACA | GTACNATAAN | ATACATTGAT | GACTTTGGAC | AAACCNCAAC |

| | 370 | 380 | 390 | 400 | 410 | 420 |
|---|---|---|---|---|---|---|
| TAAAATGCAG | TGAAAAAAAT | GCTTTATNTG | TGAAATTTGT | GATNCTATTG | CTTTATTTGT |

| | 430 | 440 | 450 | 460 | 470 | 480 |
|---|---|---|---|---|---|---|
| AACCATTATA | AGCTGCAATA | AACAANTTAA | CAACNACAAT | GGCATNCATT | TTATGTATCA |

| | 490 | 500 | 510 | 520 | 530 | 540 |
|---|---|---|---|---|---|---|
| CGTTCACGGG | GAGGTGTGGG | ........ | ........ | ........ | ........ |

BCM9.CP1
BCM9.CP1

```
  1  AAGCTTGATA  TCGAATTCCT  GCAGCCCGGG  GGATCCACTA  GTTCTAGAGC  TTGGGCGCCTC
 61  CCGCTCCTCC  GGGTAGCTCG  TGGGCCGCCG  CCGGCCCCGG  AGCCTTTTAT  CGAGGCGGGC
121  GGGAGCACCG  CCCGGCCCCC  AGGAATGCGG  CCCCCGG CCGT CGCCATATTT  GGGTGTC CCA
181  ACACCTGCTG  CCTGCC GCGT CGCCATATTT  GGGTGTC GGG AGTTATTTT  AGAGCG GACA
241  CCCAAATATG  GCGACG CCG  CCACCGCGGT  GGAGCTCGGT  ACCTCCCGGG  TTATGTTAGC
301  TCAGTTACAG  TACCATAAGA  TACATTGATG  AGTTGGACA  AACCACAACT  AGAATGCAGT
361  GAAAAAAATG  CTTTATTTGT  GAAATTGTG   ATGCTATTGC  TTTATTTGTA  ACCATTATAA
421  CTGCAATAAA  CAATTTAACA  ACAACAATTG  CATTCATT
```

Fig. 21B

C5-13
DNASIS
4573-13g.seq

```
         10          20          30          40          50          60
ATTTTACAAC  AGTACCGGAA  TGCCAAGCTT  GATATCGAAT  TCCTGCAGCC  CGGGGGATCC
         70          80          90         100         110         120
ACTAGTTCTA  GAGCTTGGCG  CCTCCCGCTC  CTCCGGGTAG  CTCGTGGGCC  GCCGCCGGCC
        130         140         150         160         170         180
CCGGAGCCTT  TTATCGAGGC  GGGCGGGAGC  ACCGCCCGGC  CCCCAGGAAT  GCGGCCCCGG
        190         200         210         220         230         240
ACGCCATTTC  TCTCCTCTAA  AATAACTCCC  GTGAGGAATG  GTGGACACCC  AAATATGGCG
        250         260         270         280         290         300
ACGGGGCAGG  CAGCAGGTGT  TGGGACACCC  AAATATGGCG  ACGGGTGAGG  AATGGTGGAC
        310         320         330         340         350         360
ACCCAAATAT  GGCGACGGGA  CACCCAAATA  TTTGG......  ..........  ..........
```

Fig. 22A

DNASIS
4573-17g.seq

```
         10          20          30          40          50          60
ATTTTACAAC  AGTACCGGAA  TGCCAAGCTT  GATATCGAAT  TCCTGCAGCC  CGGGGGATCC
         70          80          90         100         110         120
ACTAGTTCTA  GAGCTTGGCG  CCTCCCGCTC  CTCCGGGTAG  CTCGTGGGCC  GCCGCCGGCC
        130         140         150         160         170         180
CCGGAGCCTT  TTATCGAGGC  GGGCGGGAGC  ACCGCCCGGC  CCCCAGGAAT  GCGGCCCCGG
        190         200         210         220         230         240
CCGTCGCCAT  ATTGGGTGTC  CCAACACCTG  CTGCCTCCCG  CTCTAAAAAT  AACTCCCGAC
        250         260         270         280         290         300
ACCCAAATAT  GGGCGACGGCC  GCCACCGCGG  TGGAGCTCGG  TACCTCCCGG  GTTATGTTAG
        310         320         330         340         350         360
CTCAGTTACA  GTACCATAAG  ATACATTGAT  GAGTTTGGAC  AAACCACAAC  TAGAATGCAG
        370         380         390         400         410         420
TGAAAAAAAT  GCTTTATTTG  TGAAATTTGT  GATGCTATTG  CTTTATTTGT  AACCATTATA
        430         440         450         460         470         480
AGCTGCAATA  AACAAGTTAA  CAACAACAAT  TGCATTCATT  TTATGTTTCA  NGTTCANGGG
        490         500         510         520         530         540
GAAGTGTNGG  AAGTTTTTTA  AAACAATTNA  AACTCCACGT  TACTTTAATA  TTACTTACTT
        550         560         570         580         590         600
ATCATGGTA.  ..........  ..........  ..........  ..........  ......
```

DNASIS
4573-18g.seq

```
         10         20         30         40         50         60
ATTTTACAAC AGTACCGGAA TGCCAAGCTT GATATCGAAT TCCTGCAGCC CGGGGGATCC
         70         80         90        100        110        120
ACTAGTTCTA GAGCTTGGCG CCTCCCGCTC CTCCGGGTAG CTCGTGGGCC GCCGCCGGCC
        130        140        150        160        170        180
CCGGAGCCTT TTATCGAGGC GGGCGGGAGC ACCGCCCCGGC CCCCAGGAAT GCGGCCCCGG
        190        200        210        220        230        240
CCGAGGGGCGG ACGGCTCCGC CATATTTGGG  . . . . . . .   . . . . . . .   . . . . . . .
```

Fig. 24

C5'-9
DNASIS
4573-19g.seq

```
         10         20         30         40         50         60
ATTTACAAC  AGTACCGGAA  TGCCAAGCTT  GATATCGAAT  TCCTGCAGCC  CGGGGAATC
         70         80         90        100        110        120
CACTAGTTCT  AGAGCTTGGC  GCCTCCCGCT  CCTCCGGGTA  GCTCGTGGGC  CGCCGCCGGC
        130        140        150        160        170        180
CCCGGAGCCT  TTTATCGAGG  CGGGCGGGAG  CACCGCCCGG  CCCCCAGGAA  TGCGGCCCCG
        190        200        210        220        230        240
GATGGTGGGC  AGGCAGCAGG  TGTTGGCGCT  CTAAAAATAA  CTCCCCACCA  TTCCTCACGA
        250        260        270        280        290        300
CACCCAAATA  TGGCGACGGN  ACCATTCCTC  ACCCGTCCGC  CCTCGGCCGC  CACCGCGGTG
        310        320        330        340        350        360
GANCTCGGTA  CCTCCCGGGT  TATGTTANCT  CAGTTACAGT  ACCATAAGAT  ACATTGATGA
        370        380        390        400        410        420
NTTTGGACAA  ACCACAACTA  NAATGCAGTG  AAAAAAATGC  TTTATTTGTG  AAATTTGTGA
        430        440        450        460        470        480
TGCTATTGCT  TTATTTGTNA  CCATTATAAG  CTGCAATAAA  CAANTTAACA  ACAACAATTG
        490        500        510        520        530        540
CATTCATTTT  ATGTTTCANG  .........  .........  .........  .........
```

Fig. 25

C5'-12
DNASIS
4573-20g.seq

```
         10         20         30         40         50         60
ATTTTACAAC AGTACCGGAA TGCCAAGCTT GATATCGAAT TCCTGCAGCC CGGGGGATCC
         70         80         90        100        110        120
ACTAGTTCTA GAGCTTGGCG CCTCCCGCTC CTCCGGGTAG CTCGTGGGCC GCCGCCGGCC
        130        140        150        160        170        180
CCGGAGCCTT TTATCGAGGC GGGCGGGAGC ACCGCCCGGC CCCCAGGAAT GCGGCCCCGG
        190        200        210        220        230        240
CCGTCGCCAT ATTTGGGTGT CCACCATTCC TCACCCAACA CCTGCTGCCT GCCCCAACAC
        250        260        270        280        290        300
CTGCTGCCTG CCGGGAGTTA TTTTTAGAGC GCCAACACCT GCTGCCTGCC CCGAGGGCGG
        310        320        330        340        350        360
ACGGCCGCCA CCGGCGGGA GCTCGGGTACC TCCCGGGTTA CACAACTAGA TGTTAGCTCA GTTACAGTAC
        370        380        390        400        410        420
CATAAGATAC ATTGATGAGT TTGGACAAAC CACAACTAGA ATGCAGTGAA AAAAATGCTT
        430        440        450        460        470        480
TATTTGTTGA AATTTGTGAT GCTATTGCTT TATTTGTAAC CATTATAAGC TGCAATAAAC
        490        500        510        520        530        540
AANTTAACAA CAACAATTGC ATTCATTTTA TTTTCANGTT CANGGGAAGT GTNGGAAGTT
        550        560        570        580        590        600
TTTTAAAACC ..........  ..........  ..........  ..........  ..........
```

Fig. 26

C6-12
DNASIS
4573-15g.seq

```
         10         20         30         40         50         60
ATTTTACAAC AGTACCGGAA TGCCAAGCTT GATATCGAAT TCCTGCAGCC CGGGGGTATC
         70         80         90        100        110        120
CACTAGTTCT AGAGCTTGGC GCCTCCCGCT CCTCCGGGTA GCTCGTGGGC CGCCGCCGGC
        130        140        150        160        170        180
CCCGGAGCCT TTTATCGAGG CGGGCGGGAG CACCGCCCGG CCCCCAGGAA TGCGGCCCCG
        190        200        210        220        230        240
GCCGTCCGCC CTCGGGCCGA GGGGGACGGGCG CTCTAAAAAT AACTCCCCCA ACACCTGCTG
        250        260        270        280        290        300
CCTGCCGGCA GGCAGCAGGT GTTGGGACAC CCAAATATGG CGACGGCCGC CACCGCGGTG
        310        320        330        340        350        360
GAGCTCGGTA CCTCCCGGGT TATGTTAGCT CAGTTACAGT ACCATAAGAT ACATTGATGA
        370        380        390        400        410        420
GTTTGGACAA ACCACAACTA GAATGCAGTG AAAAAAAATGC TTTATTTGTT GAAATTTGTG
        430        440        450        460        470        480
ATGCTATTGC TTTATTTGTA ACCATTATAA GCTGCAATAA ACAAGTTAAC AACAACAATT
        490        500        510        520        530        540
GCATTCATTT TATGTTTCAA GTTCAAGGGG AAGTTTTNGG AAGTTTTTTA AAACAAATTA
        550        560        570        580        590        600
AAACTCCACT  .........  .........  .........  .........  .........
```

BCM15.CP1
BCM15.CP1

```
  1  AAGCTTGATA TCGACCTCCT GCANCCCGGG GGATCCACTA GTTCTAGAGC TTGGCGCCTC
 61  CCGCTCCTCC GGGTAGCTCG TGGGCCGCCG CCGGCCCCGG AGCCTTTTAT CGAGGCGGGC
121  GGGAGCACCG CCCGGCCCCC AGGAATGCGG CCCCGG AGGCGG CCGAGGGGGA
                                        CCCCGG CCGCCCTCGG
                                               SRE
181  ACGGGCTCNA AAAATNACTC CCCCNACACC TGCTGCCTGC CGGCAAGNAA CAAGTTTTGG
         MEF-1
241  GAAACCCNAA TATNGCNAAC GGCGCCACCN CNGTGGAACT CCGTNCCTCC CNGGTTATGT
301  TAACTCNATT ACCGTNCCNT NANAANCNTT NANNAATTTG GAACAACCNC NACTAAAATN
361  CNATNAAAAA AATNCNTTAT TTGTTAAATT TGTTAAGCNA
```

4585-2g.seq

| | 10 | 20 | 30 | 40 | 50 | 60 |
|---|---|---|---|---|---|---|
| | ATTTTACAAC | AGTACCGGAA | TGCCAAGCTT | GATATCGAAT | TCCTGCAGCC | CGGGGGATCC |
| | 70 | 80 | 90 | 100 | 110 | 120 |
| | ACTAGTTCTA | GAGCTTGGCG | CCTCCCGCTC | CTCCGGGTAG | CTCGTGGGCC | GCCGCCGGCC |
| | 130 | 140 | 150 | 160 | 170 | 180 |
| | CCGGAGCCTT | TTATCGAGGC | GGGCGGGAGC | ACCGCCCGGC | CCCCAGGAAT | GCGGCCCCGG |
| | 190 | 200 | 210 | 220 | 230 | 240 |
| | CCGTCGCCAT | ATTTGGGTGTC | GGGAGTTATT | TTTAGAGCGG | ACACCCAAAT | ATGGCGACGG |
| | 250 | 260 | 270 | 280 | 290 | 300 |
| | GGCAGGCAGC | AGGTGTTGGG | ACACCCAAAT | ATGGCGACGG | CCGCCACCGC | GGTGGAGCTC |
| | 310 | 320 | 330 | 340 | 350 | 360 |
| | GGTACCTCCC | GGGTTATGTT | AGCTCAGTTA | CAGTACCATA | AGATACATTG | ATGAGTTTGG |
| | 370 | 380 | 390 | 400 | 410 | 420 |
| | ACAAACCACA | ACTAGAAATG | CAGTTGAAAA | AAATGCTTTA | TTTGTTGAAA | TTTGTTGATG |
| | 430 | 440 | 450 | 460 | 470 | 480 |
| | CTATTGCTTT | ATTTGTTAAC | CCATTATAAG | CCTGCAATAA | ACAATTTAAC | AACAACAATT |
| | 490 | 500 | 510 | 520 | 530 | 540 |
| | GCATTCCATT | TTATNTTTCC | . . . . . . . | . . . . . . . | . . . . . . . | . . . . . . . |

DNASIS
4573-21g.seq

```
           10         20         30         40         50         60
   ATTTTACAAC AGTACCGGAA TGCCAAGCTT GATATCGAAT TCCTGCAGCC CGGGGGATCC
           70         80         90        100        110        120
   ACTAGTTCTA GAGCTTGGCG CCTCCCGCTC CTCCGGGTAG CTCGTGGGCC GCCGCCGGCC
          130        140        150        160        170        180
   CCGGAGCCTT TTATCGAGGC GGGGGGGAGC ACCGCCCGGC CCCCAGGAAT GCGGCCCCGG
          190        200        210        220        230        240
   CCGTCGCCAT ATTTGGGTGT CGGGAGTTAT TTTTAGAGGT GAGGAATGGT GCCGTCCGC
```

Fig. 29

C6'-11
DNASIS
4573-22g.seq

```
        10          20          30          40          50          60
ATTTTACAAC  AGTACCGGAA  TGCCAAGCTT  GATATCGAAT  TCCTGCAGCC  CGGGGGATCC
        70          80          90         100         110         120
ACTAGTTCTA  GAGCTTGGCG  CCTCCCGCTC  CTCGGGGTAG  CTCGTGGGCC  GCCGCCGGCC
       130         140         150         160         170         180
CCGGAGCCTT  TTATCGAGGC  GGGCGGGGAGC ACCGCCCGGC CCCCAGGAAT GCGGCCCCGG
       190         200         210         220         230         240
CCGTCGCCAT  ATTTGGGTGT  CCCGTCGCCA  TATTTGGGTG  TCGGGAGTTA  TTTTTAGAGC
       250         260         270         280         290         300
GGACACCCAA  ATATGGCGAC  GGCCGGCCACC GCGGTGGAGC TCGGTACCTC CCGGGGTTATG
       310         320         330         340         350         360
TTAGCTCAGT  TACAGTACCA  TAAGATACAT  TGATGAGTTT  GGACAAACCA  CAACTANAAT
       370         380         390         400         410         420
GCAGTGAAAA  AAATGCTTTA  TTTGTGAAAT  TTGTGATGCT  ATTGCTTTAT  TTGTAACCAT
       430         440         450         460         470         480
TATAAGCTGC  AATAAACAAG  TTAACAACAA  CAATTGCATT  CATTTTATGT  TTCANGTTCA
       490         500         510         520         530         540
AGGGGAAGTG  TTNGAAGTTT   .......    .......    .......    .......
```

```
         10          20          30          40          50          60
ATTTACAAC  AGTACGGAAT  GCCAAGCTTG  ATATCGAATT  CCTGCAGCCC  GGGGGATCCA
         70          80          90         100         110         120
CTAGTTCTAG  AGCTTGGCGC  CTCCCGCTCC  TCCGGGTAGC  TCGTGGGCCG  CCGCCGGCCC
        130         140         150         160         170         180
CGGAGCCTTT  TATCGAGGCG  GGCGGGAGCA  CCGCCCGGCC  CCCAGGAATG  CGGCCCCGGC
        190         200         210         220         230         240
CGTCGCCATA  TTTGGGTGTCG  ACACCCAAAT  ATGGCGACGG  GGCAGGCAGC  AGGTGTTGGG
        250         260         270         280         290         300
ACACCCAAAT  ATGGCGACGG  GTGAGGAATG  GTGGGGAGTT  ATTTTTAGAG  CGGACACCCA
        310         320         330         340         350         360
AATATGGCGA  CGGCCGCCAC  CGCGGGTGGAG  CTCGGTACCT  CCCGGGTTAT  GTTAGCTCAG
        370         380         390         400         410         420
TTACAGTACC  ATAAGATACA  TTGATGAGTT  TGGACAAACC  ACAACTAGAA  TGCAGTGAAA
        430         440         450         460         470         480
AAAATGCTTT  ATTTGTTGAA  ATTTGTGATG  CTATTGCTTT  ATTTGTAACC  ATTATAAGCT
        490         500         510         520         530         540
GCAATAAACA  ATTTAACAAC  AACAATTGCA  TTCATTTTAT  GTTTCANGTT  CCAGGGGAAG
        550         560         570         580         590         600
TTTTTGGAAG  . . . . . . . . . . . . . . . . . . . . . . . . . . . . . . . . . . . . . . . . . . . . . . . . . . . . . . . . . . . . . .
```

Fig. 31

SYNTHETIC CELL- OR TISSUE-SPECIFIC TRANSCRIPTIONAL REGULATORY REGIONS

CROSS REFERENCE TO RELATED APPLICATIONS

The present application claims priority as a divisional to U.S. patent application Ser. No. 10/137,216, filed May 1, 2002, now abandoned and published as Pub. No.: U.S. 2003/0068631 A1, which is a continuation application to U.S. patent application Ser. No. 09/115,407, filed Jul. 14, 1998, now U.S. Pat. No. 6,410,228, which is based on U.S. Provisional Patent Application No. 60/052,403, filed Jul. 14, 1997, both entitled METHOD FOR THE IDENTIFICATION OF SYNTHETIC CELL- OR TISSUE-SPECIFIC TRANSCRIPTIONAL REGULATORY REGIONS, by Schwartz et al, and all of which are incorporated herein by reference in their entirety, including any drawings.

STATEMENT REGARDING GOVERNMENT INTERESTS

The invention was developed in part as the result of funds received from the Small Business Innovation Research Program under PHS Grant No. DK48567-01 and according the government may have rights in this invention.

BACKGROUND OF THE INVENTION

This invention relates to natural and synthetic cell- or tissue-specific transcriptional regulatory regions that regulate gene transcription in particular cells or tissues. In addition, this invention also relates to the methods for the selection, identification and evaluation of the synthetic cell- or tissue-specific transcriptional regulatory regions. None of the information described herein is admitted to be prior art to the present invention, but is provided solely to assist the understanding of the reader.

Cell- or tissue-specific gene expression plays a central role in the proliferation and differentiation of cells. As the first step of gene expression, transcription is an important step for regulation. The study of transcriptional regulatory regions is one of the major fields in modern biology. The transcriptional regulatory regions are also very important for applications in biotechnology, such as in gene therapy and the production of recombinant proteins.

Transcriptional regulatory regions generally have two portions: transcription initiation sites and enhancers which are capable of regulating the transcription level from a distance to the initiation sites. The binding of transcription factors to the regulatory regions is necessary for the regulatory regions to regulate transcription. The regulatory regions fall into several categories: general regulatory regions which regulate transcription in all cells of an organism, inducible regulatory regions which only regulate transcription in response to certain signals, and cell- or tissue-specific regulatory regions which only regulate transcription in certain cells.

Several methods have been used to identify the regulatory regions. One of these methods is the analysis of regions that are important for the proper expression of cloned genes. The first step is usually to identify rough boundaries of the regulatory regions using deletion and mutation analysis of the cloned genes. These regions include the 5' upstream regions, 3' downstream regions, and sometimes introns or coding sequences within the gene itself. Most studies are performed using chimeric constructs containing a reporter gene such as β-galactosidase (β-gal), chloramphenicol acetyltransferase (CAT), luciferase or growth hormone (GH). The regions that actually bind protein factors can be more accurately defined using DNA footprinting techniques followed by mutation analysis. The sequences that bind protein transcription factors are often referred to as transcription factor binding sites.

Consensus sequences for a number of common binding sites have been determined. One example is the binding site recognized by the family of basic-helix-loop-helix (bHLH) transcription factors. The consensus sequence of binding sites for bHLH proteins is 5'-CANNTG-3', where "N" can be any nucleotide. This binding site is called the "E box" and is found in the regulatory regions of a number of genes that are expressed in diverse cell types, including lymphocytes, muscle cells and fibroblasts. Some bHLH proteins are common to most or all cells while others are cell-specific. In addition, bHLH proteins form heterodimers and the interaction of some of these dimers with DNA is cell-specific. The binding of different bHLH proteins to specific regulatory regions appears to be affected by the variable dinucleotide sequence within the core consensus sequence and the sequence adjacent to the core sequence (Sun, et al., Cell 64: 459-470 (1991)).

Binding sites associated with newly cloned and sequenced genes can also be identified by searching the sequence for homology with the sequences of known binding sites that have been characterized from other, sometimes related, genes.

In addition, several methods were developed to identify the binding sites of transcription factors without cloning of the target genes. Selected and amplified binding site (SAAB) method was used to identify the binding sites for known transcription factors (Blackwell, et al., Science 250: 1104-1110 (1990)). By using this method, synthesized templates with random sequences are incubated with purified transcription factors. Those bound to transcription factors are isolated with electrophoretic mobility shift assay (EMSA). The templates are then amplified by the polymerase chain reaction (PCR). After reiteratively being rebound and reamplified, the binding site of the transcription factor is sequenced and identified. The binding site of transcription factor myc was identified with this method (Blackwell, et al., Science 250: 1149-1151 (1990)).

It is often difficult, however, to identify and purify transcription factors for use in such assays. Indeed, the binding sites are often identified first and then are used to facilitate the identification and purification of transcription factors binding to the sites. Moreover, in many studies, it is crucial to understand the characteristics of certain regulatory regions, whereas it is not necessary to know the transcription factors binding to the regulatory regions. A method similar to SAAB, multiplex selection technique (MuST) was therefore developed (Nullur, et al., PNAS 93: 1184-1189 (1996)). In the multiplex selection technique, purified transcription factors are replaced with crude nuclear extract, so that binding sites can be identified without the identification of transcription factors. The identified binding sites can then be used to identify the corresponding transcription factors.

The regulatory regions often consist of multiple different binding sites for transcription factors. The characteristics of a regulatory region are determined by the composition and arrangement of the binding sites. In addition to naturally-occurring regulatory regions, synthetic regulatory regions can be constructed through the combination and modification of binding sites.

Available naturally-occurring regulatory regions are not always capable of regulating transcription in a desired manner. In these cases, as well as others, synthetic regulatory regions may be utilized to provide the desired functional characteristics. As an example, synthetic herpes simplex virus (HSV) regulatory regions were constructed by linking the 5' nontranscribed domain of an HSV a gene to a fragment containing the transcription initiation site and the 5' transcribed noncoding region from an HSV .gamma. gene (Roizman, PCT 94/14971). The resulting synthetic regulatory regions direct constitutive transcription of the heterologous gene throughout the reproductive cycle of the virus at a high cumulative level. Synthetic regulatory regions were also constructed to achieve high inducible transcription levels and low basal transcription levels (Filmus, et al., PCT 93/20218).

In both of the above cases, the binding sites are well-understood transcription factor response elements. Many binding sites, however, are not well-understood, especially those identified without the cloning of the corresponding transcription factors. These binding sites are therefore only potential transcription factor response elements until they are confirmed to be functional for transcription regulation using functional assays. These assays are usually a laborious and costly task. It is even more complicated for synthetic regulatory regions produced by the combination, modification and rearrangement of various binding sites.

SUMMARY OF THE INVENTION

Applicant has designed useful methods to create, identify and evaluate cell- or tissue-specific synthetic regulatory regions. Specifically, the methods include the selection of transcription factor binding sites, the creation of synthetic regulatory regions using the binding sites and/or portions of known regulatory regions, and the evaluation of the synthetic regulatory regions. The synthetic regulatory regions acquired with this method can be used in gene delivery or gene therapy to achieve desired gene expression in targeted cells. The acquired synthetic regulatory regions can also be used to achieve the production of recombinant proteins at high levels.

The present invention utilizes the recognition that the cells themselves contain all the information required to identify the binding sites that are most important or are recognized by the key transcription factors in the cells. The methods described for the selection of binding sites do not require any previous knowledge of the genes that are expressed or the transcription factors that are present in the cells. Thus, these methods bypass the extensive work needed for the purification, identification, and analysis of transcription factors. In addition, these methods eliminate the need to know the tissue specific transcription factor binding sites. Furthermore, many more potential binding sites can be identified using these methods than using the methods with purified transcription factors. Similarly, the methods for the creation and evaluation of synthetic regulatory regions do not require complete understanding of the binding sites. The binding sites can be linked together in various combinations and with various arrangements, and can then be evaluated to select particular synthetic regulatory regions which are functional in a certain cell line. Therefore, these methods make it possible to create and identify useful synthetic regulatory regions on a large-scale.

As indicated above, the methods discussed herein are useful for identifying regulatory region sequences for gene delivery or gene therapy. One of the major obstacles for gene delivery or gene therapy is the difficulty in expressing genes at preferred levels in certain cells or tissues. The difficulties are partly due to the lack of proper regulatory regions to direct the desired gene transcription. The functional synthetic regulatory regions identified from these methods will provide many candidates for the regulatory regions needed in gene delivery or gene therapy. Moreover, these synthetic regulatory regions will also be candidates for the regulatory regions needed in large-scale production of recombinant proteins, which also requires gene transcription at high level in certain cell lines.

A first aspect of the present invention features a method of identifying binding sites for transcription factors. The method involves identifying the oligonucleotides in protein-oligonucleotide complexes formed between a cellular or nuclear extract from a group of cells and any of a plurality of double-stranded oligonucleotide fragments. Preferably the complexes are separated from free oligonucleotides using size exclusion chromatography. The presence of an oligonucleotide in a complex is indicative that the oligonucleotide includes a binding site.

In preferred embodiments, the double-stranded oligonucleotides are made through the synthesis of single-stranded oligonucleotide and conversion of the single-stranded oligonucleotide to double-stranded oligonucleotide. Also in preferred embodiments, the oligonucleotide fragment has a central random sequence and both restriction sites and primer sequences on both ends. In preferred embodiments, the identifying step includes amplifying, cloning and sequencing the oligonucleotide fragments from the protein-oligonucleotide complexes to identify the binding sites. The amplifying step is preferably performed by polymerase chain reaction.

The oligonucleotide fragments can be of various sizes, but preferably include test sequences between about 5 and 500 bp in length, more preferably between about 5 and 100 bp, still more preferably between 20 and 50 bp.

The term "transcribe" or "transcription" as used herein refers to the synthesis of RNA by RNA polymerase, following a DNA template. Transcription is the first step of gene expression and the most important step for the regulation of gene expression. That is, the regulation of gene expression is achieved mainly through the regulation of transcription.

The term "gene expression" refers to the process in which genetic information flows from DNA to functional molecules, such as proteins or RNA molecules. The regulation of transcription, as a part of gene expression is achieved with the interaction between the regulatory region of a gene and various transcription factors.

As used herein, the term "transcriptional regulatory regions" or "regulatory regions" refers to the regions of a gene controlling the transcription of the gene. A regulatory region often includes several portions. Some of these portions are in the initiation site for transcription, whereas others are located a distance to the initiation site. The term thus includes regions commonly referred to as enhancers.

The term "synthetic regulatory regions" as used herein refers to regulatory regions which are artificially made (i.e., made by humans using molecular biology techniques) such as by the creation with one or more modifications, combinations, or rearrangements of various transcription factor binding sites.

The term "transcription factors" as used herein refers to proteins which bind to the elements of regulatory regions and regulate the transcription of the corresponding genes. According to their functions, transcription factors fall into several categories. These include general transcription factors which are needed by most genes in most cells, cell- or tissue-specific transcription factors which only regulate gene transcription in certain cells, and inducible transcription factors which regulate gene transcription in response to certain signals.

The term "transcription factor binding site" or "binding site" refers to any nucleic acid sequence which can bind transcription factors under transcription conditions or conditions approximating intracellular physical conditions.

As used herein, the term "transcription factor response elements" or "response elements" refers to the functional regulatory region components which can bind transcription factors and thereby regulate transcription of the corresponding genes. Thus, binding sites are potential response elements, their regulatory function can readily be tested and characterized.

As used herein, the term "restriction sites" refers to deoxyribonucleic acid sequences at which specific restriction endonucleases can cleave in a sequence-specific manner.

The term "cells" or "cell" as used herein refers to a membrane-enveloped protoplasmic body capable of independent reproduction. Cells can be maintained, or propagated, in vivo, in vitro or in tissue culture and are capable of being transformed by plasmids as discussed herein.

As used herein "tissue" refers to a population consisting of cells of the same kind performing the same function.

The term "nuclear or cellular extract" refers to a preparation containing all or some of the cellular contents from inside the nuclear membrane or the plasma membrane of cells respectively, particularly including protein components. Such an extract is distinguished from a purified transcription factor.

As used in this context, the term "mixing" refers to putting together oligonucleotides and nuclear or cellular extract, such that the oligonucleotides and components of the extract can contact each other. Preferably a nuclear extract is used.

The term "oligonucleotide" as used herein refers to a nucleic acid molecule consisting of same or different individual nucleotides which are covalently linked together. Oligonucleotides can be single-stranded or double-stranded, consisting of two anti-parallel single-stranded oligonucleotides with complementary sequences. For use in the identification of binding sites, each oligonucleotide strand is preferably between about 5 and 500 nucleotides in length, more preferably between 5 and 100, still more preferably between about 7 and 50, and most preferably between about 20 and 50 nucleotides in length. The term "free oligonucleotide" refers to the oligonucleotides which are not bound to proteins or any other compounds. The term "protein-oligonucleotide complexes" as used herein refers to the complexes comprising oligonucleotides and the proteins bound with the oligonucleotides.

As used in the context of the oligonucleotide fragments, the term "conversion" is used to refer to the synthesis of a single-stranded DNA molecule complementary to another DNA molecule to form a double-stranded DNA molecule.

The term "primer" as used herein refers to a single-stranded oligonucleotide, the 3' end of which can be used as the initiation site for the DNA synthesis with a DNA polymerase. As used herein, the term "primer sequence" refers to the sequence of the primer or the complementary sequence.

As used herein, the terms "5'" and "3'" refer to the two different ends of a single-stranded DNA molecule respectively in accord with common usage. When used in relation to a coding sequence, the terms refer to being in the 5' direction from the coding sequence or in the 3' direction from the coding sequence. For a sequence on a circular nucleic acid molecule, e.g., on a circular plasmid, the terms refer to the direction from a reference sequence but not fully around the chain, and preferably includes a functional relationship. Thus, for example, a regulatory region is 5' to a coding sequence if it is in a position in which it would be expected to functionally affect transcription if in a 5' position on a linear molecule. Usually, a 5' position is closer to the 5' end of a coding sequence than to the 3' end.

As used herein, the term "size exclusion chromatography" refers to a technique for the separation of biomolecules. This approach separates molecules into two groups, one which is smaller than the exclusion size of the chromatographic media and another which is larger than the exclusion size. The protein-oligonucleotide complexes are much larger than free oligonucleotides, so they can be readily separated, utilizing an exclusion size greater than the size of the free oligonucleotides and smaller than the size of protein-oligonucleotide complex. In this context, size refers to the effective radius of the molecule or complex. As indicated above, nuclear or cellular extract, which includes many different transcription factors, is used instead of purified transcription factors in the present invention. The protein-oligonucleotide complexes resulting from the mixing of oligonucleotide fragments and nuclear or cellular extract therefore have many different sizes. As a result, size exclusion chromatography provides a more useful separation than electrophoretic mobility shift assay (EMSA) because size exclusion chromatography produces a simple separation of bound and unbound oligonucleotides while EMSA produces a series of bands distributed over a gel. Due to the nature of the gels typically utilized, EMSA generally also requires an extraction step to recover the bound oligonucleotide from the gel for further manipulation.

The term "amplifying" as used herein refers to increasing the numbers of DNA molecules. The approaches for amplifying include, but are not limited to, polymerase chain reaction.

As used herein, the term "sequencing" refers to the process of identifying the nucleotide sequence of DNA molecules. The term "nucleotide sequence" refers to the linear order of nucleotides in a DNA molecule or other nucleic acid molecules. Methods for sequencing of nucleic acid molecules are well-known to those skilled in the art.

A second aspect of the present invention features a method for evaluating a cell- or tissue-specific synthetic regulatory region or regions. This method involves determining whether a cell is selected under selective conditions. The method uses cells which contain different putative transcriptional regulatory regions located in transcriptional regulatory positions to a selective gene. A cell can only be selected if the selective gene is expressed at sufficiently high levels, and the selective gene will be expressed at the sufficiently high level if the putative transcriptional regulatory region is active in the particular cell. The capability of a cell to be selected in response to the selection condition indicates that the nucleic acid test sequence contains a transcriptional regulatory region active in the cell. The selection condition can be adjusted so that only strong regulatory regions will be effective to be selected in the selection condition. In general, the method involves culturing the cell or cells having the putative transcriptional regulatory sequence.

The term "sufficiently high level" refers to a functional level of expression which depends on the type of selection used and the stringency applied to the selection. Thus, for positive selection, the level is sufficient to allow discrimination of a cell expressing the selective gene at a "sufficiently high level" from an otherwise isogenic cell not expressing the gene at a sufficiently high level. For negative selection, a "sufficiently high level" is a level which allows the cell to grow in the presence of the selection condition.

In a preferred embodiment, the selection condition is a positive selection condition. The capability of at least one cell to be selected in the presence of the selective condition is indicative that the nucleic acid test sequence contains a transcriptional region active in the cell. The selection condition can be adjusted so that only strong regulatory regions will be effective to be selected in the selection condition.

In another preferred embodiment, the selection condition is a negative selection condition, i.e., stress condition; and the selective gene is a protective gene. The growth of the cells is inhibited under the stress condition in the absence of high level expression of the protective gene. Growth of at least one cell in the presence of the stress condition is indicative that the nucleic acid test sequence contains a transcriptional region active in the cell. The stress condition can be adjusted so that only strong regulatory regions will be effective to overcome the stress condition.

The term "regulates" or "regulation" as used herein refers to the effect of nucleic acid sequences or other molecules involved in control of a response or action. In particular, this includes the effects of sequences involved in regulating, controlling or affecting the expression level or rate of structural genes. Generally this includes the binding of transcription factors to sequences, affecting transcription rates or other steps in gene expression.

As used in this context, the term "transcriptional regulatory position" refers to the position where functional regulatory regions can influence the transcription of the selective gene. Transcriptional regulatory positions include, but are not limited to, 5' to the coding sequence of the selective gene, 3' to the coding sequence of the selective gene, and within the intron or signal sequence of the selective gene. For identification and/or evaluation of synthetic regulatory regions, the region 5' to the coding sequence of the selective gene is of particular interest, however, other positions are also of interest and can be utilized in this invention.

The term "cell- or tissue-specific transcriptional regulatory region" as used herein refers to a nucleic acid sequence which is involved in controlling transcription through one or more coding sequences in a cell- or tissue-specific manner. As used herein, the term "cell- or tissue-specific transcription" refers to the gene transcription which occurs at a higher level in cells of a group or in certain tissue as compared to other cells or tissue of the corresponding organism generally.

As used herein the term "transfected" or "transfection" refers to the incorporation of foreign DNA into cultured cells by exposing them to such DNA. This would include the introduction of DNA by various delivery methods, e.g., via vectors or plasmids using naked DNA, DNA-cationic lipid complexes, DNA in liposomes. The methods may include techniques to enhance penetration of the cellular membrane, such as electroporation or use of lytic peptides.

The term "cells of a group" as used herein refers to cells which are differentiated into the same or similar stage, and thereby have the same or similar characteristics, e.g., the same or similar characteristics with respect to control of transcription.

As used herein, the term "vector" refers to a DNA construct which can be transfected into cells. Vectors can be of a variety of different types, including plasmids, viral vectors, and others. Various genes can be inserted into a vector so that the gene can be delivered into cells. The term "insert" as in this context refers to incorporating a nucleic acid sequence into the vector nucleic acid sequence. Vector can include both linear and circular DNA constructs.

The term "selection condition", refers to conditions, under which cells expressing a selective gene show distinguishing features, and thereby can be easily separated from cells not expressing a selective gene. Selection condition can be positive selection condition, or negative selection condition, i.e., stress condition.

The term "positive selection conditions" refers to conditions which distinguish cells expressing the selective gene so that these cells can be easily isolated. The positive selection can be, but not limited to, Fluorescence Activated Cell Sorting (FACS) and magnetic bead sorting.

The term "selective gene" refers to a gene whose expression confers on its host cells a special feature which allows the host cell to be distinguished from other cells with which the host cell is associated. The selective gene can be, but is not limited to, a gene coding a particular antigen or antibody, or a protective gene.

The term "stress conditions" refers to conditions which either kill the cells or inhibit the division and proliferation of the cells. Such stress conditions include, but are not limited to, 1) elevated temperatures; 2) radiation; and 3) contact with particular biochemical agents.

The term "protective gene" means a gene encoding a protein which is capable of protecting cells from a stress condition. Such protective genes include, but are not limited to, genes for 1) adenosine deaminase; 2) dihydrofolate reductase; and 3) heat shock proteins.

The term "biochemical agents" as used herein refers to compounds which kill certain cells or inhibit the division and proliferation of certain cells. These biochemical agents include, but are not limited to, 1) xylofuranosyl-adenine; 2) methotrexate; 3) xylofuranosyl-adenine and deoxycorformacin; 4) alanosine, adenosine, and uridine.

As used in connection with binding sites and regulatory regions, the term "combination" refers to linking together two or more of the same or different kinds of oligonucleotides. The term "modification" refers to a change in the sequence of a DNA molecule, which includes, but is not limited to, the substitution of one or a few nucleotides, or the addition or deletion of one or a few nucleotides as compared to a reference sequence. The term "rearrangement" refers to one or more changes in the order of subsequences of a regulatory region, and can include the insertion of a new subsequence or replacement of a subsequence with a new subsequence. This includes combinations of re-ordering, substitution, and insertion of subsequences.

A third aspect of the present invention features a method, which combines both of the above aspects, for evaluating a cell- or tissue-specific transcriptional regulatory region. The method involves identifying the oligonucleotides in protein-oligonucleotide complexes formed between a cellular or nuclear extract from a group of cells and any of a plurality of double-stranded oligonucleotide fragments. The presence of an oligonucleotide in a complex is indicative that the oligonucleotide includes a binding site. One or more cells are then cultured under a selection condition. Among the cells, at least one cell, and preferably a plurality of cells, contains a nucleic acid test sequence inserted in a transcriptional regulatory position to a selective gene. The test sequence consists of at least one of the binding sites identified using the cellular or nuclear extract. The capability of at least one cell to be selected in the presence of the selection condition is indicative that the nucleic acid test sequence contains a transcriptional region active in the cell. The selection condition can be adjusted so that only strong regulatory regions will be effective to be selected in the selection condition.

In addition, in another aspect, the invention provides synthetic regulatory regions which include all or portions of the synthetic regulatory regions described in Example 5 and in the Drawings. Preferably the synthetic regulatory region is in a transcriptional regulatory position with respect to a coding sequence of interest. A portion of one of the described regions preferably includes at least 20 contiguous nucleotides, more preferably at least 40 contiguous nucleotides, and still more preferably at least 80 contiguous nucleotides of one of the described synthetic regulatory regions. Preferably the portion is placed at about the same position relative to a coding sequence as it occupied in the plasmids used for analysis as described herein. Thus, the portion is preferably within 100 nucleotides, more preferably within 60 nucleotides, and still more preferably within 30 nucleotides of the position it occupied in a corresponding described synthetic regulatory region.

Other features and advantages of the invention will be apparent from the following detailed description of the invention in conjunction with the accompanying drawings and from the claims.

BRIEF DESCRIPTION OF THE DRAWINGS

FIG. 8 shows the sequence of a portion of the plasmid containing the synthetic regulatory region of clone C1-28, including the sequence of the synthetic regulatory region insert (SEQ ID NO:19).

FIG. 9A (SEQ ID NO: 20) & B (SEQ ID NO: 21) show two independently determined sequences of portions of the plasmid containing the synthetic regulatory region of clone C2-27, including the sequence of the synthetic regulatory region insert.

FIG. 11A (SEQ ID NO: 24) & B (SEQ ID NO: 25) show two independently determined sequences of portions of the plasmid containing the synthetic regulatory region of clone C6-16, including the sequence of the synthetic regulatory region insert.

FIG. 12 shows the sequence of a portion of the plasmid containing the synthetic regulatory region of clone C6'-7, including the sequence of the synthetic regulatory region insert (SEQ ID NO: 26).

FIG. 13A (SEQ ID NO: 27) & B (SEQ ID NO: 28) show two independently determined sequences of portions of the plasmid containing the synthetic regulatory region of clone C5-1, including the sequence of the synthetic regulatory region insert.

FIG. 14A (SEQ ID NO: 29) & B (SEQ ID NO: 30) show two independently determined sequences of portions of the plasmid containing the synthetic regulatory region of clone C5-5, including the sequence of the synthetic regulatory region insert.

FIG. 15A (SEQ ID NO: 31) & B (SEQ ID NO: 32) show two independently determined sequences of portions of the plasmid containing the synthetic regulatory region of clone C6-5, including the sequence of the synthetic regulatory region insert.

FIG. 16A (SEQ ID NO: 33) & B (SEQ ID NO: 34) show two independently determined sequences of portions of the plasmid containing the synthetic regulatory region of clone C1-1, including the sequence of the synthetic regulatory region insert.

FIG. 18 shows the sequence of a portion of the plasmid containing the synthetic regulatory region of clone C1-20, including the sequence of the synthetic regulatory region insert (SEQ ID NO: 37).

FIG. 20A (SEQ ID NO: 39) & B (SEQ ID NO: 40) show two independently determined sequences of portions of the plasmid containing the synthetic regulatory region of clone C1-26, including the sequence of the synthetic regulatory region insert.

FIG. 21A (SEQ ID NO: 41) & B (SEQ ID NO: 42) show two independently determined sequences of portions of the plasmid containing the synthetic regulatory region of clone C2-26, including the sequence of the synthetic regulatory region insert.

FIG. 23 shows the sequence of a portion of the plasmid containing the synthetic regulatory region of clone C5'-3, including the sequence of the synthetic regulatory region insert (SEQ ID NO: 45).

FIG. 24 shows the sequence of a portion of the plasmid containing the synthetic regulatory region of clone C5'-5, including the sequence of the synthetic regulatory region insert (SEQ ID NO: 46).

FIG. 25 shows the sequence of a portion of the plasmid containing the synthetic regulatory region of clone C5'-9, including the sequence of the synthetic regulatory region insert (SEQ ID NO: 47).

FIG. 26 shows the sequence of a portion of the plasmid containing the synthetic regulatory region of clone C5'-12, including the sequence of the synthetic regulatory region insert (SEQ ID NO: 48).

FIG. 27A (SEQ ID NO: 49) & B (SEQ ID NO: 50) show two independently determined sequences of portions of the plasmid containing the synthetic regulatory region of clone C6-12, including the sequence of the synthetic regulatory region insert.

FIG. 28 shows the sequence of a portion of the plasmid containing the synthetic regulatory region of clone C6'-8, including the sequence of the synthetic regulatory region insert (SEQ ID NO: 51).

FIG. 29 shows the sequence of a portion of the plasmid containing the synthetic regulatory region of clone C6'-10, including the sequence of the synthetic regulatory region insert (SEQ ID NO: 52).

FIG. 30 shows the sequence of a portion of the plasmid containing the synthetic regulatory region of clone C6'-11, including the sequence of the synthetic regulatory region insert (SEQ ID NO: 53).

FIG. 31 shows the sequence of a portion of the plasmid containing the synthetic regulatory region of clone C6'-22, including the sequence of the synthetic regulatory region insert (SEQ ID NO: 54).

DETAILED DESCRIPTION OF THE INVENTION

The present invention provides methods for identifying and selecting transcription factor binding sites and methods for creating and evaluating synthetic regulatory regions or identified transcriptional regulatory regions. The following description is offered by way of illustration and is not intended to limit the invention in any manner.

The description includes specific examples of preferred embodiments of the present invention. These examples demonstrate how oligonucleotide fragments and nuclear or cellular extracts are used to identify transcription factor binding sites. These examples also demonstrate how synthetic regulatory regions can be created through the modification, combination, and rearrangement of these binding sites or portions thereof and/or of known regulatory regions or binding sites. Furthermore, these examples demonstrate how the synthetic regulatory regions can be evaluated. Such evaluation can identify functional synthetic regulatory regions which direct transcription of a gene at a high level in a particular cell line. These examples include in vivo and in vitro techniques.

Identification of Transcription Factor Binding Sites

The present invention provides a method for identifying nucleic acid sequences which bind cellular proteins, and which are therefore putative transcriptional regulatory sequences. The method can use any of a variety of mixtures of DNA binding proteins, in particular including crude transcription factor preparations from nuclear extracts or whole cell extracts of specific cells or tissues. Certain proteins in such mixtures or extracts will bind to and select specific oligonucleotide sequences from a mixture of oligonucleotide sequences. The oligonucleotide sequences can be random sequences, or fragments of DNA from a genomic or cDNA source, or portions, modifications or rearrangements of known binding sites or other selections of nucleic acid sequences.

The protein-bound or selected oligonucleotides are then identified, such as by amplification, cloning and sequencing. The sequences of selected oligonucleotides will reveal consensus sequences which are recognized by the more abundant transcription factors in these cells. Some of the selected sequences will be recognized by common, non-cell-specific transcription factors but a number of selected sequences will be recognized by cell-specific transcription factors.

Figure 1:
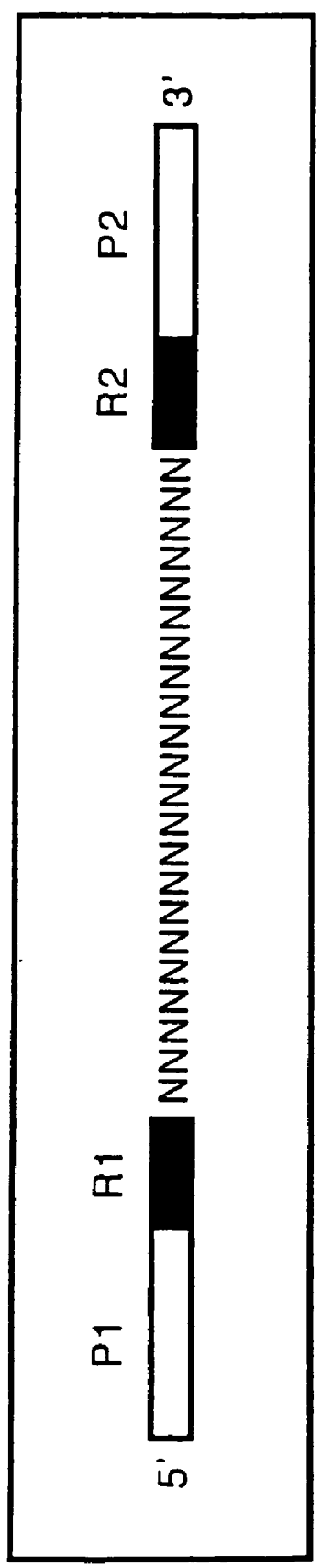
FIG. 1 shows five important features for the synthetic single-stranded oligonucleotides (oligos) used in the described selection method.

As a first step of an exemplary selection method for the identification of synthetic regulatory regions, synthetic single-stranded oligonucleotides (oligos) are constructed or obtained which preferably have five important features. These oligos preferably contain the following:

1. a specific sequence of 10-30 nucleotides at the 5' end to act as a primer annealing site for DNA amplification after the selection process has been performed. This sequence will be identical in all oligos and is labeled "P1" in FIG. 1.
2. a specific restriction enzyme cleavage site located immediately 3' to or within the 3' end of the 5' primer sequence. This site will be used for the cloning of the selected oligos. This site will be identical in all oligos and is labeled "R1" in FIG. 1.
3. a region within the central part of the oligo that contains a number of random nucleotides (preferably ≧10 nucleotides). The sequence in this region will be responsible for the selection of oligos during the selection process.
4. a specific restriction enzyme cleavage site located immediately 3' to the region of random nucleotides. This site will be used with the other restriction site for the cloning of the selected oligos. This site will be identical in all oligos and may be different from the restriction enzyme cleavage site (R1) at the 5' side of the region of random nucleotides and is labeled "R2" in FIG. 1.
5. a specific sequence of 10-30 nucleotides at the 3' end of the oligos to act as a primer annealing site for both the synthesis of a second strand complementary to the original oligos prior to selection and DNA amplification after the selection process has been performed. This sequence will be identical in all oligos but different from the sequence at the 5' end of the oligos (P1) and is labeled "P2" in FIG. 1.

Figure 2:
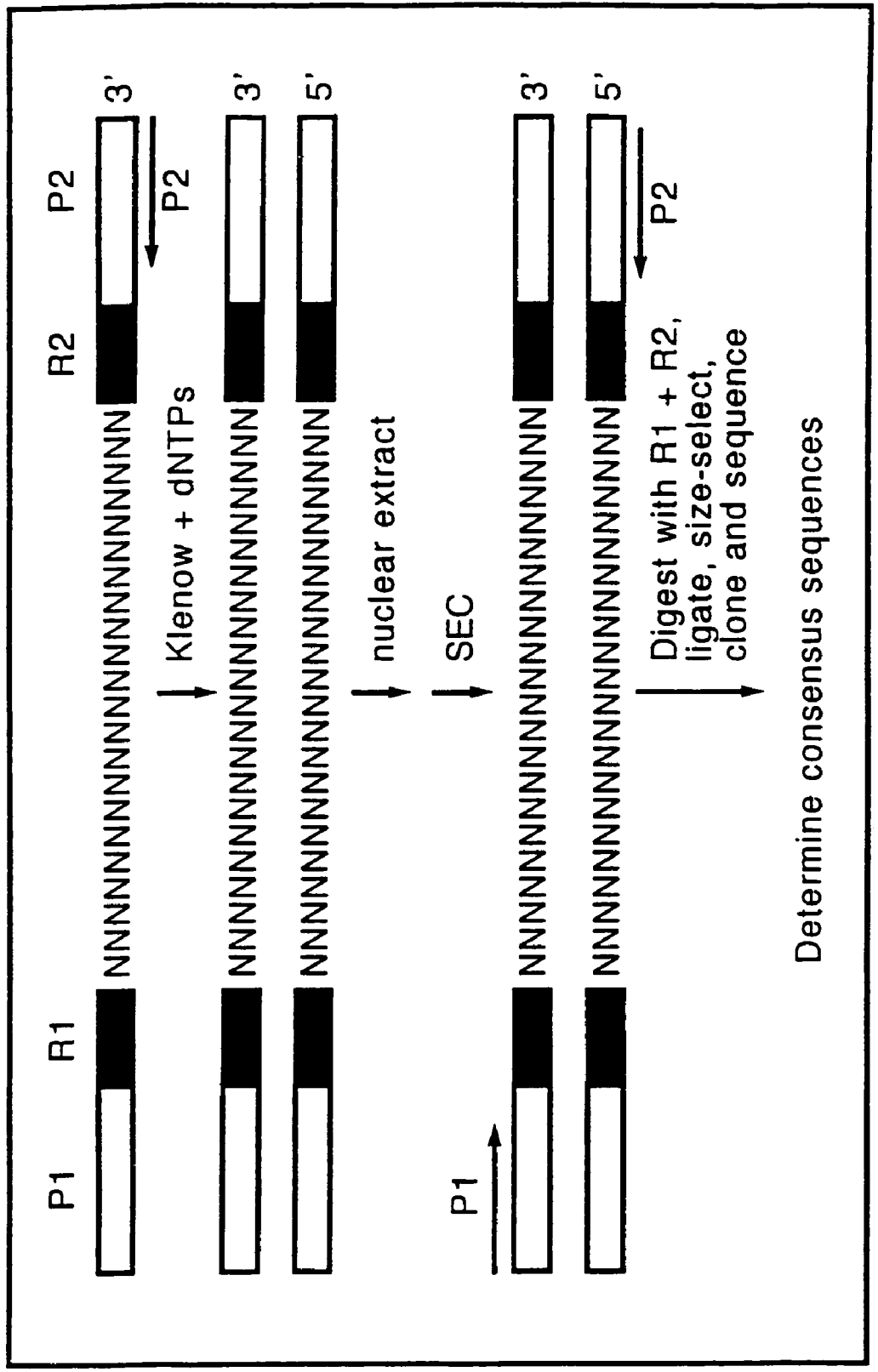
FIG. 2 outlines the overall scheme for an embodiment of transcription factor selection of regulatory regions.

As outlined in FIG. 2, the overall scheme for the selection of binding sites in this embodiment is as follows.

The single-stranded oligo is first converted to a double-stranded oligo by extending primer P2 using a DNA polymerase such as the Klenow fragment of E. Coli DNA polymerase I, T4 DNA polymerase, or T7 DNA polymerase. The double-stranded oligos are gel-purified and incubated with the crude transcription factor preparation, which preferably would be prepared from isolated nuclei but could also be prepared from whole cell extracts (Dent, et al., In Transcription Factors: A Practical Approach, D. S. Latchman (ed.) IRL Press, Oxford, 1-26, (1993)). Transcription factors in the protein extracts will bind to oligos which contain the appropriate recognition sequence or binding site. In preferred embodiments, protein-DNA complexes are separated from unbound oligos by size exclusion chromatography (SEC). SEC is preferable for this step because the protein-DNA complexes will be heterogeneous in size due to differences in the molecular weights of the bound transcription factors and the possibility that multimeric protein complexes may bind to some binding sites. Thus, electrophoresis would result in a distribution of bands across the gel which would require separate extraction. In contrast, SEC media and conditions can be selected to provide a sharp separation of free and protein-bound oligos.

The selected oligos are then purified, amplified using primers P1 and P2, and digested with restriction enzymes R1 and R2 to excise the central protein-binding regions from the flanking primer sequences. Those skilled in the art can readily determine appropriate primers and restriction enzymes. The digested oligos are then ligated to form concatamers, and fragments in the 200-400 bp range are purified and cloned into an appropriate cloning/sequencing vector. Cloning 200-400 bp concatamers, which contain 20 or more different selected sequences, allows the acquisition of much more sequence information per sequencing reaction than would be obtained if single selected oligos were cloned and sequenced. The method, however, can also utilize single oligos or other size concatamers.

The sequences of individual selected oligos are aligned to identify consensus sequences for the most abundant transcription factors. These sequences are tested for cell specificity, either individually or in combination, by cloning them upstream of a basal heterologous regulatory region driving a reporter gene. The selected oligos can also be used in combination with known transcription factor response elements to make synthetic regulatory regions.

Since this method does not require knowledge of the genes that are expressed or the transcription factors that are present in the cells of interest, this method can be used to identify transcriptional regulatory sequences which are utilized in cell types or under conditions in which gene regulation is poorly understood. The process can be used to identify and characterize regulatory regions that are highly active in a specific cell type or tissue, as well as cell-specific regulatory regions. This can be extended to include different developmental stages, induction states, or transformation states of cells.

Evaluation Method for Synthetic Regulatory Regions

Because of the limitations in previous methods, as discussed above, new methods are needed to evaluate the functions of synthetic regulatory regions. This invention provides an approach utilizing the expression of proteins capable of protecting cells from stress conditions, such as drugs, to select functional synthetic regulatory regions. In addition to evaluating synthetic regulatory regions, this method can be used to evaluate any of a variety of other transcriptional regulatory sequences.

A number of different proteins are capable of protecting eukaryotic cells from the toxic effects of specific biochemical agents (drugs). The genes coding for some of these proteins (protective genes) have been used to select for the amplification of other non-selectable genes that are linked to the protective gene. This amplification occurs after integration of the two linked genes into the same site of the genome of transfected cells. These selection systems have been used to amplify exogenous genes to increase the production of recombinant proteins (Kaufman, Meth. Enzymol. 185: 537-566 (1990); Kellems, Current Opinion in Biotechnology 2: 723-729 (1991); Kellems, Methods in Molecular Genetics 5: 143-155 (1994)).

The gene most frequently used in gene amplification schemes is the gene coding for dihydrofolate reductase (DHFR), which provides protection against the toxic effects of the drug methotrexate. After transfection of methotrexate sensitive cells with an expression plasmid containing both the DHFR gene and the gene of interest, these genes can be induced to coamplify by treating the cells with increasing concentrations of methotrexate (Kaufman, Meth. Enzymol. 185: 537-566 (1990)).

The gene for adenosine deaminase (ADA) can also be used to select for the amplification of linked genes (Kellems et al., in Genetics and Molecular Biology of Industrial Microorganisms, Hershberger et al., (ed.) American Society for Microbiology, Washington, 215-225 (1989); Kellems, Current Opinion in Biotechnology 2: 723-729 (1991); Kellems, in Gene Amplification in Mammalian Cells, Marcel Dekker, Inc., New York, 207-221 (1992); Kellems, Methods in Molecular Genetics 5: 143-155 (1994)). ADA is an enzyme involved in purine metabolism in mammalian cells and can provide protection against the toxic effects of the drug such as xylofuranosyl-adenine (xyl-A).

Applicant has found that the ADA gene can be used in a method for evaluating the transcriptional activity of transcriptional regulatory regions. In this method, a high level of ADA gene expression is required to allow growth of a cell. Such high level expression will only be provided if a test sequence inserted in a transcriptional regulatory position, e.g., upstream to the ADA gene, is effective in allowing sufficient transcription of the ADA gene.

In this system, synthetic regulatory regions/enhancers will be assembled from mixtures of synthetic oligonucleotides, fragments of cloned natural regulatory regions, and/or protein binding sites using a random combinatorial approach. The synthetic regulatory regions will be inserted upstream of a basal TATA box and functional ADA minigene (cDNA) contained in a plasmid. This will produce libraries of synthetic or recombined regulatory regions which can contain millions of different combinations. These plasmid libraries will then be transfected into cells of different origins and the transfected cells will be selected for increased ADA activity in transient assays. Cells that express no or low levels of ADA will be killed and lost from the culture due to insufficient ADA activity. Cells that express high levels of ADA, due to the strength of the synthetic regulatory region, will survive. This procedure thus selects for synthetic regulatory regions that drive the expression of ADA in that specific cell type. This approach can be used to develop strong regulatory region that will function in cells or tissues for which there is poor understanding of patterns of gene expression or the regulatory regions of specific genes have not been characterized.

This approach is not limited to the use of ADA-based selection protocols but can also utilize selection strategies developed based on the expression of other genes, including but not limited to dihydrofolate reductase (DHFR), metallothienin, CAD, thymidylate synthetase, ornithine decarboxylase, etc. (see Kellems, Current Opinion in Biotechnology 2: 723-729 (1991) for a more extensive list).

Examples of how this type of selection system could be used are outlined below:

Creation of Synthetic Regulatory Regions from Transcription Factor Binding Sites As discussed previously, the synthetic regulatory regions are created to have altered composition, order, and/or spacing of individual binding sites for transcription factors. Creation of the synthetic regulatory regions usually uses a combination of specific restriction sites. If convenient sites are not available, alternatives can be used, such as chemical resynthesis or engineering of different restriction sites onto the ends of the binding sites. A variety of methods can be used to assemble the different components, such as the method of nucleic acid ordered assembly with directionality (NOMAD) (Rebatchouk, et al., PNAS 93: 10891-10896 (1996)).

NOMAD is a general cloning strategy that can manipulate the binding sites in the form of "module" having a standardized cohesive structure. Specially designed "assembly vectors" allow for sequential and directional insertion of any number of binding sites in an arbitrary predetermined order, using the ability of type IIS restriction enzymes to cut DNA outside of their recognition sequences (Rebatchouk, et al., PNAS 93: 10891-10896 (1996)). NOMAD ensures the convenient construction of the synthetic regulatory regions with altered composition, order, or spacing of individual binding sites for transcription factors. The acquired synthetic regulatory regions can then be evaluated, such as with the ADA selection method.

Biochemical Agents Used in ADA Selection

A number of protocols have been developed that use ADA selection to amplify genes (Kellems et al., in Genetics and Molecular Biology of Industrial Microorganisms, Hershberger et al., (ed.) American Society for Microbiology, Washington, 215-225 (1989); Kellems, Current Opinion in Biotechnology 2: 723-729 (1991); Kellems, in Gene Amplification in Mammalian Cells, Marcel Dekker, Inc., New York, 207-221 (1992); Kellems, Methods in Molecular Genetics 5: 143-155 (1994)).

In this invention, a method has been developed which uses ADA to identify and evaluate regulatory regions, such as synthetic regulatory regions, or other regulatory sequences. This method can be performed in a number of different ways, including the following.

The simplest method uses increasing concentrations of xylofuranosyl-adenine (xyl-A) alone. In cells expressing low levels of ADA, xyl-A is converted to xyl-AMP by adenosine kinase. Xyl-AMP is subsequently converted to xyl-ATP which can then be incorporated into RNA by RNA polymerase where it acts to block further extension of the RNA chain. This chain termination is due to the fact that, unlike the normal sugar contained in ribonucleosides, xylose lacks a 3' hydroxyl group which is required for RNA chain extension. ADA is capable of detoxifying xyl-A by converting it to hypoxanthine and xylose-$P_i$, both of which are non-toxic. Since the chain terminating effect of xyl-A is independent of DNA synthesis, xyl-A will readily kill non-dividing as well as dividing cells (Kellems et al., in Genetics and Molecular Biology of Industrial Microorganisms, Hershberger et al., (ed.) American Society for Microbiology, Washington, 215-225 (1989)). The concentration of xyl-A required to kill a specific type of cell depends on the level of endogenous ADA expressed by those cells. Most cells normally produce relatively low levels of ADA and are, therefore, killed quickly by low (micromolar) concentrations of xyl-A. Endogenous ADA can be selectively inhibited by incubation with deoxycoformacin. This protocol has the limitation that ADA expression increases with increasing concentrations of xyl-A up to only about 10 μM. Cells can be selected that are resistant to higher concentrations of xyl-A but they do not express higher levels of ADA. It was found that cells selected for resistance to more than about 10 μM xyl-A were deficient in the activity of adenosine kinase, which is responsible for converting xyl-A to xyl-AMP, the first step in producing xyl-ATP which is a substrate for RNA polymerase.

An alternative method of ADA selection, termed 11AAU selection (Yeung et al., J. Biol. Chem. 258: 8338-8345 (1983); Yeung et al., J. Biol. Chem. 258: 8330-8337 (1983)), was subsequently developed that used a combination of 1) alanosine, which inhibits the de novo synthesis of AMP; 2) adenosine, which then becomes a required substrate for adenosine kinase via the salvage biosynthetic pathway; and 3) uridine, which overcomes the inhibitory effect of high concentrations of adenosine on UMP synthesis. This selection protocol requires adenosine kinase to produce AMP and thus greatly reduces the chance that this enzyme will be affected during the selection process. In this protocol adenosine is used at a concentration that is cytotoxic to normal cells. Thus, this protocol selects for increased expression of ADA, which is required to detoxify the excess adenosine. ADA activity can be further increased by exposing cells to both 11AAU selection and increasing concentrations of deoxycoformacin (Yeung et al., J. Biol. Chem. 258: 8330-8337 (1983)). However, some cells do not tolerate the 11AAU/deoxycoformacin selection system well.

Yet another selection system uses xyl-A as the cytotoxic agent in combination with deoxycorformacin to inhibit endogenous ADA activity (Kaufman et al., PNAS 83: 3136-3140 (1986); Kellems et al., in Genetics and Molecular Biology of Industrial Microorganisms, Hershberger et al., (ed.) American Society for Microbiology, Washington, 215-225 (1989)). This is a very effective method to select for increased ADA levels but does not provide any selection for the maintenance of adenosine kinase activity. Therefore, this method should not be used for long periods of time as this increases the probability that adenosine kinase mutants will arise.

These selection methods can be used in the selection and evaluation of synthetic regulatory regions, as discussed previously. An exogenous ADA gene under the control of one of the synthetic regulatory regions to be evaluated is transfected into cells that are then placed under selective pressure. The surviving cells should carry the functional synthetic regulatory regions which direct the strong transcription of ADA gene, protecting the cells from the toxic effect of the biochemical agents.

As indicated, a variety of different selection methods can be used to identify effective synthetic regulatory regions. Generally a selection method based on expression of a protective gene can be used, where the selection method is able to distinguish between low or moderate expression levels and high expression levels. This allows a semi-quantitative comparison of the relative effects of different synthetic and natural promoters or other regulatory regions.

Selection systems can also be used, such as magnetic sorting and FACS. An example of such systems is the MAC Selecting System (Miltenyi Biotec, Auburn, Calif.). In this system, a gene encoding CD4 antigen is the selective gene and CD4 antibody complexed to magnetic beads is used to separate cells expressing CD4 antigen from non-expressing cells. Alternatively, fluorescence labeled CD4 antibody can be used to detect CD4 expressing cells, and expressing cells can then be separated by FACS.

Synthetic Regulatory Regions for Muscle Cells

The development of synthetic regulatory regions with high level activity in a particular cell type or state can be illustrated by the identification of regions producing high level expression in muscle cells. Individual synthetic oligonucleotides can be synthesized containing known consensus sequences capable of binding cell-specific transcription factors (transcription factor binding sites), ligated together in random combinations and cloned upstream of the ADA gene as described above. For example, consensus sequences for muscle-specific binding sites, including serum binding sites (SREs), MEF-1 sites, MEF-2 sites, and/or TEF-1 sites, can be used. This library of synthetic regulatory regions can then be transfected into muscle cells (e.g., $C_2C_{12}$, SOL8, or primary myoblast cells). The ADA selection system allows the selection against clones containing weak muscle regulatory regions and for clones containing strong muscle regulatory regions.

Also, cloned or PCR-amplified cell-specific regulatory elements can be digested with one or more frequent cutting restriction enzymes to produce mixtures of small DNA fragments containing sequences capable of binding cell-specific transcription factors. These fragments would be ligated together in random combinations and cloned upstream of the ADA gene as described above. For example, regulatory regions for the skeletal α-actin, cardiac α-actin, myosin heavy chain, and myosin light chain genes, which contain the muscle-specific binding sites, can be used.

This library of synthetic regulatory regions would then be transfected into muscle cells (e.g., $C_2C_{12}$, SOL8, or primary myoblast cells). The ADA selection system would allow the selection against clones containing weak muscle regulatory regions and for clones containing strong muscle regulatory regions.

Identification of 3', 5', and Intron Regions that Enhance Gene Expression

Alone, or in combination with the promoter selection methodology described herein, one may use the combinatorial approach combined with a selection methodology to identify gene control regions, including novel regions, such as 3' untranslated regions (3'UTR), 5' untranslated regions (5'UTR), and intron elements that have the effect of enhancing gene expression when inserted into a plasmid construct in the proper orientation to the gene. One skilled in the art will immediately recognize the proper position of the element to be inserted from the terms 3'UTR, 5'UTR, and intron. 3'UTR, 5'UTR, or intron regions from known gene are randomly combined, for example, by the method described herein in connection with promoter/enhancer sequences, and inserted into the appropriate position relative to the coding sequence of the gene of interest. As indicated above, other sequences can also be used, including but not limited to random sequences and combinatorial rearrangements of known sequences. A selection procedure, such as that described above, is then employed to identify control regions which have the effect of enhancing the expression of the gene with which they are associated.

Selection of Transcriptional Regulatory Regions from Various Tissue Types

While the methods described herein are exemplified by selection of muscle-specific promoter sequences, the use of these methods is by no means restricted to muscle cells. For example, cells of lung, kidney, brain, heart, eye, inner ear, epithelial, endothelial, mesothelial, smooth muscle, neuronal, lymphocyte, macrophage, glial, microglial, intestinal, colon, bone, hematopoietic, skin, liver, cancerous, precancerous, metastatic, fetal, or vascular origin may be used to identify expression enhancing regulatory regions. In addition, regulatory elements derived from one cell type may be selected for in a different cell type for expression enhancing capacity. Such a procedure would also fall within the scope of this invention.

Identification of Reduced-Size Active Portion of Synthetic Regulatory Region

Using methods described above, one can identify synthetic regulatory regions which provide appropriate expression levels in a selected type or group of cells. Depending on the oligonucleotide length utilized in the identification, it can be useful to reduce the size of the synthetic regulatory region by identifying and utilizing a portion or portions of the larger region which provide the enhanced transcriptional regulatory effects. Such identification can be performed by routine methods, such as by replacement of portions of an effective regulatory region with equal length inactive sequences and determining the activity of the resulting modified region. If the expression enhancing activity is significantly reduced, this indicates that the modified region includes at least part of a sequence which provides the expression enhancing activity. On the other hand, if the modification does not significantly affect the resulting expression, this indicates that the modified portion does not contribute to the activity of the synthetic regulatory region. Thus, the portion or portions which significantly contribute to the transcriptional regulatory activity can be used as new smaller synthetic regulatory regions separately from other parts of the original synthetic regulatory region. Generally the position of the active portion or portions with respect to the coding sequence should be maintained at approximately the position it occupied in the original synthetic region. However, it will not usually be necessary to maintain exactly the same position, but will preferably be within 100, 60, 30, or fewer bases of the original position.

While the active portions can be of various sizes, preferably the portion providing a small synthetic transcriptional regulatory region includes at least 20 contiguous nucleotides, and more preferably includes at least 40, 60, 80, or 100 contiguous nucleotides of the original synthetic region.

The present invention is further illustrated by the following examples, which are not intended to limit the present invention in any way.

Example 1

Generating the Libraries of Synthetic Muscle Specific Regulatory Regions by Random Combination of Regulatory Elements Available naturally-occurring muscle specific regulatory regions cannot regulate transcription in all desired manners in muscle cells. Synthetic muscle specific regulatory regions are therefore needed to provide new candidates for controlling the transcription. The synthetic muscle specific regulatory regions can be constructed by random combination of transcription factor binding sites which are known to be important in the regulation of general transcription or muscle cell-specific transcription. This example illustrates how synthetic muscle-specific regulatory regions can be constructed using a selection of known binding sites.

The sequences which are shown in the following include MRE (muscle response element), E-box which is the binding site recognized by the family of basic-helix-loop-helix (bHLH) transcription factors, and the binding sites for transcription factors MEF-2, TEF-1 and Sp1.

```
MEF-2    CTCTAAAAATAACTCC         (SEQ ID NO: 1)

MRE      GCCCAACACCCAAATATGGCTT   (SEQ ID NO: 2)

E-box    CTCACCTGCTG              (SEQ ID NO: 3)

TEF-1    GCCGCATTCCTGGG           (SEQ ID NO: 4)

Sp1      CCCCGCCC                 (SEQ ID NO: 5)
```

The first step in constructing the synthetic regulatory regions is to synthesize double-stranded oligonucleotides containing one of the above binding sites. This synthesis is performed for each of the binding sites to be included. The oligonucleotides should be sticky ended, i.e., have ends which are single-stranded with sequences complementary to each other. The oligonucleotides preferably fit in one or two helical turns so that elements reside on the same face after being linked together. This can be achieved by constructing a sequence so that the contact points contained in the elements are approximately 10 base pairs apart from each other (or approximately 20 base pairs apart). Those skilled in the art will know appropriate techniques to provide appropriate spacing and sticky ends.

These oligonucleotides are mixed together using a particular ratio of different oligonucleotides. This ratio can be varied to favor the presence of a particular element. For example, MEF-2, E-box, MRE, TEF-1, and Sp1 can be mixed at a ratio of 4:2:2:2:1, in order to increase the probability of MEF-2 presence in the synthetic regulatory regions. Similarly, the ratios can be biased in favor of other binding sites. The mixed oligonucleotides can automatically be linked together non-covalently through annealing of the sticky ends. The oligonucleotides are then ligated using a DNA ligase. The oligonucleotides are therefore covalently linked together to form new and longer oligonucleotides.

The ligated oligonucleotides are cut through partial digestion with a nuclease. The digested oligonucleotides are separated by gel electrophoresis and the oligonucleotides with a particular size, e.g., 200 bp, are recovered from the gel. The recovered oligonucleotides are then capped with a sticky ended adaptor using a DNA ligase.

The capped oligonucleotides are then cloned into appropriate vectors for expression analysis. For example, for identification of effective myogenic promoter/enhancer sequences, the capped oligonucleotides can be inserted at a site adjacent to the Sk-actin TATA-box in a myogenic vector system (MVS) β-gal construct or at −200 in MVS β-gal construct.

Example 2

Comparison of Relative Regulatory Region Activity During Differentiation at Primary Myoblast Cells The synthetic regulatory regions should be evaluated to confirm they are functional in the regulation of transcription. Large-scale evaluation can be done with the stress condition selection (e.g., ADA), as discussed above; medium-scale evaluation can be done either with the stress condition selection, or with the following approach or with other analyses of expression level. This example also illustrates the selection of synthetic regulatory regions which regulate transcription rates in particular cells, in this example, muscle cells.

In this approach, the synthetic regulatory regions are inserted into a vector to regulate the transcription of a reporter gene, instead of a selective gene. The reporter genes include, but are not limited to, the genes encoding β-gal and luciferase. Minilysate prepared DNA, such as the constructs of example 1, is transferred into myogenic cultures in 96 well microtiter dishes. β-gal activity is assayed by routine methods, e.g., mini ONPG assay, and compared to β-gal expression driven by the cytomegalovirus immediate early promoter (CMV-β-gal). High β-gal activities represent the strong synthetic regulatory regions. Of course, other non-cell-specific regulatory regions could also be used for a reference expression level.

The above approach can also be used for the further evaluation of synthetic regulatory regions acquired using the stress condition approach, as the β-gal activity assay can provide quantitative information about the regulatory regions being evaluated.

Figure 3:
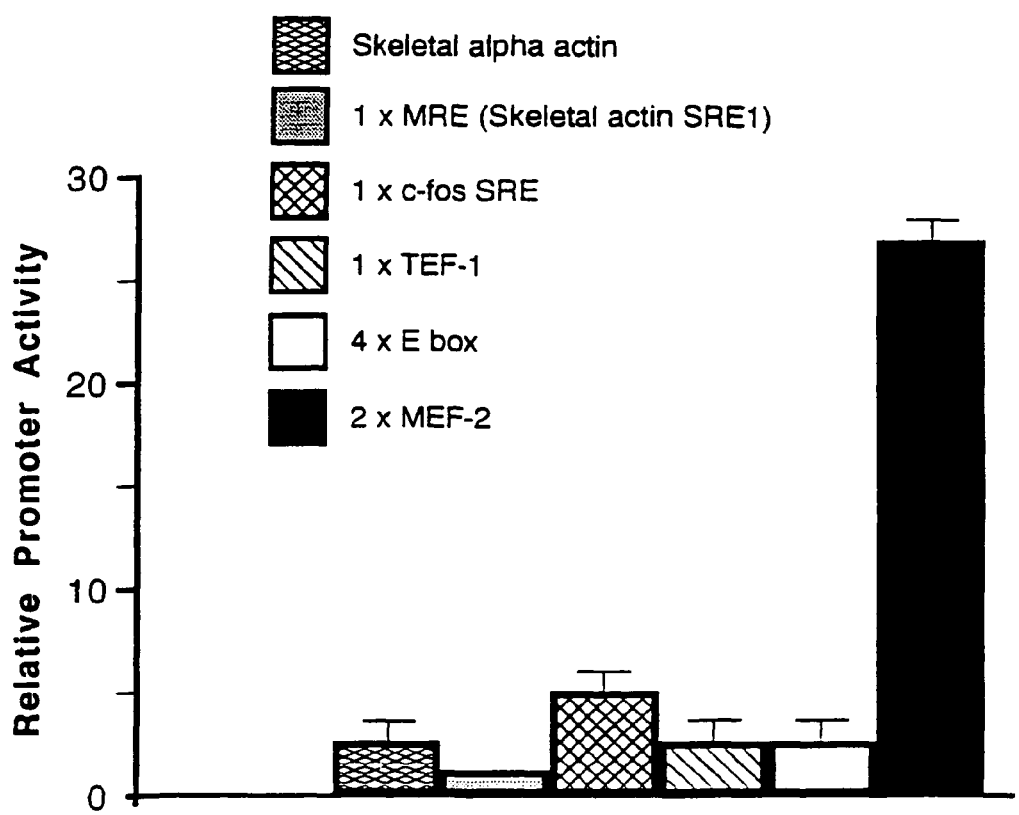
FIG. 3 is a comparison of relative regulatory region activity of a number of different regulatory regions during differentiation in primary myoblast cells.

FIG. 3 shows the comparison of relative regulatory region activity during differentiation of primary myoblast cells. This experiment was done using reporter gene product assay. The regulatory region containing 2×MEF-2 has about a five-fold higher activity than other regulatory regions tested. This result indicates that the regulatory region containing 2×MEF is capable of stimulating gene transcription at a high level in myoblast cells.

Example 3

Differential SRF Activity on c-Fos SRE vs Muscle SRE

The above approach (Example 2) using a reporter gene product assay was used to determine the differential SRF activity on c-Fos SRE and muscle SRE, the sequences of which are shown in the following. These sequences have sequence similarity in the SRF binding sites, which are underlined.

```
C-FOS SRE:
ACAGGATGTCCATATTAGGACATCTGCG      (SEQ ID NO: 6)

MUSCLE SRE:
GCCCGACACCCAAATATGGCGACGGCCG      (SEQ ID NO: 7)
```

Figure 4:
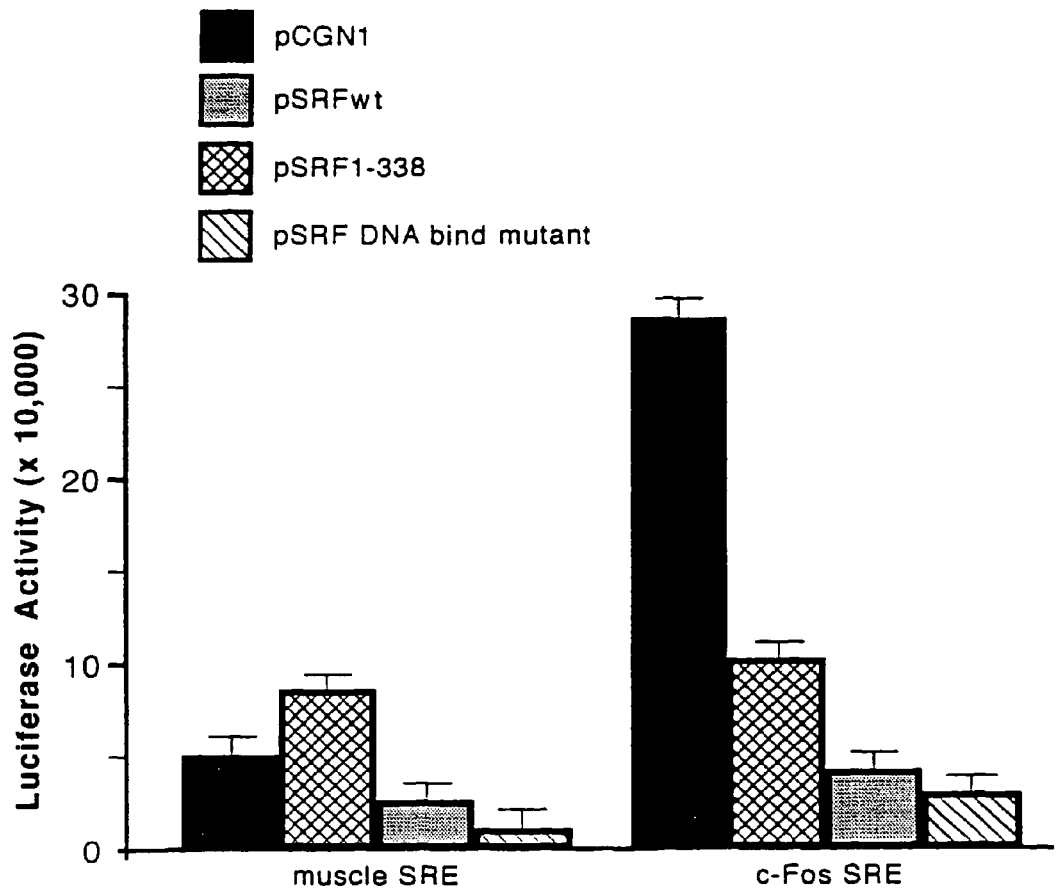
FIG. 4 shows the differential SRF activity on c-Fos SRE (SEQ ID NO: 6) vs muscle SRE (SEQ ID NO: 7).

The c-Fos SRE and muscle SRE were inserted into a vector to regulate a reporter gene encoding a luciferase. The vector constructs were transferred into $C_2C_{12}$ myoblasts. The luciferase gene is transcribed in the presence of various SRF's. The luciferase activity was then assayed. All the transcription factors tested except GCN1 showed similar activities on c-Fos SRE and muscle SRE. On c-Fos SRE, GCN1 has about 3-fold higher activity than SRFwt does. On muscle SRE, in contrast, GCN1 has about 2-fold lower activity than SRFwt does (FIG. 4). These results indicate that minor variations in transcription binding sites can result in a major difference in regulatory region activity in the presence of a particular transcription factor.

Example 4

Selection of Tissue- or Cell-Specific Elements in Vivo

In addition to in vitro selection approaches, synthetic tissue- or cell-specific transcriptional regulatory regions can be selected and evaluated in vivo. One of the most important uses of the synthetic elements is to regulate tissue- or cell-specific gene expression in an organism. The synthetic elements identified in vitro may be further studied in vivo to better evaluate or understand their functions. Useful in vivo approaches include, but are not limited to, transgenic animals and muscle injection.

A. Insertion of Vectors into Transgenic Mice

Vectors are constructed containing a reporter gene, e.g. β-gal, under the control of the synthetic elements identified as having in vitro activity in a particular type or types of cells, e.g., in muscle cells. Transgenic mice carrying the vectors can be generated by standard oocyte injection (Brinster, et al, Proc. Natl. Acad. Sci. USA 82: 4438-4442 (1958)) and bred to demonstrate stable transmission of transgenes to subsequent generations. Transgenics can be identified by polymerase chain reaction or Southern genomic DNA blotting analysis, such as from tail cut DNA.

Transgenics can be tested for tissue specific expression, e.g., muscle specific expression, of the transferred vector by RNA blotting of total RNA isolated from several tissues, or by .beta.-gal assay. For example, samples can be taken and analyzed from skeletal muscle, gonad, lymph nodes, liver, spleen, kidney, lungs, heart, brain, bone marrow, blood, and other tissues. The analysis and comparison of expression levels, such as by the determination of .beta.-gal activity in the different tissues, will reveal the regulatory pattern of the synthetic regulatory regions in the organism. Expression in one tissue at a significantly higher level than in other tissues indicates that the regulatory regions on the plasmid a specific for that tissue.

Such in vivo analysis of tissue specific expression is applicable to the evaluation of regulatory regions in any position with respect to the coding sequences, such as in the 5' UTR, the 3' UTR, and in introns.

B. Somatic Gene Transfer to Skeletal Muscle In Vivo

To demonstrate the effects of the synthetic elements as used in in vivo gene therapy and/or to identify elements having muscle specific activity, vectors can be injected into adult muscle (e.g., avian or mammalian) for the expression of a reporter gene such as the gene encoding β-gal or luciferase.

Vectors carrying β-gal under the control of the synthetic elements, or under the control of known regulatory regions (used as controls), are pelleted by centrifugation, dried under vacuum, resuspended in an appropriate formulation, and injected into the quadriceps muscle (20 μg/pellet-3 pellets/muscle) of 2 sets of 6 mice (injection into other muscles can also be used). The animal is sacrificed 48 hours following introduction of the DNA and the entire muscle (the muscle injected) from each animal that received an inoculation is removed and assayed for .beta.-gal activity in the tissue. If sufficient experimental animals are available, it is preferable to assay for expression at a number of different time points, such as 24 hrs, 48 hrs, 7 days, 14 days, and 28 days following DNA introduction. In this way additional information is provided on the time course of expression of the reporter gene.

As described above, expression of the reporter gene is determined by assay for activity of the product of that gene, e.g., β-gal activity, however, other methods can also be used, including reverse transcriptase PCR analysis.

Muscle specific expression is demonstrated by showing that expression occurs only or at a significantly higher level in muscle than in other tissues. Therefore, the evaluation preferably also includes assaying for expression of the reporter gene in tissues other than skeletal muscle. It is expected that some amount of the injected vector will migrate to other tissues. Thus, at each of the time points for which muscle samples are taken, samples can also be taken from a set of other tissues, such as gonad, lymph nodes, liver, spleen, kidney, lungs, heart, brain, bone marrow, and blood. Each of the samples is assayed for reporter gene expression.

The pattern of reporter gene expression can also be correlated with the presence of the vector. The presence of the vector in a tissue can be determined by amplification and hybridization of a vector-specific sequence.

Example 5

The Development of Synthetic Regulatory Regions

The above examples describe approaches to constructing, screening, and evaluating synthetic regulatory regions. The combination of these approaches can identify regulatory regions with advantageous properties for particular applications. The following example demonstrates that synthetic regulatory regions constructed using binding sequences in a combinatorial approach can be identified which provide advantageous expression characteristics in a particular tissue and state of that tissue.

To aid in understanding the results of this example, a short background discussion may be of assistance. IGF-1 plays a role as a neurotrophic agent in repairing crushed motor neurons. Localized expression of IGF-I hastens the repair of crushed motor neurons. Although it is one of the strongest muscle specific promoters, skeletal α-actin promoter is not an ideal regulatory region for this expression as intact innervation of muscle is required to maintain skeletal α-actin promoter activity at a high level. In transgenic mice having α-actin/hIGF-1 transgene and showing high level expression of hIGF-1, following sciatic nerve crush the expression level of hIGF-1 was down regulated. hIGF-1 expression was at a minimum about 2 weeks post crush (matching the time of greatest muscle atrophy), and only began to return to normal levels at about 3 weeks post crush.

Thus, nerve crush effectively represses skeletal α-actin promoter, which only recovers with reinnervation. This is in accord with observations that injected α-actin/IGF-1 plasmids take at least three weeks to show effectiveness. Earlier expression of IGF-1 would therefore be desirable in order to maintain high level expression of neurotrophic genes during the early stages of nerve and muscle regeneration.

It is, therefore, beneficial to develop synthetic myogenic regulatory regions to drive IGF-I expression which are insensitive to the innervation state of muscle. Thus, having a myogenic regulatory region that is turned on all the time in muscle should even further speed the nerve repair process. In order to develop such a regulatory region, we took the following steps.

A. Construction of Libraries of Synthetic Regulatory Regions

We first constructed a series of synthetic regulatory regions based on the sequences of transcriptional control elements involved in the activation and regulation of genes in mammalian cells.

The portion of the skeletal α-actin promoter upstream of the ATAAAA box was removed from plasmid p612aACATMLC (which contains a pBluescript polylinker upstream of a skeletal α-actin promoter) by digestion with EagI, which cuts in the pBluescript polylinker upstream of the promoter and 47 bp upstream of the ATAAAA box. The luciferase gene was linked downstream of the resulting minimal α-actin promoter. The synthetic regulatory regions were randomly cloned into this minimal α-actin/luciferase test plasmid.

The control elements that were tested include:

```
SRE     5'-GACACCCAAATATGGCGACGG-3'   (SEQ ID NO:  8)
        3'-CTGTGGGTTTATACCGCTGCC-5'   (SEQ ID NO:  9)
                     *****
MEF-1   5'-CCAACACCTGCTGCCTGCC-3'     (SEQ ID NO: 10)
        3'-GGTTGTGGACGACGGACGG-5'     (SEQ ID NO: 11)

MEF-2   5'-CGCTCTAAAAATAACTCCC-3'     (SEQ ID NO: 12)
        3'-GCGAGATTTTTATTGAGGG-5'     (SEQ ID NO: 13)

TEF-1   5'-CACCATTCCTCAC-3'           (SEQ ID NO: 14)
        3'-GTGGTAAGGAGTG-5'           (SEQ ID NO: 15)

SP1     5'-CCGTCCGCCCTCGG-3'          (SEQ ID NO: 16)
        3'-GGCAGGCGGGAGCC-5'          (SEQ ID NO: 17)
```

The SRE sequence corresponds to the proximal skeletal α-actin SRE sequence. The SRE core sequence, CCCAAATATGG (SEQ ID NO: 55), is overlined. The MEF-1 core sequence (complemented and overlined, CACCTG, SEQ ID NO: 56) and the adjacent GCTGC motif (SEQ ID NO: 57, asterisked) are conserved in the muscle creatine kinase gene and rat myosin light chain gene (Lasser et al., 1989). The MEF-2 core sequence, CTAAAAATAACTC, SEQ ID NO: 58, is overlined. The TEF-1 core sequence, CATTCCT, SEQ ID NO: 59, is overlined. The SP1 sequence (core sequence CCGCCC, SEQ ID NO: 60, overlined) has an EagI half restriction site at each end. Sp1 sites were included as spacers between the other control elements.

Oligonucleotide pairs (dsDNA) were annealed and then ligated together in various combinations to form larger fragments of randomly oriented control elements. Since each of the Sp1 elements contains EagI half-sites at each end, an intact EagI restriction site will be generated wherever two Sp1 elements are ligated together. DNA fragments contain from 8 to 14 control elements in random combinations with EagI cohesive ends, and thus represent synthetic regulatory regions. Fragments formed from each of the combinations of elements resulted in a separate pool of fragments. Each of the combinations contains a heterogenous set of fragments resulting from the particular starting combination of oligonucleotides, as the oligonucleotides can anneal together in various orders and numbers.

DNA fragments from each pool of synthetic regulatory regions was ligated into the EagI site of the minimal α-actin/luciferase plasmid. Approximately twenty clones were picked for each combination, which were then grown, purified with Qiagen kits and used to transfect primary myoblasts.

Figure 5:
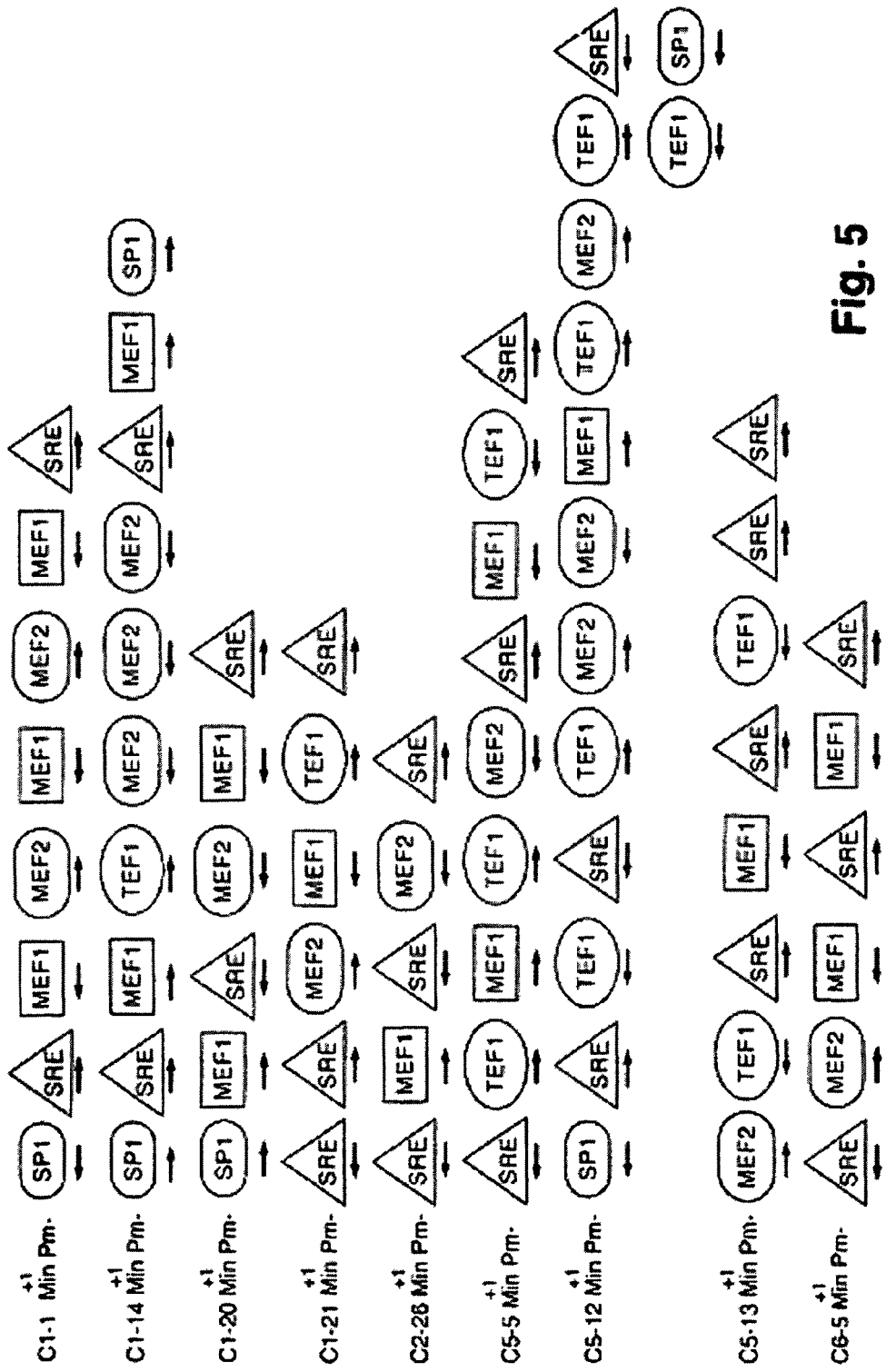
FIG. 5 shows the arrangement of sub-elements of some exemplary synthetic regulatory regions.

The clones were named Cm-n, where m is the number of a particular combination and n is the number of a particular clone picked from that combination. For example, C5-1 represents clone number 1 of combination number 5. FIG. 5 shows the arrangement of sub-elements of some exemplary synthetic regulatory regions. The sequences of portions of the plasmids containing exemplary synthetic regulatory regions, including the sequence of the synthetic regulatory region, are shown in FIGS. 8-31. The sequences are believed to be correct, however a small percentage of sequence errors may be present. One skilled in the art could readily obtain the correct synthetic regulatory region by identifying the particular elements and their positions in the region from the sequence provided, and constructing the synthetic regulatory regions from those elements in the same positions and orientations.

A p448 Sk α-actin promoter/luciferase vector was used as a control. This promoter is a standard representative of strong muscle specific promoters, being one of the strongest such promoters currently available. Expression from this vector was used as a standard for comparison of the expression levels regulated by the test synthetic regulatory regions.

B. Screening of Library of Synthetic Regulatory Regions In Vitro

Plasmids of the synthetic regulatory region library described in A. were transfected into muscle cells with lipofectamine transfections in two series. The transfected cells from these transfection series were grown and collected for luciferase activity assay.

We observed from the first series of lipofectamine transfections done in duplicate in primary myoblast cultures, that none of the eight constructions grown for each of the multimerized SREs, E-boxes, MEF-2, and TEF-1 regulatory regions (32 separate plasmids) had activity greater or equal to the activity of the skeletal .alpha.-actin promoter/enhancer driven luciferase plasmid (p448).

In the second series, six different combinations of synthetic regulatory regions were then tested in mature myotubes. Luciferase activities up to 5-fold greater than that driven by the skeletal α-actin promoter/enhancer were detected by transfections in a subset of clones, namely C1-28 (FIG. 8), C2-27 (FIG. 9), C5-12 (FIG. 10), C6-16 (FIG. 11) and C6'-7 (FIG. 12). In muscle cells, therefore, these synthetic regulatory regions stimulate higher transcription levels than skeletal α-actin promoter.

Moreover, we used a simple assay to check the effect of myoblast depolarization as a way to evaluate the potential for innervation effects on muscle gene expression. We found that the skeletal α-actin promoter is up-regulated 3-4 fold by applying KCl for 20 minutes to the media of myotube cultures. Clones C1-28 (FIG. 8), C5-1 (FIG. 13), C5-5 (FIG. 14), C6-5 (FIG. 15), C5-12 (FIG. 10), C6-16 (FIG. 11), and C6'-7 (FIG. 12) provided high levels of rather stable expression in depolarized myotubes. Thus, these synthetic regulatory regions may be much less affected by innervation effects than skeletal α-actin promoter and are ready for further evaluation.

Figure 6:
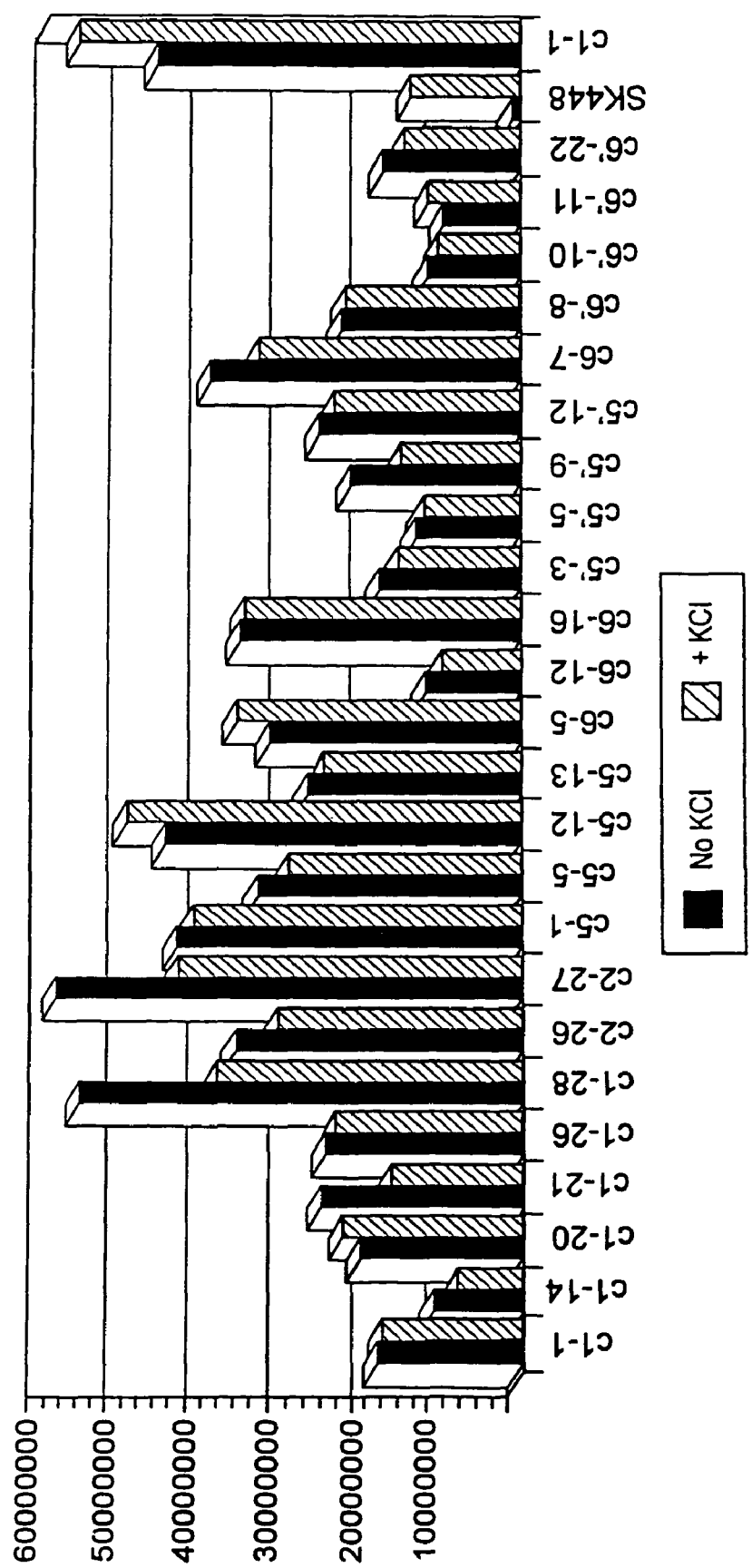
FIG. 6 is a bar graph showing the expression levels in myotubes of the luciferase reporter gene driven by various synthetic regulatory regions in comparison to the expression driven by the skeletal α-actin promoter, and the expression level of each of the synthetic regulatory regions in the presence of KCl depolarization.

Results of the reporter expression levels and of the expression levels in the KCl depolarization test are shown in FIG. 6.

Method

A. First Transfection

1 μg synthetic regulatory region/luciferase plasmid was transfected into 24 hr primary chick myoblast in 60 mm plates (500,000 cells/plate). 200 ng CMV β-gal plasmid was cotransfected in each transfection.

40 hours after transfection, KCl was added directly to the medium to a concentration of 50 μM and cells were treated at 37° C. for 2 hours. The medium containing KCl was aspirated, the cells rinsed once with HBSS, and fresh medium was added. The control plates without KCl treatment were left untouched in the original medium.

20 hours after KCL treatment, cells were collected and luciferase activity was assayed.

B. Second Transfection 100 ng synthetic regulatory region-luciferase plasmid, along with 200 ng CMV β-gal plasmid was transfected to 24-hour primary chick myoblast in 60 mm plates (500,000 cells/plate). 700 ng YEAST MARKER carrier DNA was added to each transfection to make the total amount of DNA transfected 1 μg.

36 hours after transfection, cells were rinsed once with HBSS, MEM (no serum) containing 50 μM KCl (for control) was added, and the cells were incubated at 37° C. for 40 minutes. Then the above medium was aspirated, the cells rinsed once with HBSS, and full medium was added.

24 hours after KCl treatment, cells were collected, and luciferase activity was assayed.

C. Evaluation of Synthetic Regulatory Regions in Nerve Crush Model

To demonstrate the evaluation and identification of synthetic regulatory regions effective in a specific in vivo environment, we tested some of the constructs from above which were shown to provide high level myogenic expression and for which the in vitro test suggested less sensitivity to innervation effects than the Sk α-actin promoter/enhancer. Results for two of the constructs in a nerve crush model are described.

Experiments were designed to test synthetic regulatory regions that are resistant to nerve-injury induced down-regulation of expression driven by skeletal actin promoter.

Figure 7:
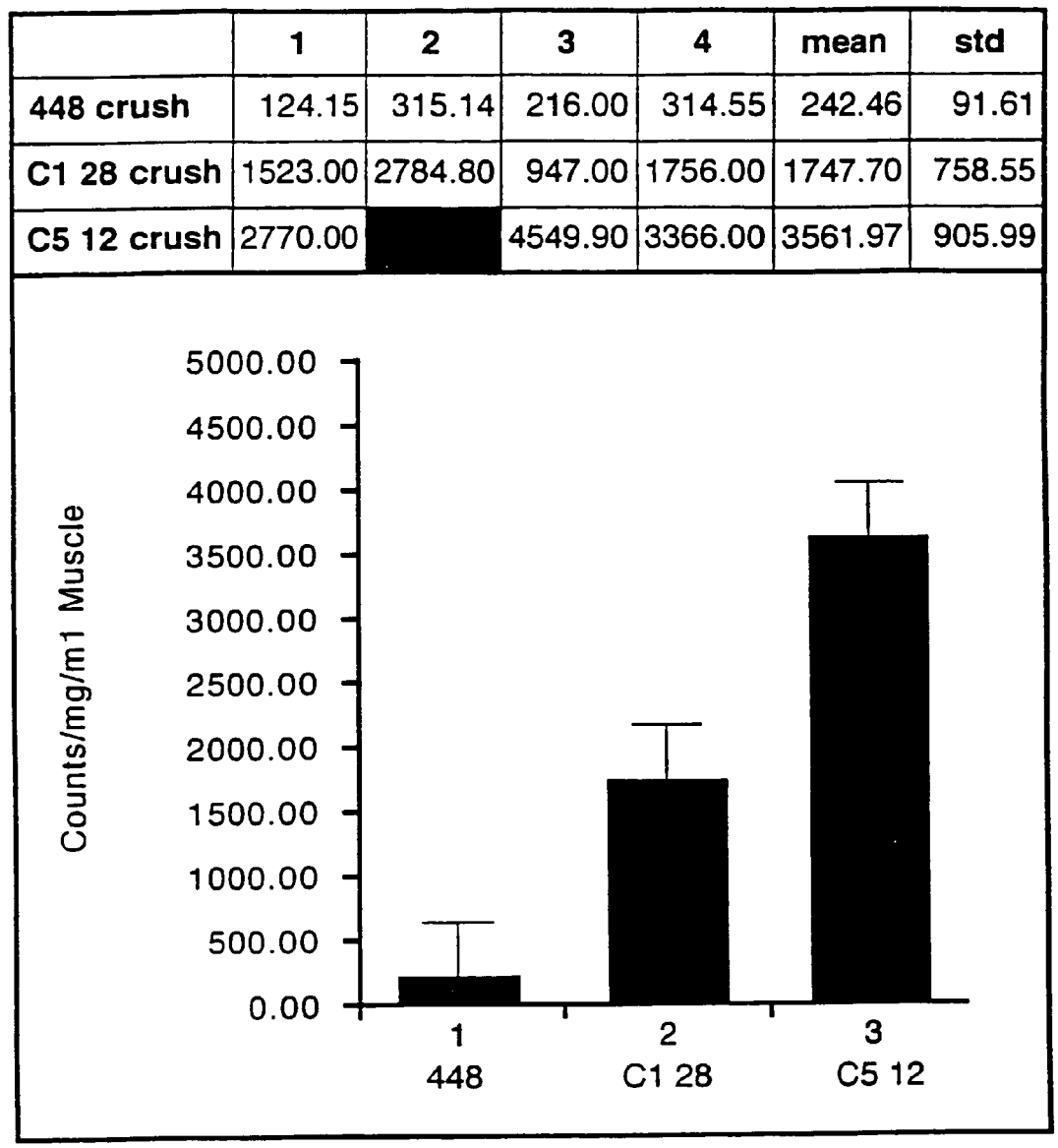
FIG. 7 shows the activities of exemplary regulatory regions under the nerve-injury induced down-regulation of skeletal actin. Tibialis muscle of ICR mice were injected with 100 µg of clone skeletal α-actin promoter 448 (control), synthetic regulatory region C1-28, and C5-12 luciferase vectors. Two weeks post sciatic nerve crush, the muscle was harvested and assayed for luciferase reporter gene activity.
Figure 10B:
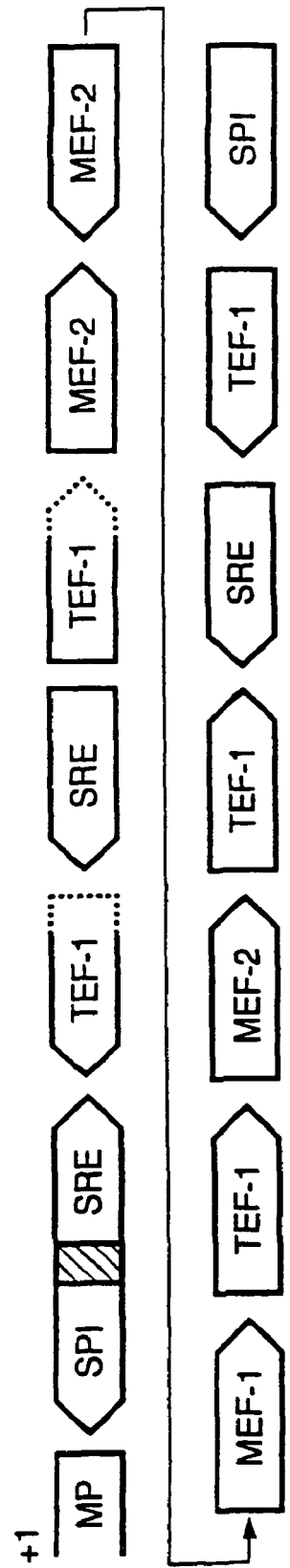
FIG. 10A (SEQ ID NO: 22) & B (SEQ ID NO: 23) show two independently determined sequences of portions of the plasmid containing the synthetic regulatory region of clone C5-12, including the sequence of the synthetic regulatory region insert.
Figure 17B:
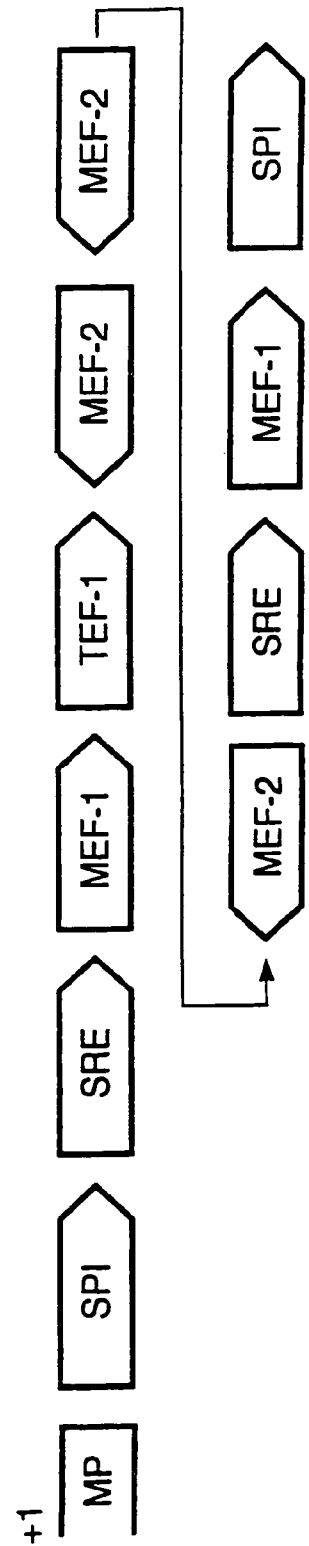
FIG. 17A (SEQ ID NO: 35) & B (SEQ ID NO: 36) show two independently determined sequences of portions of the plasmid containing the synthetic regulatory region of clone C1-14, including the sequence of the synthetic regulatory region insert.
Figure 19:
FIG. 19 shows the sequence of a portion of the plasmid containing the synthetic regulatory region of clone C1-21, including the sequence of the synthetic regulatory region insert (SEQ ID NO: 38).
Figure 22B:
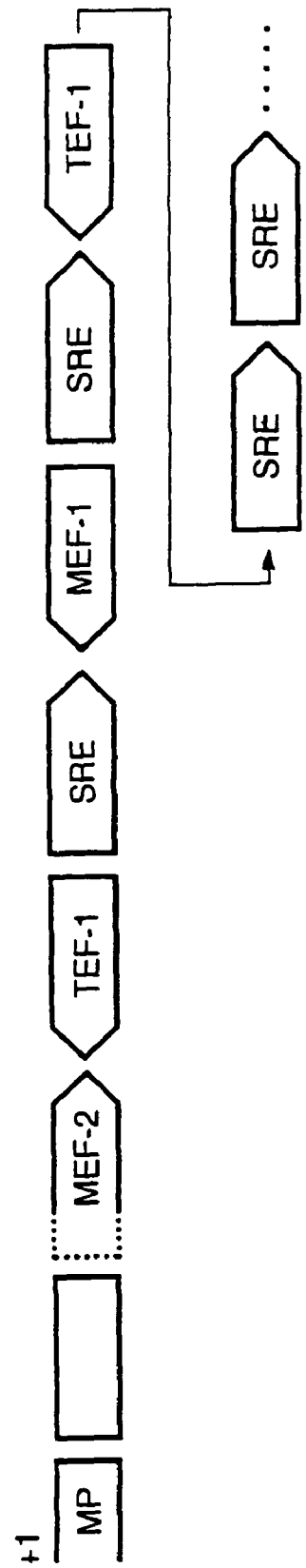
FIG. 22A (SEQ ID NO: 43) & B (SEQ ID NO: 44) show two independently determined sequences of portions of the plasmid containing the synthetic regulatory region of clone C5-13, including the sequence of the synthetic regulatory region insert.

Tibialis muscles of ICR mice were injected with 100 μg of clone skeletal α-actin promoter 448 (control), synthetic regulatory region luciferase vectors C1-28 (FIG. 6), and C5-12 (FIG. 8), which had been shown to be less affected by myoblast depolarization effect than the control (see Section B.). Two weeks post sciatic nerve crush, the injected muscle was harvested and assayed for luciferase activity. The expression levels from C1-28 and C5-12 were approximately 7-fold and 15-fold greater respectively than from the skeletal α-actin promoter (FIG. 7).

These results demonstrate that the two new regulatory regions were more resistant to injury induced regulation. A benefit of these regulatory regions will be to sustain high expression levels of neurotrophic genes during the initial stages of nerve and muscle regeneration, when skeletal α-actin promoter is down-regulated. The higher expression levels provided by synthetic regulatory regions such as these may allow the use of significantly lower amounts of DNA, e.g., {fraction (1/10)} the amount of DNA, to achieve the same biological effects as that provided by expression driven by promoters such as the skeletal α-actin promoter.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Other embodiments are within the following claims.

We claim:

1. A muscle specific promoter comprising a synthetic regulatory region comprising an arrangement of at least three different transcription factor binding sites selected from the group consisting of SRE, MEF-1, MEF-2, TEF-1, Sp1, and combinations thereof.

2. The muscle specific promoter of claim 1, wherein the synthetic regulatory region comprises at least one copy of SRE, MEF-1, and MEF-2.

3. The muscle specific promoter of claim 2, further comprising at least one copy of TEF1.

4. The muscle specific promoter of claim 2, further comprising at least one copy of Sp1.

* * * * *

```
SEQUENCE LISTING

<160> NUMBER OF SEQ ID NOS: 56

<210> SEQ ID NO 1
<211> LENGTH: 16
<212> TYPE: DNA
<213> ORGANISM: Artificial Sequence
<220> FEATURE:
<223> OTHER INFORMATION: Binding site for transcription factor MEF-2

<400> SEQUENCE: 1
ctctaaaaat aactcc                                                    16

<210> SEQ ID NO 2
<211> LENGTH: 22
<212> TYPE: DNA
<213> ORGANISM: Artificial Sequence
<220> FEATURE:
<223> OTHER INFORMATION: MRE (muscle response element)

<400> SEQUENCE: 2
gcccaacacc caaatatggc tt                                             22

<210> SEQ ID NO 3
<211> LENGTH: 11
<212> TYPE: DNA
<213> ORGANISM: Artificial Sequence
<220> FEATURE:
<223> OTHER INFORMATION: E-box binding site recognized by basic-helix-
      loop-helix (bHLH) transcription factors.

<400> SEQUENCE: 3
ctcacctgct g                                                         11

<210> SEQ ID NO 4
<211> LENGTH: 14
<212> TYPE: DNA
<213> ORGANISM: Artificial Sequence
<220> FEATURE:
<223> OTHER INFORMATION: Binding site for transcription factor TEF-1

<400> SEQUENCE: 4
gccgcattcc tggg                                                      14

<210> SEQ ID NO 5
<211> LENGTH: 8
<212> TYPE: DNA
<213> ORGANISM: Artificial Sequence
<220> FEATURE:
<223> OTHER INFORMATION: Binding site for transcription factor Sp1

<400> SEQUENCE: 5 ccccgccc                                                              8

<210> SEQ ID NO 6
<211> LENGTH: 28
<212> TYPE: DNA
<213> ORGANISM: Artificial Sequence
```

```
<220> FEATURE:
<223> OTHER INFORMATION: C-FOS SRE

<400> SEQUENCE: 6
acaggatgtc catattagga catctgcg                                              28

<210> SEQ ID NO 7
<211> LENGTH: 28
<212> TYPE: DNA
<213> ORGANISM: Artificial Sequence
<220> FEATURE:
<223> OTHER INFORMATION: MUSCLE SRE

<400> SEQUENCE: 7
gcccgacacc caaatatggc gacggccg                                              28

<210> SEQ ID NO 8
<211> LENGTH: 21
<212> TYPE: DNA
<213> ORGANISM: Artificial Sequence
<220> FEATURE:
<223> OTHER INFORMATION: SRE 5' to 3'

<400> SEQUENCE: 8
gacacccaaa tatggcgacg g                                                     21

<210> SEQ ID NO 9
<211> LENGTH: 21
<212> TYPE: DNA
<213> ORGANISM: Artificial Sequence
<220> FEATURE:
<223> OTHER INFORMATION: SRE 3' to 5'

<400> SEQUENCE: 9
ccgtcgccat atttgggtgt c                                                     21

<210> SEQ ID NO 10
<211> LENGTH: 19
<212> TYPE: DNA
<213> ORGANISM: Artificial Sequence
<220> FEATURE:
<223> OTHER INFORMATION: MEF-1 5' to 3'

<400> SEQUENCE: 10
ccaacacctg ctgcctgcc                                                        19

<210> SEQ ID NO 11
<211> LENGTH: 19
<212> TYPE: DNA
<213> ORGANISM: Artificial Sequence
<220> FEATURE:
<223> OTHER INFORMATION: MEF-1 3' to 5'

<400> SEQUENCE: 11
ggcaggcagc aggtgttgg                                                        19

<210> SEQ ID NO 12
<211> LENGTH: 19
<212> TYPE: DNA
<213> ORGANISM: Artificial Sequence
<220> FEATURE:
<223> OTHER INFORMATION: MEF-2 5' to 3'

<400> SEQUENCE: 12
cgctctaaaa ataactccc                                                        19
```

```
<210> SEQ ID NO 13
<211> LENGTH: 19
<212> TYPE: DNA
<213> ORGANISM: Artificial Sequence
<220> FEATURE:
<223> OTHER INFORMATION: MEF-2 3' to 5'

<400> SEQUENCE: 13
gggagttatt tttagagcg                                                19

<210> SEQ ID NO 14
<211> LENGTH: 13
<212> TYPE: DNA
<213> ORGANISM: Artificial Sequence
<220> FEATURE:
<223> OTHER INFORMATION: TEF-1 5' to 3'

<400> SEQUENCE: 14
caccattcct cac                                                      13

<210> SEQ ID NO 15
<211> LENGTH: 13
<212> TYPE: DNA
<213> ORGANISM: Artificial Sequence
<220> FEATURE:
<223> OTHER INFORMATION: TEF-1 3' to 5'

<400> SEQUENCE: 15
gtgaggaatg gtg                                                      13

<210> SEQ ID NO 16
<211> LENGTH: 14
<212> TYPE: DNA
<213> ORGANISM: Artificial Sequence
<220> FEATURE:
<223> OTHER INFORMATION: SP1 5' to 3'

<400> SEQUENCE: 16
ccgtccgccc tcgg                                                     14

<210> SEQ ID NO 17
<211> LENGTH: 14
<212> TYPE: DNA
<213> ORGANISM: Artificial Sequence
<220> FEATURE:
<223> OTHER INFORMATION: SP1 3' to 5'

<400> SEQUENCE: 17
ccgagggcgg acgg                                                     14

<210> SEQ ID NO 18
<211> LENGTH: 22
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (1)..(18)
<223> OTHER INFORMATION: "n" stands for a, g, c or t
<220> FEATURE:
<221> NAME/KEY: misc_feature
<222> LOCATION: (1)..(22)
<223> OTHER INFORMATION: "n" stands for a, g, c or t

<400> SEQUENCE: 18 nnnnnnnnn nnnnnnnnn nn                                              22
```

<210> SEQ ID NO 19
<211> LENGTH: 550
<212> TYPE: DNA
<213> ORGANISM: Artificial Sequence
<220> FEATURE:
<223> OTHER INFORMATION: DNA SIS 4573-6g portion of the plasmid
      containing the synthetic regulatory region of clone C1-28,
      including the sequence of the synthetic regulatory region insert.
<220> FEATURE:
<221> NAME/KEY: misc_feature
<222> LOCATION: (208)..(208)
<223> OTHER INFORMATION: "n" stands for a, g, c or t
<220> FEATURE:
<221> NAME/KEY: misc_feature
<222> LOCATION: (503)..(503)
<223> OTHER INFORMATION: "n" stands for a, g, c or t
<220> FEATURE:
<221> NAME/KEY: misc_feature
<222> LOCATION: (533)..(533)
<223> OTHER INFORMATION: "n" stands for a, g, c or t
<220> FEATURE:
<221> NAME/KEY: misc_feature
<222> LOCATION: (548)..(548)
<223> OTHER INFORMATION: "n" stands for a, g, c or t

<400> SEQUENCE: 19
attttacaac agtaccggaa tgccaagctt gatatcgaat tcctgcagcc cggggatcc      60 actagttcta gagcttggcg cctcccgctc ctccgggtag ctcgtgggcc gccgccggcc     120
ccggagcctt ttatcgaggc gggcgggagc accgccggc ccccaggaat gcggccccgg     180
ccgtccgccc tcgggagtta ttttagancg gtgaggaatg gtgccaacac ctgctgcctg     240
ccccgtcgcc atatttgggt gtcgtgagga atggtgccgt cgccatattt ccgtcgccat     300
atttgggtgt ccaccattcc tcaccgctct aaaaataact cccgggagtt attttttagag    360 cgccgtcgcc atatttgggt gtcgtgagga atggtgcacc attcctcacc gctctaaaaa     420
taactccccc aacacctgct gcctgcccgc tctaaaataa ctcccgacac ccaaatatgg     480
cgacggccgc caccgcggtg ganctcggta cctcccgggt tatgttaact canttacagt     540 accataanat                                                            550

<210> SEQ ID NO 20
<211> LENGTH: 600
<212> TYPE: DNA
<213> ORGANISM: Artificial Sequence
<220> FEATURE:
<223> OTHER INFORMATION: DNA SIS 4573-8g portion of the plasmid
      containing the synthetic regulatory region of clone C2-27,
      including the sequence of the synthetic regulatory region insert
<220> FEATURE:
<221> NAME/KEY: misc_feature
<222> LOCATION: (15)..(15)
<223> OTHER INFORMATION: "n" stands for a, g, c or t
<220> FEATURE:
<221> NAME/KEY: misc_feature
<222> LOCATION: (20)..(20)
<223> OTHER INFORMATION: "n" stands for a, g, c or t
<220> FEATURE:
<221> NAME/KEY: misc_feature
<222> LOCATION: (355)..(355)
<223> OTHER INFORMATION: "n" stands for a, g, c or t
<220> FEATURE:
<221> NAME/KEY: misc_feature
<222> LOCATION: (388)..(388)
<223> OTHER INFORMATION: "n" stands for a, g, c or t
<220> FEATURE:
<221> NAME/KEY: misc_feature
<222> LOCATION: (518)..(518)
<223> OTHER INFORMATION: "n" stands for a, g, c or t

<400> SEQUENCE: 20
attttacaac ttcgngagan tgccaagctt gatatcgaat tcctgcagcc cggggatcc      60

```
actagttcta gagcttggcg cctcccgctc ctccgggtag ctcgtgggcc gccgccggcc      120
ccggagcctt ttatcgaggc gggcgggagc accgcccggc cccaggaat  gcggccccgg      180 ccgtcgccat atttgggtgt cccaacactg ctgcctgccg acacccaaat atggcgacgg      240
gtgaggaatg gtgccaacac ctgctgcctg ccgacaccca aatatggcga cggccgccac      300
cgcggtggag ctcggtacct cccgggttat gttagctcag ttacagtacc ataanataca      360
ttgatgagtt tggacaaacc acaactanaa tgcagtgaaa aaaatgcttt atttgtgaaa      420
tttgtgatgc tattgcttta tttgtaacca ttataagctg caataaacaa gttaacaaca      480
acaattgcat tcattttatg tttcaagttc aggggangt  gtgggaagtt ttttaaagca      540
agtaaaacct ccacgtacct taatattact tacttatcat ggtacttggg ctggcgtaat      600
```

<210> SEQ ID NO 21
<211> LENGTH: 500
<212> TYPE: DNA
<213> ORGANISM: Artificial Sequence
<220> FEATURE:
<223> OTHER INFORMATION: BCM17.CP1 portion of the plasmid containing the
      synthetic regulatory region of clone C2-27, including the sequence
      of the synthetic regulatory region insert

<400> SEQUENCE: 21

```
aatgccaagc ttgatatcga attcctgcag cccgggggat ccactagttc tagagcttgg       60
cgcctcccgc tcctccgggt agctcgtggg ccgccgccgg ccccggagcc ttttatcgag      120
gcgggcggga gcaccgcccg gccccaggaa atgcggcccc ggccgtcgcc atatttgggt      180
gtcccaacac tgctgcctgc cgacacccaa atatggcgac gggtgaggaa tggtgccaac      240
acctgctgcc tgccgacacc caaatatggc gacggccgcc accgcggtgg agctcggtac      300
ctcccgggtt atgttagctc agttacagta ccataagata cattgatgag tttggacaaa      360
ccacaactag aatgcagtga aaaaaatgct ttatttgtga aatttgtgat gctattgctt      420
tattttgtaa ccattataac tgcaataaac aatttaacaa caacaattgc attccatttt      480 attttttcaag ttcaagggga                                                500
```

<210> SEQ ID NO 22
<211> LENGTH: 550
<212> TYPE: DNA
<213> ORGANISM: Artificial Sequence
<220> FEATURE:
<223> OTHER INFORMATION: DNA SIS 4573-12g portion of the plasmid
      containing the synthetic regulatory region of clone C5-12,
      including the sequence of the synthetic regulatory region insert
<220> FEATURE:
<221> NAME/KEY: misc_feature
<222> LOCATION: (414)..(414)
<223> OTHER INFORMATION: "n" stands for a, g, c or t
<220> FEATURE:
<221> NAME/KEY: misc_feature
<222> LOCATION: (439)..(439)
<223> OTHER INFORMATION: "n" stands for a, g, c or t
<220> FEATURE:
<221> NAME/KEY: misc_feature
<222> LOCATION: (444)..(444)
<223> OTHER INFORMATION: "n" stands for a, g, c or t
<220> FEATURE:
<221> NAME/KEY: misc_feature
<222> LOCATION: (450)..(450)
<223> OTHER INFORMATION: "n" stands for a, g, c or t
<220> FEATURE:
<221> NAME/KEY: misc_feature
<222> LOCATION: (459)..(459)
<223> OTHER INFORMATION: "n" stands for a, g, c or t
<220> FEATURE:
<221> NAME/KEY: misc_feature

```
<222> LOCATION: (492)..(492)
<223> OTHER INFORMATION: "n" stands for a, g, c or t
<220> FEATURE:
<221> NAME/KEY: misc_feature
<222> LOCATION: (520)..(520)
<223> OTHER INFORMATION: "n" stands for a, g, c or t
<220> FEATURE:
<221> NAME/KEY: misc_feature
<222> LOCATION: (529)..(529)
<223> OTHER INFORMATION: "n" stands for a, g, c or t

<400> SEQUENCE: 22
attttacaac agtacggaat gccaagcttg atatcgaatt cctgcagccc gggggatcca      60
ctagttctag agcttggcgc ctcccgctcc tccgggtagc tcgtgggccg ccgccggccc     120
cggagccttt tatcgaggcg ggcgggagca ccgcccggcc cccaggaatg cggccccggc     180
cgagggcgga cacccaaata tggcgacggg tgaggaaccg tcgccatatt tgggtgtcca     240
ccattcctcc gctctaaaaa taactcccgg gagttatttt taaagcgcca acacctgctg     300
cctgcccacc ttcctcaccg ctctaaaaat aactccccac cattcctcac ccgtcgccat     360
atttgggtgt cgtgaggatg gtgccgaagg cggacggccg ccaccgcggt gganctcggt     420
acctcccggg ttatgttanc tcanttacan taccataana tacattgatg aatttggaca     480
aaccacaact anaatgcatg aaaaaaatgc tttatttgtn aaatttgtna tgctattgct     540
ttatttgtta                                                           550

<210> SEQ ID NO 23
<211> LENGTH: 446
<212> TYPE: DNA
<213> ORGANISM: Artificial Sequence
<220> FEATURE:
<223> OTHER INFORMATION: BCM12.CP1 portion of the plasmid containing the
      synthetic regulatory region of clone C5-12, including the sequence
      of the synthetic regulatory region insert
<220> FEATURE:
<221> NAME/KEY: misc_feature
<222> LOCATION: (9)..(10)
<223> OTHER INFORMATION: "n" stands for a, g, c or t
<220> FEATURE:
<221> NAME/KEY: misc_feature
<222> LOCATION: (14)..(14)
<223> OTHER INFORMATION: "n" stands for a, g, c or t
<220> FEATURE:
<221> NAME/KEY: misc_feature
<222> LOCATION: (34)..(35)
<223> OTHER INFORMATION: "n" stands for a, g, c or t
<220> FEATURE:
<221> NAME/KEY: misc_feature
<222> LOCATION: (106)..(106)
<223> OTHER INFORMATION: "n" stands for a, g, c or t
<220> FEATURE:
<221> NAME/KEY: misc_feature
<222> LOCATION: (143)..(143)
<223> OTHER INFORMATION: "n" stands for a, g, c or t

<400> SEQUENCE: 23
gatatcgann tcgngcagcc cggggatcc actnnttcta gagcttggcg cctcccgctc      60
ctccgggtag ctcgtgggcc gccgccggcc ccggagcctt ttatcnaggc gggcgggagc     120
accgcccggc cccacgaat gcngcccggg ccgagggcgg acacccaaat atggcgacgg      180
gtgaggaacc gtcgccatat ttgggtgtcc accattcctc cgctctaaaa ataactcccg     240
ggagttattt ttagagcgcc aacacctgct gcctgcccac cttcctcacc gctctaaaaa     300
taactcccca ccattcctca cccgtcgcca tatttgggtg tcgtgaggat ggtgccgagg     360
gcggacggcc gccaccgcgg tggagctcgg tacctcccgg gttatgttag ctcagttaca     420
gtaccataag atacattgat gagttt                                         446
```

<210> SEQ ID NO 24
<211> LENGTH: 550
<212> TYPE: DNA
<213> ORGANISM: Artificial Sequence
<220> FEATURE:
<223> OTHER INFORMATION: DNA SIS 4573-16g portion of the plasmid
      containing the synthetic regulatory region of clone C6-16,
      including the sequence of the synthetic regulatory region insert
<220> FEATURE:
<221> NAME/KEY: misc_feature
<222> LOCATION: (442)..(442)
<223> OTHER INFORMATION: "n" stands for a, g, c or t

<400> SEQUENCE: 24

```
attttaccaa cagtaccgga atgccaagct tgatatcgaa ttcctgcagc ccgggggatc    60
cactagttct agagcttggc gcctcccgct cctccgggta gctcgtgggc cgccgccggc   120
cccggagcct tttatcgagg cgggcgggag caccgcccgg cccccaggaa tgcggccccg   180
gccgagggcg gacaccaaat atggcgacgg ggcaggcagc aggtgttggg gcaggcagca   240
ggtgttggcc aacacctgct gcctgccgac acccaaatat ggcgacgggg caggcagcag   300
gtgttggggg agttattttt agagcggaca cccaaatatg cgcgacggccg ccaccgcggt   360
ggagctcggt acctcccggg ttatgttagc tcagttacag taccataaga tacattgatg   420
agtttggaca aaccacaact anaatgcagt tgaaaaaaat gctttatttg tgaaatttgt   480
gatgctattg ctttatttgt aaccattata agctgcaata aacaatttaa caacaacaat   540
tgcattccat                                                          550
```

<210> SEQ ID NO 25
<211> LENGTH: 501
<212> TYPE: DNA
<213> ORGANISM: Artificial Sequence
<220> FEATURE:
<223> OTHER INFORMATION: BCM16.CP1 portion of the plasmid containing the
      synthetic regulatory region of clone C6-16, including the sequence
      of the synthetic regulatory region insert
<220> FEATURE:
<221> NAME/KEY: misc_feature
<222> LOCATION: (48)..(48)
<223> OTHER INFORMATION: "n" stands for a, g, c or t
<220> FEATURE:
<221> NAME/KEY: misc_feature
<222> LOCATION: (56)..(56)
<223> OTHER INFORMATION: "n" stands for a, g, c or t
<220> FEATURE:
<221> NAME/KEY: misc_feature
<222> LOCATION: (108)..(108)
<223> OTHER INFORMATION: "n" stands for a, g, c or t
<220> FEATURE:
<221> NAME/KEY: misc_feature
<222> LOCATION: (121)..(121)
<223> OTHER INFORMATION: "n" stands for a, g, c or t
<220> FEATURE:
<221> NAME/KEY: misc_feature
<222> LOCATION: (125)..(125)
<223> OTHER INFORMATION: "n" stands for a, g, c or t
<220> FEATURE:
<221> NAME/KEY: misc_feature
<222> LOCATION: (129)..(129)
<223> OTHER INFORMATION: "n" stands for a, g, c or t
<220> FEATURE:
<221> NAME/KEY: misc_feature
<222> LOCATION: (167)..(167)
<223> OTHER INFORMATION: "n" stands for a, g, c or t
<220> FEATURE:
<221> NAME/KEY: misc_feature
<222> LOCATION: (193)..(193)
<223> OTHER INFORMATION: "n" stands for a, g, c or t
<220> FEATURE:
<221> NAME/KEY: misc_feature

```
<222> LOCATION: (216)..(216)
<223> OTHER INFORMATION: "n" stands for a, g, c or t
<220> FEATURE:
<221> NAME/KEY: misc_feature
<222> LOCATION: (255)..(255)
<223> OTHER INFORMATION: "n" stands for a, g, c or t
<220> FEATURE:
<221> NAME/KEY: misc_feature
<222> LOCATION: (266)..(266)
<223> OTHER INFORMATION: "n" stands for a, g, c or t
<220> FEATURE:
<221> NAME/KEY: misc_feature
<222> LOCATION: (274)..(274)
<223> OTHER INFORMATION: "n" stands for a, g, c or t
<220> FEATURE:
<221> NAME/KEY: misc_feature
<222> LOCATION: (285)..(285)
<223> OTHER INFORMATION: "n" stands for a, g, c or t
<220> FEATURE:
<221> NAME/KEY: misc_feature
<222> LOCATION: (293)..(293)
<223> OTHER INFORMATION: "n" stands for a, g, c or t
<220> FEATURE:
<221> NAME/KEY: misc_feature
<222> LOCATION: (301)..(301)
<223> OTHER INFORMATION: "n" stands for a, g, c or t
<220> FEATURE:
<221> NAME/KEY: misc_feature
<222> LOCATION: (306)..(306)
<223> OTHER INFORMATION: "n" stands for a, g, c or t
<220> FEATURE:
<221> NAME/KEY: misc_feature
<222> LOCATION: (311)..(311)
<223> OTHER INFORMATION: "n" stands for a, g, c or t
<220> FEATURE:
<221> NAME/KEY: misc_feature
<222> LOCATION: (314)..(314)
<223> OTHER INFORMATION: "n" stands for a, g, c or t
<220> FEATURE:
<221> NAME/KEY: misc_feature
<222> LOCATION: (321)..(321)
<223> OTHER INFORMATION: "n" stands for a, g, c or t
<220> FEATURE:
<221> NAME/KEY: misc_feature
<222> LOCATION: (325)..(325)
<223> OTHER INFORMATION: "n" stands for a, g, c or t
<220> FEATURE:
<221> NAME/KEY: misc_feature
<222> LOCATION: (340)..(340)
<223> OTHER INFORMATION: "n" stands for a, g, c or t
<220> FEATURE:
<221> NAME/KEY: misc_feature
<222> LOCATION: (343)..(343)
<223> OTHER INFORMATION: "n" stands for a, g, c or t
<220> FEATURE:
<221> NAME/KEY: misc_feature
<222> LOCATION: (368)..(368)
<223> OTHER INFORMATION: "n" stands for a, g, c or t
<220> FEATURE:
<221> NAME/KEY: misc_feature
<222> LOCATION: (391)..(391)
<223> OTHER INFORMATION: "n" stands for a, g, c or t
<220> FEATURE:
<221> NAME/KEY: misc_feature
<222> LOCATION: (399)..(399)
<223> OTHER INFORMATION: "n" stands for a, g, c or t
<220> FEATURE:
<221> NAME/KEY: misc_feature
<222> LOCATION: (459)..(459)
<223> OTHER INFORMATION: "n" stands for a, g, c or t
<220> FEATURE:
<221> NAME/KEY: misc_feature
<222> LOCATION: (476)..(476)
<223> OTHER INFORMATION: "n" stands for a, g, c or t
<220> FEATURE:
<221> NAME/KEY: misc_feature
<222> LOCATION: (478)..(478)
<223> OTHER INFORMATION: "n" stands for a, g, c or t
<220> FEATURE:
<221> NAME/KEY: misc_feature
```

<222> LOCATION: (483)..(483)
<223> OTHER INFORMATION: "n" stands for a, g, c or t
<220> FEATURE:
<221> NAME/KEY: misc_feature
<222> LOCATION: (489)..(489)
<223> OTHER INFORMATION: "n" stands for a, g, c or t

<400> SEQUENCE: 25

```
gcttgatatc gaattcctgc agcccggggg catccactat ctactagngc ttgacncctc    60
ccgctcctcc gggtagctcg tgggccgccg ccggccccgg acccctatnat cgaagcgggc   120 nggancacng cccggccccc acccaatgca gtcccggccc gagggcncga caccaaaatat  180 gtgtcacagg gcnggcacca ggtgttgggg caagcngcag gtgttttgcca actcctgctg   240 cctgccgaca cccanatatg gccacngggc acgnagcacg tgttngggga gtnattttta    300
nacccnacac ncanatatgg ncacngccgc caccgcggtn ganctcggta actcccgggt    360
tatgttanct caattacagt accataaatat nctttgatna atttggacaa accacaacta   420
taatgcagtg aaaaaaatgc tttatttgtg aaatttgtna tgctattgct tttatntntt    480
aancattana agctccaata a                                             501
```

<210> SEQ ID NO 26
<211> LENGTH: 500
<212> TYPE: DNA
<213> ORGANISM: Artificial Sequence
<220> FEATURE:
<223> OTHER INFORMATION: DNA SIS 4585-1g portion of the plasmid
      containing the synthetic regulatory region of clone C6'-7,
      including the sequence of the synthetic regulatory region insert
<220> FEATURE:
<221> NAME/KEY: misc_feature
<222> LOCATION: (277)..(277)
<223> OTHER INFORMATION: "n" stands for a, g, c or t
<220> FEATURE:
<221> NAME/KEY: misc_feature
<222> LOCATION: (343)..(343)
<223> OTHER INFORMATION: "n" stands for a, g, c or t
<220> FEATURE:
<221> NAME/KEY: misc_feature
<222> LOCATION: (411)..(411)
<223> OTHER INFORMATION: "n" stands for a, g, c or t

<400> SEQUENCE: 26

```
attttacaac agtacggaat gccaagcttg atatcgaatt cctgcagccc ggggggatcca    60 ctagttctag agcttggcgc ctcccgctcc tccgggtagc tcgtgggccg ccgccggccc   120
cggagccttt tatcgaggcg ggcgggagca ccgcccggcc cccaggaatg cggcccccggc  180 cgtccgccct cgggacaccc aaatatggcg acggcgctct aaaaataact ccccccaacac  240 ctgctgcctg ccgacaccca aatatggcaa cggggcnagg cagcaggtgt ttggcgctct   300
aaaaataact ccccccgagg gcggacggcc cgccaccgcg gtnggagctc ggtacctccc   360
gggttatgtt tagctccagt tacagtacca taagatacat tgaatgattt nggacaaacc   420
acaactaaaa atgcaattga aaaaaaatgc tttatttgtt gaaatttgtt gaatgctatt   480
gctttatttt gttaaccatt                                               500
```

<210> SEQ ID NO 27
<211> LENGTH: 198
<212> TYPE: DNA
<213> ORGANISM: Artificial Sequence
<220> FEATURE:
<223> OTHER INFORMATION: DNA SIS 4573-9g portion of the plasmid
      containing the synthetic regulatory region of clone C5-1,
      including the sequence of the synthetic regulatory region insert

<400> SEQUENCE: 27

```
attttacaac agtaccggaa tgccaagctt gatatcgaat tcctgcagcc cgggggatcc      60
actagttcta gagcttggcg cctcccgctc ctccgggtag ctcgtgggcc gccgccggcc     120
ccggagcctt ttatcgaggc gggcgggagc accgcccggc cccaggaat gcggccccgg      180 ccgagggccg acggccga                                                   198
```

<210> SEQ ID NO 28
<211> LENGTH: 175
<212> TYPE: DNA
<213> ORGANISM: Artificial Sequence
<220> FEATURE:
<223> OTHER INFORMATION: BCM10.CP1 portion of the plasmid containing the synthetic regulatory region of clone C5-1, including the sequence of the synthetic regulatory region insert

<400> SEQUENCE: 28

```
aagcttgata tcgaattcct gcagcccggg ggatccacta gttctagagc ttggcgcctc      60
ccgctcctcc gggtagctcg tgggccgccg ccggccccgg agccttttat cgaggcgggc    120
gggagcaccg cccggccccc aggaatgcgg ccccggccga tggcggacgg ccgat         175
```

<210> SEQ ID NO 29
<211> LENGTH: 550
<212> TYPE: DNA
<213> ORGANISM: Artificial Sequence
<220> FEATURE:
<223> OTHER INFORMATION: DNA SIS 4573-10g
<220> FEATURE:
<221> NAME/KEY: misc_feature
<222> LOCATION: (507)..(507)
<223> OTHER INFORMATION: "n" stands for a, g, c or t
<220> FEATURE:
<221> NAME/KEY: misc_feature
<222> LOCATION: (522)..(522)
<223> OTHER INFORMATION: "n" stands for a, g, c or t
<220> FEATURE:
<221> NAME/KEY: misc_feature
<222> LOCATION: (540)..(540)
<223> OTHER INFORMATION: "n" stands for a, g, c or t

<400> SEQUENCE: 29

```
attttacaac agtacggaat gccaagcttg atatcgaatt cctgcagccc ggggaatcc       60 actagttcta gagcttggcg cctcccgctc ctccgggtag ctcgtgggcc gccgccggcc    120
ccggagcctt ttatcgaggc gggcgggagc accgcccggc cccaggaat gcggccccgg     180 ccgtcgccat atttgggtgt ccaccattcc tcaccgctct aaaaataact cccgtgagga    240
atggtgcacc attcctcacc cgtcgccata tttgggtgtc ccgagggcgg acggccgcca    300
ccgcggtgga gctcggtacc tcccgggtta tgttagctca gttacagtac cataagatac    360
attgatgagt ttggacaaac cacaactaga atgcagtgaa aaaaatgctt tatttgtgaa    420
atttgtgatg ctattgcttt atttgtaacc attataagct gcaataaaca agttaacaac    480
aacaattgca ttcattttat gtttcangtt caaggggaag tnttggaagt ttttttaaan    540
caattaaaac                                                           550
```

<210> SEQ ID NO 30
<211> LENGTH: 492
<212> TYPE: DNA
<213> ORGANISM: Artificial Sequence
<220> FEATURE:
<223> OTHER INFORMATION: BCM11.CP1
<220> FEATURE:
<221> NAME/KEY: misc_feature
<222> LOCATION: (271)..(271)
<223> OTHER INFORMATION: "n" stands for a, g, c or t

```
<220> FEATURE:
<221> NAME/KEY: misc_feature
<222> LOCATION: (274)..(274)
<223> OTHER INFORMATION: "n" stands for a, g, c or t
<220> FEATURE:
<221> NAME/KEY: misc_feature
<222> LOCATION: (284)..(284)
<223> OTHER INFORMATION: "n" stands for a, g, c or t
<220> FEATURE:
<221> NAME/KEY: misc_feature
<222> LOCATION: (403)..(403)
<223> OTHER INFORMATION: "n" stands for a, g, c or t
<220> FEATURE:
<221> NAME/KEY: misc_feature
<222> LOCATION: (420)..(420)
<223> OTHER INFORMATION: "n" stands for a, g, c or t
<220> FEATURE:
<221> NAME/KEY: misc_feature
<222> LOCATION: (426)..(426)
<223> OTHER INFORMATION: "n" stands for a, g, c or t

<400> SEQUENCE: 30
aagcttgata tcgaattcct gcagcccggg ggatccacta gttctagagc ttggcgcctc      60
ccgctcctcc gggtagctcg tgggccgccg ccggccccgg agccttttat cgaggcgggc     120
gggagcaccg cccggccccc aggaatgcgg ccccggccgt cgccatattt gggtgtccac     180
cattcctcac ccaacacctg ctgcctgccc accattcctc acgggagtta ttttagagc      240 ggacacccaa atatggcgac ggggcaagca ncangtgttg ggtnaggaat ggtggacacc     300
caaatatggc gacggccggg gccgcattcc tgggggccgg gcgtgctcc cgcccgcctc      360 gataaaagct ccggggccgg cggcggccac gaactacccg gangaacggg aagcgccaan    420
ctctanaact aatggatccc ccgggctgca agaattcgat atcaagcttg gcattccggg    480
tactgttggt aa                                                                    492

<210> SEQ ID NO 31
<211> LENGTH: 200
<212> TYPE: DNA
<213> ORGANISM: Artificial Sequence
<220> FEATURE:
<223> OTHER INFORMATION: DNA SIS 4573-14g

<400> SEQUENCE: 31
attttacaac agtaccggaa tgccaagctt gatatcgaat tcctgcagcc cggggggatcc     60 actagttcta gagcttggcg cctcccgctc ctccgggtag ctcgtgggcc gccgccggcc    120
ccggagcctt ttatcgaggc gggcgggagc accgcccggc ccccaggaat gcggccccgg    180
ccgtcgccat atttgggtgt                                                           200

<210> SEQ ID NO 32
<211> LENGTH: 499
<212> TYPE: DNA
<213> ORGANISM: Artificial Sequence
<220> FEATURE:
<223> OTHER INFORMATION: BCM14.CP1
<220> FEATURE:
<221> NAME/KEY: misc_feature
<222> LOCATION: (13)..(13)
<223> OTHER INFORMATION: "n" stands for a, g, c or t

<400> SEQUENCE: 32
gatatcgaat tcntgcagcc cggggggatcc actagttcta gagcttggcg cctcccgctc     60
ctccgggtag ctcgtgggcc gccgccggcc ccggagcctt ttatcgaggc gggcgggagc    120
accgcccggc ccccaggaat gcggccccgg ccgtcgccat atttgggtgt gcgctctaaa    180
aataactccc ggcaggcagc aggtgttggc caacacctgc tgcctgccga caccaaatat    240
```

```
ggcgacgggg caggcagcag gtgttgggac acccaaatat ggcgacggcc gccaccgcgg    300
tggagctcgg tacctcccgg gttatgttag ctcagttaca gtaccataag atacattgat    360
gagtttggac aaaccacaac tagaatgcag tgaaaaaaat cgtttatttg tgaaatttgt    420
gatgctattg ctttatttgt aaccattata agctgcaata acaagttaa caacaacaat     480 tgcattcatt ttattttca                                                 499
```

```
<210> SEQ ID NO 33
<211> LENGTH: 600
<212> TYPE: DNA
<213> ORGANISM: Artificial Sequence
<220> FEATURE:
<223> OTHER INFORMATION: DNA SIS 4573-1g
<220> FEATURE:
<221> NAME/KEY: misc_feature
<222> LOCATION: (532)..(532)
<223> OTHER INFORMATION: "n" stands for a, g, c or t
<220> FEATURE:
<221> NAME/KEY: misc_feature
<222> LOCATION: (538)..(538)
<223> OTHER INFORMATION: "n" stands for a, g, c or t

<400> SEQUENCE: 33
acaacagtac cggaatgcca agcttgatat cgaattcctg cagcccgggg gatccactag    60
ttctagagct tggcgcctcc cgctcctccg ggtagctcgt gggccgccgc cggcccgga    120 gccttttatc gaggcgggcg ggagcaccgc ccggccccca ggaatgcggc cccggccgag   180
ggcggacacc aatatggcga cggggcaggc agcaggtgtt ggcgctctaa aaataactcc    240
cggcaggcag caggtgttgg cgctctaaaa ataactcccg gcaggcagca ggtgttggga    300
cacccaaata tggcgacggc cgccaccgcg gtggagctcg gtacctcccg ggttatgtta    360
gctcagttac agtaccataa gatacattga tgagtttgga caaaccacaa ctagaatgca    420
gtgaaaaaaa tgctttattt gtgaaatttg tgatgctatt gctttatttg taaccattat    480
aagctgcaat aaacaagtta acaacaacaa ttgcattcat tttatgtttc angttcangg    540
ggaagtgtgg gaagtttttt aaagcaagta aaactccacg taccttaata ttacttactt    600
```

```
<210> SEQ ID NO 34
<211> LENGTH: 478
<212> TYPE: DNA
<213> ORGANISM: Artificial Sequence
<220> FEATURE:
<223> OTHER INFORMATION: BCM3.CP1

<400> SEQUENCE: 34
gatatcgaat tcctgcagcc cggggatcc actagttcta gagcttggcg cctcccgctc     60
ctccgggtag ctcgtgggcc gccgccggcc ccggagcctt tatcgaggc gggcgggagc    120 accgccggc ccaggaat gcggcccgg ccgaggcgg acaccaatat ggcgacgggg        180
caggcagcag gtgttggcgc tctaaaaata actcccggca ggcagcaggt gttggcgctc    240 taaaataac tcccggcagg cagcaggtgt gggacacccc aaatatggcg acggccgcca    300
ccgcggtgga gctcggtacc tcccgggtta tgttagctca gttacagtac cataagatac    360
attgatgagt ttggacaaac cacaactaag aatgcagtga aaaaatgct ttatttgttg    420 aaatttgttg atgctattgc tttatttgtt aacccattat aagcttgcca ataaacaa    478
```

```
<210> SEQ ID NO 35
<211> LENGTH: 299
<212> TYPE: DNA
<213> ORGANISM: Artificial Sequence
```

```
<220> FEATURE:
<223> OTHER INFORMATION: DNA SIS 4573-2g
<220> FEATURE:
<221> NAME/KEY: misc_feature
<222> LOCATION: (57)..(57)
<223> OTHER INFORMATION: "n" stands for a, g, c or t
<220> FEATURE:
<221> NAME/KEY: misc_feature
<222> LOCATION: (262)..(262)
<223> OTHER INFORMATION: "n" stands for a, g, c or t
<220> FEATURE:
<221> NAME/KEY: misc_feature
<222> LOCATION: (280)..(280)
<223> OTHER INFORMATION: "n" stands for a, g, c or t
<220> FEATURE:
<221> NAME/KEY: misc_feature
<222> LOCATION: (282)..(282)
<223> OTHER INFORMATION: "n" stands for a, g, c or t
<220> FEATURE:
<221> NAME/KEY: misc_feature
<222> LOCATION: (289)..(289)
<223> OTHER INFORMATION: "n" stands for a, g, c or t
<220> FEATURE:
<221> NAME/KEY: misc_feature
<222> LOCATION: (298)..(298)
<223> OTHER INFORMATION: "n" stands for a, g, c or t

<400> SEQUENCE: 35
attttacaac agtactggaa tgccaagctt gatatcgaat tcctgcagcc cggggngtcc      60
actagttcta gagcttggcg cctcccgctc ctccgggtag ctcgtgggcc gccgccggcc     120
ccggagcctt ttatcgaggc gggcgggagc accgcccggc ccccaggaaa tgcggccccg     180
gccgtccgcc ctcggccgtc gccatatttg ggtgtcccaa cacctgctgc ctgcccacca     240
tcctcacggg agttattttt anagcgggga gttattttan ancggggant tattttana     299

<210> SEQ ID NO 36
<211> LENGTH: 502
<212> TYPE: DNA
<213> ORGANISM: Artificial Sequence
<220> FEATURE:
<223> OTHER INFORMATION: BCM4.CP1
<220> FEATURE:
<221> NAME/KEY: misc_feature
<222> LOCATION: (341)..(341)
<223> OTHER INFORMATION: "n" stands for a, g, c or t
<220> FEATURE:
<221> NAME/KEY: misc_feature
<222> LOCATION: (366)..(366)
<223> OTHER INFORMATION: "n" stands for a, g, c or t

<400> SEQUENCE: 36
gatatcgaat tcctgcagcc cggggatcc actagttcta gagcttggcg cctcccgctc       60
ctccgggtag ctcgtgggcc gccgccggcc ccggagcctt ttatcgaggc gggcgggagc     120
accgcccggc ccccaggaat gcggcccgg ccgtccgccc tcggccgtcg ccatatttgg     180
gtgtcccaac acctgctgcc tgcccaccat cctcacggga gttattttta gagcggggag     240
ttattttaga gcggggagtt attttagagc ggacacccaa atatgcgac ggccaacacc     300 tgtgcctgcc ccgagggcgg acggccgcca ccgcggtgga nctcggtacc tcccgggtta     360
tgttanctca gttacagtac cataagatac attgatgaat ttggacaaac cacaactaga     420
atgcagtgaa aaaatgctt tatttgttaa atttgtgatg ctattgcttt atttgttaac     480
cattataagc tgcaataaac aa                                             502

<210> SEQ ID NO 37
<211> LENGTH: 513
<212> TYPE: DNA
<213> ORGANISM: Artificial Sequence
```

```
<220> FEATURE:
<223> OTHER INFORMATION: "n" stands for a, g, c or t
<220> FEATURE:
<221> NAME/KEY: misc_feature
<222> LOCATION: (151)..(151)
<223> OTHER INFORMATION: "n" stands for a, g, c or t
<220> FEATURE:
<221> NAME/KEY: misc_feature
<222> LOCATION: (226)..(226)
<223> OTHER INFORMATION: "n" stands for a, g, c or t

<400> SEQUENCE: 37
aagcttgata tcgaattcct gcagcccggg ggatccacta gttctagagc ttggcgcctc      60
ccgctcctcc gggtagctcg tgggccgccg ccggccccgg agccttttat cgaggcgggc     120
gggagcaccg cccggcccc aggaatgcgg ncccggccgt ccgccctgct gcctgcgccg     180
tcgccatatt tgggtgtggg gagttatttt tagagcgggc aggcancagg tgttgggaca     240
cccaaatatg gcgacggccg ccaccgcggt ggagctcggt acctcccggg ttatgttagc     300
tcagttacag taccataaga tacattgatg agtttggaca aaccacaact agaatgcagt     360
gaaaaaaatg ctttatttgt gaaatttgtg atgctattgc tttatttgta accattataa     420
ctgcaataaa caattaaca acaacaattg cattcatttt atgtttcagg ttcaggggaa      480
gttttggaag ttttttaaacc aattaaaccc cac                                 513

<210> SEQ ID NO 38
<211> LENGTH: 480
<212> TYPE: DNA
<213> ORGANISM: Artificial Sequence
<220> FEATURE:
<223> OTHER INFORMATION: BCM6.CP1
<220> FEATURE:
<221> NAME/KEY: misc_feature
<222> LOCATION: (212)..(213)
<223> OTHER INFORMATION: "n" stands for a, g, c or t
<220> FEATURE:
<221> NAME/KEY: misc_feature
<222> LOCATION: (230)..(230)
<223> OTHER INFORMATION: "n" stands for a, g, c or t
<220> FEATURE:
<221> NAME/KEY: misc_feature
<222> LOCATION: (288)..(288)
<223> OTHER INFORMATION: "n" stands for a, g, c or t
<220> FEATURE:
<221> NAME/KEY: misc_feature
<222> LOCATION: (313)..(313)
<223> OTHER INFORMATION: "n" stands for a, g, c or t
<220> FEATURE:
<221> NAME/KEY: misc_feature
<222> LOCATION: (318)..(318)
<223> OTHER INFORMATION: "n" stands for a, g, c or t
<220> FEATURE:
<221> NAME/KEY: misc_feature
<222> LOCATION: (333)..(333)
<223> OTHER INFORMATION: "n" stands for a, g, c or t
<220> FEATURE:
<221> NAME/KEY: misc_feature
<222> LOCATION: (366)..(366)
<223> OTHER INFORMATION: "n" stands for a, g, c or t
<220> FEATURE:
<221> NAME/KEY: misc_feature
<222> LOCATION: (373)..(373)
<223> OTHER INFORMATION: "n" stands for a, g, c or t
<220> FEATURE:
<221> NAME/KEY: misc_feature
<222> LOCATION: (395)..(395)
<223> OTHER INFORMATION: "n" stands for a, g, c or t

<400> SEQUENCE: 38
aagcttgata tcgaattcct gcagcccggg ggatccacta gttctagagc ttggcgcctc      60
ccgctcctcc gggtagctcg tgggccgccg ccggccccgg agccttttat cgaggcgggc     120
```

```
gggagcaccg cccggccccc aggaaatgcg gccccggccg tcgccatatt tgggtgtcga      180
cacgcaaata tggcgacggc gctctaagaa tnnctcccgg caggcagcan gtgttggcac      240
cattcctcac gacacccaaa tatggcgacg gccgccaccg cggtgganct cggtacctcc      300
cgggttatgt tanctcantt acagtaccat aanatacatt gatgagtttg dacaaaccac      360
aactanaatg cantgaaaaa aatgctttat ttgtnaaatt tgttgatgct attgctttat      420
ttgtaaccat tataactgca ataaacaatt taacaacaac aattgcattc attttatgtt      480
```

<210> SEQ ID NO 39
<211> LENGTH: 261
<212> TYPE: DNA
<213> ORGANISM: Artificial Sequence
<220> FEATURE:
<223> OTHER INFORMATION: DNA SIS 4573-5g

<400> SEQUENCE: 39

```
agtaccggaa tgccaagctt gatatcgaat tcctgcagcc cggggggatcc actagttcta      60 gagcttggcg cctcccgctc ctccgggtag ctcgtgggcc gccgccggcc ccggagcctt      120
ttatcgaggc gggcgggagc accgcccggc ccccaggaat gcggcccccgg ccgtcgccat     180 atttgggtgt ccaccattcc tcaccgctct aaaaataact ccccgctcta aaaataactc      240
ccggcaggca gcaggtgttg g                                                261
```

<210> SEQ ID NO 40
<211> LENGTH: 244
<212> TYPE: DNA
<213> ORGANISM: Artificial Sequence
<220> FEATURE:
<223> OTHER INFORMATION: BCM7.CP1
<220> FEATURE:
<221> NAME/KEY: misc_feature
<222> LOCATION: (151)..(151)
<223> OTHER INFORMATION: "n" stands for a, g, c or t
<220> FEATURE:
<221> NAME/KEY: misc_feature
<222> LOCATION: (240)..(240)
<223> OTHER INFORMATION: "n" stands for a, g, c or t

<400> SEQUENCE: 40

```
aagcttgata tcgaattcct gcagcccggg ggatccacta gttctagagc ttggcgcctc      60
ccgctcctcc gggtagctcg tgggccgccg ccggccccgg agccttttat cgaggcgggc      120
gggagcaccg cccggccccc aggaaatgcg ncccggccgt cgccatattt gggtgtccac      180
cattcctcac cgctctaaaa ataactcccc gctctaaaaa taactcccgg caggcagcan      240
gtgt                                                                   244
```

<210> SEQ ID NO 41
<211> LENGTH: 500
<212> TYPE: DNA
<213> ORGANISM: Artificial Sequence
<220> FEATURE:
<223> OTHER INFORMATION: DNA SIS 4573-7g
<220> FEATURE:
<221> NAME/KEY: misc_feature
<222> LOCATION: (11)..(11)
<223> OTHER INFORMATION: "n" stands for a, g, c or t
<220> FEATURE:
<221> NAME/KEY: misc_feature
<222> LOCATION: (31)..(31)
<223> OTHER INFORMATION: "n" stands for a, g, c or t
<220> FEATURE:
<221> NAME/KEY: misc_feature
<222> LOCATION: (46)..(46)
<223> OTHER INFORMATION: "n" stands for a, g, c or t

```
<220> FEATURE:
<221> NAME/KEY: misc_feature
<222> LOCATION: (60)..(60)
<223> OTHER INFORMATION: "n" stands for a, g, c or t
<220> FEATURE:
<221> NAME/KEY: misc_feature
<222> LOCATION: (144)..(144)
<223> OTHER INFORMATION: "n" stands for a, g, c or t
<220> FEATURE:
<221> NAME/KEY: misc_feature
<222> LOCATION: (153)..(153)
<223> OTHER INFORMATION: "n" stands for a, g, c or t
<220> FEATURE:
<221> NAME/KEY: misc_feature
<222> LOCATION: (245)..(245)
<223> OTHER INFORMATION: "n" stands for a, g, c or t
<220> FEATURE:
<221> NAME/KEY: misc_feature
<222> LOCATION: (247)..(247)
<223> OTHER INFORMATION: "n" stands for a, g, c or t
<220> FEATURE:
<221> NAME/KEY: misc_feature
<222> LOCATION: (310)..(310)
<223> OTHER INFORMATION: "n" stands for a, g, c or t
<220> FEATURE:
<221> NAME/KEY: misc_feature
<222> LOCATION: (325)..(325)
<223> OTHER INFORMATION: "n" stands for a, g, c or t
<220> FEATURE:
<221> NAME/KEY: misc_feature
<222> LOCATION: (330)..(330)
<223> OTHER INFORMATION: "n" stands for a, g, c or t
<220> FEATURE:
<221> NAME/KEY: misc_feature
<222> LOCATION: (356)..(356)
<223> OTHER INFORMATION: "n" stands for a, g, c or t
<220> FEATURE:
<221> NAME/KEY: misc_feature
<222> LOCATION: (388)..(388)
<223> OTHER INFORMATION: "n" stands for a, g, c or t
<220> FEATURE:
<221> NAME/KEY: misc_feature
<222> LOCATION: (404)..(404)
<223> OTHER INFORMATION: "n" stands for a, g, c or t
<220> FEATURE:
<221> NAME/KEY: misc_feature
<222> LOCATION: (446)..(446)
<223> OTHER INFORMATION: "n" stands for a, g, c or t
<220> FEATURE:
<221> NAME/KEY: misc_feature
<222> LOCATION: (455)..(455)
<223> OTHER INFORMATION: "n" stands for a, g, c or t
<220> FEATURE:
<221> NAME/KEY: misc_feature
<222> LOCATION: (466)..(466)
<223> OTHER INFORMATION: "n" stands for a, g, c or t

<400> SEQUENCE: 41
acgagaatgc naagcttgat atcgaattcc ngcagcccgg gggatncact agttctacan      60
cttggcgcct cccgctcctc cgggtacctc gtgggccgcc gccggccccg gagccttta     120
tcgaggcggg cgggagcacc gccnggcccc cangaatgcg gccccggccg tcgccatatt    180
tgggtgtccc aacacctgct gcctgccccg tcgccatatt tgggtgtcgg gagttatttt    240
tagancngac acccaaatat ggcgacggcc gccaccgcgg tggagctcgg tacctcccgg    300
gttatgttan ctcagttaca gtacnataan atacattgat gactttggac aaaccncaac    360
taaaatgcag tgaaaaaaat gctttatntg tgaaatttgt gatnctattg ctttatttgt    420
aaccattata agctgcaata aacaanttaa caacnacaat ggcatncatt ttatgtatca    480
cgttcacggg gaggtgtggg                                                500

<210> SEQ ID NO 42
<211> LENGTH: 458
```

```
<212> TYPE: DNA
<213> ORGANISM: Artificial Sequence
<220> FEATURE:
<223> OTHER INFORMATION: BCM9.CP1

<400> SEQUENCE: 42
aagcttgata tcgaattcct gcagcccggg ggatccacta gttctagagc ttggcgcctc    60
ccgctcctcc gggtagctcg tgggccgccg ccggcccgg agccttttat cgaggcgggc    120
gggagcaccg cccggccccc aggaatgcgg ccccggccgt cgccatattt gggtgtccca    180
acacctgctg cctgccgcgt cgccatattt gggtgtcggg agttatttttt agagcggaca    240 cccaaatatg gcgacggccg ccaccgcggt ggagctcggt acctcccggg ttatgttagc    300
tcagttacag taccataaga tacattgatg agtttggaca aaccacaact agaatgcagt    360
gaaaaaaatg ctttatttgt gaaatttgtg atgctattgc tttatttgta accattataa    420
ctgcaataaa caatttaaca acaacaattg cattcatt                           458

<210> SEQ ID NO 43
<211> LENGTH: 335
<212> TYPE: DNA
<213> ORGANISM: Artificial Sequence
<220> FEATURE:
<223> OTHER INFORMATION: DNA SIS 4573-13g

<400> SEQUENCE: 43
attttacaac agtaccggaa tgccaagctt gatatcgaat tcctgcagcc cggggggatcc    60 actagttcta gagcttggcg cctcccgctc ctcgggtag ctcgtgggcc gccgccggcc    120
ccggagcctt ttatcgaggc gggcgggagc accgcccggc cccaggaat gcggccccgg    180 acgccatttc tctcctctaa aataactccc gtgaggaatg gtggacaccc aaatatggcg    240
acggggcagg cagcaggtgt tgggacaccc aaatatggcg acgggtgagg aatggtggac    300
acccaaatat ggcgacggga cacccaaata tttgg                              335

<210> SEQ ID NO 44
<211> LENGTH: 302
<212> TYPE: DNA
<213> ORGANISM: Artificial Sequence
<220> FEATURE:
<223> OTHER INFORMATION: BCM13.CP1

<400> SEQUENCE: 44
aagcttgata tcgacttcct gcagcccggg ggatccacta gttctagagc ttggcgcctc    60
ccgctcctcc gggtagctcg tgggccgccg ccggcccgg agccttttat cgaggcgggc    120
gggagcaccg cccggccccc aggaatgcgg ccccggacgc catttctctc ctctaaaata    180
actcccgtga ggaatggtgg acacccaaat atggcgacgg ggcaggcagc aggtgttggg    240
acacccaaat atggcgacgg gtgaggaatg gtggacaccc aaatatggcg acgggacacc    300
ca                                                                  302

<210> SEQ ID NO 45
<211> LENGTH: 549
<212> TYPE: DNA
<213> ORGANISM: Artificial Sequence
<220> FEATURE:
<223> OTHER INFORMATION: DNA SIS 4573-17g
<220> FEATURE:
<221> NAME/KEY: misc_feature
<222> LOCATION: (471)..(471)
<223> OTHER INFORMATION: "n" stands for a, g, c or t
<220> FEATURE:
<221> NAME/KEY: misc_feature
```

<222> LOCATION: (477)..(477)
<223> OTHER INFORMATION: "n" stands for a, g, c or t
<220> FEATURE:
<221> NAME/KEY: misc_feature
<222> LOCATION: (488)..(488)
<223> OTHER INFORMATION: "n" stands for a, g, c or t
<220> FEATURE:
<221> NAME/KEY: misc_feature
<222> LOCATION: (509)..(509)
<223> OTHER INFORMATION: "n" stands for a, g, c or t

<400> SEQUENCE: 45
attttacaac agtaccggaa tgccaagctt gatatcgaat tcctgcagcc cggggatcc      60 actagttcta gagcttggcg cctcccgctc ctccgggtag ctcgtgggcc gccgccggcc    120
ccggagcctt ttatcgaggc gggcgggagc accgcccggc ccccaggaat gcggccccgg    180
ccgtcgccat attgggtgtc ccaacacctg ctgcctcccg ctctaaaaat aactcccgac    240
acccaaatat ggcgacggcc gccaccgcgt ggagctcgg tacctccgg gttatgttag      300 ctcagttaca gtaccataag atacattgat gagtttggac aaaccacaac tagaatgcag    360
tgaaaaaaat gctttatttg tgaaatttgt gatgctattg ctttatttgt aaccattata    420
agctgcaata aacaagttaa caacaacaat tgcattcatt ttatgtttca ngttcanggg    480
gaagtgtngg aagttttta aaacaattna aactccacgt tactttaata ttacttactt    540
atcatggta                                                          549

<210> SEQ ID NO 46
<211> LENGTH: 210
<212> TYPE: DNA
<213> ORGANISM: Artificial Sequence
<220> FEATURE:
<223> OTHER INFORMATION: DNA SIS 4573-18g

<400> SEQUENCE: 46
attttacaac agtaccggaa tgccaagctt gatatcgaat tcctgcagcc cggggatcc      60 actagttcta gagcttggcg cctcccgctc ctccgggtag ctcgtgggcc gccgccggcc    120
ccggagcctt ttatcgaggc gggcgggagc accgcccggc ccccaggaat gcggccccgg    180
ccgagggcgg acggctccgc catatttggg                                    210

<210> SEQ ID NO 47
<211> LENGTH: 500
<212> TYPE: DNA
<213> ORGANISM: Artificial Sequence
<220> FEATURE:
<223> OTHER INFORMATION: DNA SIS 4573-19g
<220> FEATURE:
<221> NAME/KEY: misc_feature
<222> LOCATION: (260)..(260)
<223> OTHER INFORMATION: "n" stands for a, g, c or t
<220> FEATURE:
<221> NAME/KEY: misc_feature
<222> LOCATION: (303)..(303)
<223> OTHER INFORMATION: "n" stands for a, g, c or t
<220> FEATURE:
<221> NAME/KEY: misc_feature
<222> LOCATION: (328)..(328)
<223> OTHER INFORMATION: "n" stands for a, g, c or t
<220> FEATURE:
<221> NAME/KEY: misc_feature
<222> LOCATION: (361)..(361)
<223> OTHER INFORMATION: "n" stands for a, g, c or t
<220> FEATURE:
<221> NAME/KEY: misc_feature
<222> LOCATION: (381)..(381)
<223> OTHER INFORMATION: "n" stands for a, g, c or t
<220> FEATURE:
<221> NAME/KEY: misc_feature

```
<222> LOCATION: (439)..(439)
<223> OTHER INFORMATION: "n" stands for a, g, c or t
<220> FEATURE:
<221> NAME/KEY: misc_feature
<222> LOCATION: (464)..(464)
<223> OTHER INFORMATION: "n" stands for a, g, c or t
<220> FEATURE:
<221> NAME/KEY: misc_feature
<222> LOCATION: (499)..(499)
<223> OTHER INFORMATION: "n" stands for a, g, c or t

<400> SEQUENCE: 47
attttacaac agtaccggaa tgccaagctt gatatcgaat tcctgcagcc cggggaatc      60 cactagttct agagcttggc gcctcccgct cctccgggta gctcgtgggc cgccgccggc   120
cccggagcct tttatcgagg cgggcgggag caccgcccgg ccccaggaa tgcggcccg    180 gatggtgggc aggcagcagg tgttggcgct ctaaaaataa ctccccacca ttcctcacga   240
cacccaaata tggcgacggn accattcctc accgtccgc cctcggccgc caccgcggtg   300
ganctcggta cctcccgggt tatgttanct cagttacagt accataagat acattgatga   360
ntttggacaa accacaacta naatgcagtg aaaaaatgc tttatttgtg aaatttgtga    420
tgctattgct ttatttgtna ccattataag ctgcaataaa caanttaaca acaacaattg   480
cattcatttt atgtttcang                                                500

<210> SEQ ID NO 48
<211> LENGTH: 550
<212> TYPE: DNA
<213> ORGANISM: Artificial Sequence
<220> FEATURE:
<223> OTHER INFORMATION: DNA SIS 4573-20g
<220> FEATURE:
<221> NAME/KEY: misc_feature
<222> LOCATION: (483)..(483)
<223> OTHER INFORMATION: "n" stands for a, g, c or t
<220> FEATURE:
<221> NAME/KEY: misc_feature
<222> LOCATION: (517)..(517)
<223> OTHER INFORMATION: "n" stands for a, g, c or t
<220> FEATURE:
<221> NAME/KEY: misc_feature
<222> LOCATION: (523)..(523)
<223> OTHER INFORMATION: "n" stands for a, g, c or t
<220> FEATURE:
<221> NAME/KEY: misc_feature
<222> LOCATION: (533)..(533)
<223> OTHER INFORMATION: "n" stands for a, g, c or t

<400> SEQUENCE: 48
attttacaac agtaccggaa tgccaagctt gatatcgaat tcctgcagcc cggggatcc     60 actagttcta gagcttggcg cctcccgctc ctccgggtag ctcgtgggcc gccgccggcc   120
ccggagcctt ttatcgaggc gggcgggagc accgcccggc cccaggaat gcggcccgg    180 ccgtcgccat atttgggtgt ccaccattcc tcacccaaca cctgctgcct gccccaacac   240
ctgctgcctg ccgggagtta ttttagagc gccaacacct gctgcctgcc cgagggcgg    300 acggccgcca ccgcggtgga gctcggtacc tcccggggtta tgttagctca gttacagtac   360
cataagatac attgatgagt ttggacaaac cacaactaga atgcagtgaa aaaatgctt    420 tatttgttga aatttgtgat gctattgctt tatttgtaac cattataagc tgcaataaac   480
aanttaacaa caacaattgc attcatttta ttttcangtt canggaagt gtnggaagtt   540 ttttaaaacc                                                            550

<210> SEQ ID NO 49
<211> LENGTH: 550
```

```
<212> TYPE: DNA
<213> ORGANISM: Artificial Sequence
<220> FEATURE:
<223> OTHER INFORMATION: DNA SIS 4573-15g
<220> FEATURE:
<221> NAME/KEY: misc_feature
<222> LOCATION: (518)..(518)
<223> OTHER INFORMATION: "n" stands for a, g, c or t

<400> SEQUENCE: 49
attttacaac agtaccggaa tgccaagctt gatatcgaat tcctgcagcc cggggtatc     60 cactagttct agagcttggc gcctcccgct cctccgggta gctcgtgggc cgccgccggc   120
cccggagcct tttatcgagg cgggcgggag caccgcccgg ccccaggaa tgcggccccg    180 gccgtccgcc ctcggccgag ggggacggcg ctctaaaaat aactcccca acacctgctg    240 cctgccggca ggcagcaggt gttgggacac ccaaatatgg cgacggccgc caccgcggtg   300
gagctcggta cctcccgggt tatgttagct cagttacagt accataagat acattgatga   360
gtttggacaa accacaacta gaatgcagtg aaaaaaatgc tttatttgtt gaaatttgtg   420
atgctattgc tttatttgta accattataa gctgcaataa acaagttaac aacaacaatt   480
gcattcattt tatgtttcaa gttcaagggg aagttttngg aagttttta aaacaaatta    540 aaactccact                                                          550

<210> SEQ ID NO 50
<211> LENGTH: 400
<212> TYPE: DNA
<213> ORGANISM: Artificial Sequence
<220> FEATURE:
<223> OTHER INFORMATION: BCM15.CP1
<220> FEATURE:
<221> NAME/KEY: misc_feature
<222> LOCATION: (24)..(24)
<223> OTHER INFORMATION: "n" stands for a, g, c or t
<220> FEATURE:
<221> NAME/KEY: misc_feature
<222> LOCATION: (189)..(189)
<223> OTHER INFORMATION: "n" stands for a, g, c or t
<220> FEATURE:
<221> NAME/KEY: misc_feature
<222> LOCATION: (196)..(196)
<223> OTHER INFORMATION: "n" stands for a, g, c or t
<220> FEATURE:
<221> NAME/KEY: misc_feature
<222> LOCATION: (205)..(205)
<223> OTHER INFORMATION: "n" stands for a, g, c or t
<220> FEATURE:
<221> NAME/KEY: misc_feature
<222> LOCATION: (228)..(228)
<223> OTHER INFORMATION: "n" stands for a, g, c or t
<220> FEATURE:
<221> NAME/KEY: misc_feature
<222> LOCATION: (248)..(248)
<223> OTHER INFORMATION: "n" stands for a, g, c or t
<220> FEATURE:
<221> NAME/KEY: misc_feature
<222> LOCATION: (254)..(254)
<223> OTHER INFORMATION: "n" stands for a, g, c or t
<220> FEATURE:
<221> NAME/KEY: misc_feature
<222> LOCATION: (257)..(257)
<223> OTHER INFORMATION: "n" stands for a, g, c or t
<220> FEATURE:
<221> NAME/KEY: misc_feature
<222> LOCATION: (270)..(270)
<223> OTHER INFORMATION: "n" stands for a, g, c or t
<220> FEATURE:
<221> NAME/KEY: misc_feature
<222> LOCATION: (272)..(272)
<223> OTHER INFORMATION: "n" stands for a, g, c or t
<220> FEATURE:
<221> NAME/KEY: misc_feature
```

```
<222> LOCATION: (285)..(285)
<223> OTHER INFORMATION: "n" stands for a, g, c or t
<220> FEATURE:
<221> NAME/KEY: misc_feature
<222> LOCATION: (292)..(292)
<223> OTHER INFORMATION: "n" stands for a, g, c or t
<220> FEATURE:
<221> NAME/KEY: misc_feature
<222> LOCATION: (307)..(307)
<223> OTHER INFORMATION: "n" stands for a, g, c or t
<220> FEATURE:
<221> NAME/KEY: misc_feature
<222> LOCATION: (316)..(316)
<223> OTHER INFORMATION: "n" stands for a, g, c or t
<220> FEATURE:
<221> NAME/KEY: misc_feature
<222> LOCATION: (319)..(319)
<223> OTHER INFORMATION: "n" stands for a, g, c or t
<220> FEATURE:
<221> NAME/KEY: misc_feature
<222> LOCATION: (321)..(321)
<223> OTHER INFORMATION: "n" stands for a, g, c or t
<220> FEATURE:
<221> NAME/KEY: misc_feature
<222> LOCATION: (323)..(323)
<223> OTHER INFORMATION: "n" stands for a, g, c or t
<220> FEATURE:
<221> NAME/KEY: misc_feature
<222> LOCATION: (326)..(326)
<223> OTHER INFORMATION: "n" stands for a, g, c or t
<220> FEATURE:
<221> NAME/KEY: misc_feature
<222> LOCATION: (328)..(328)
<223> OTHER INFORMATION: "n" stands for a, g, c or t
<220> FEATURE:
<221> NAME/KEY: misc_feature
<222> LOCATION: (331)..(331)
<223> OTHER INFORMATION: "n" stands for a, g, c or t
<220> FEATURE:
<221> NAME/KEY: misc_feature
<222> LOCATION: (333)..(334)
<223> OTHER INFORMATION: "n" stands for a, g, c or t
<220> FEATURE:
<221> NAME/KEY: misc_feature
<222> LOCATION: (349)..(349)
<223> OTHER INFORMATION: "n" stands for a, g, c or t
<220> FEATURE:
<221> NAME/KEY: misc_feature
<222> LOCATION: (351)..(351)
<223> OTHER INFORMATION: "n" stands for a, g, c or t
<220> FEATURE:
<221> NAME/KEY: misc_feature
<222> LOCATION: (360)..(360)
<223> OTHER INFORMATION: "n" stands for a, g, c or t
<220> FEATURE:
<221> NAME/KEY: misc_feature
<222> LOCATION: (362)..(362)
<223> OTHER INFORMATION: "n" stands for a, g, c or t
<220> FEATURE:
<221> NAME/KEY: misc_feature
<222> LOCATION: (365)..(365)
<223> OTHER INFORMATION: "n" stands for a, g, c or t
<220> FEATURE:
<221> NAME/KEY: misc_feature
<222> LOCATION: (374)..(374)
<223> OTHER INFORMATION: "n" stands for a, g, c or t
<220> FEATURE:
<221> NAME/KEY: misc_feature
<222> LOCATION: (376)..(376)
<223> OTHER INFORMATION: "n" stands for a, g, c or t
<220> FEATURE:
<221> NAME/KEY: misc_feature
<222> LOCATION: (399)..(399)
<223> OTHER INFORMATION: "n" stands for a, g, c or t

<400> SEQUENCE: 50
aagcttgata tcgacctcct gcancccggg ggatccacta gttctagagc ttggcgcctc    60
ccgctcctcc gggtagctcg tgggccgccg ccggccccgg agccttttat cgaggcgggc   120
```

```
gggagcaccg cccggccccc aggaatgcgg ccccggccgt ccgccctcgg ccgagggga      180 acgggctcna aaaatnactc ccccnacacc tgctgcctgc cggcaagnaa caagttttgg      240
gaaacccnaa tatngcnaac ggcgccaccn cngtggaact ccgtncctcc cnggttatgt      300
taactcnatt accgtnccnt nanaancntt nannaatttg gaacaaccnc nactaaaatn      360
cnatnaaaaa aatncnttat ttgttaaatt tgttaagcna                           400
```

<210> SEQ ID NO 51
<211> LENGTH: 500
<212> TYPE: DNA
<213> ORGANISM: Artificial Sequence
<220> FEATURE:
<223> OTHER INFORMATION: DNA SIS 4585-2g
<220> FEATURE:
<221> NAME/KEY: misc_feature
<222> LOCATION: (495)..(495)
<223> OTHER INFORMATION: "n" stands for a, g, c or t

<400> SEQUENCE: 51

```
attttacaac agtaccggaa tgccaagctt gatatcgaat tcctgcagcc cggggatcc       60 actagttcta gagcttggcg cctcccgctc ctccgggtag ctcgtgggcc gccgccggcc     120
ccggagcctt ttatcgaggc gggcgggagc accgcccggc ccccaggaat gcggccccgg     180
ccgtcgccat atttggtgtc gggagttatt tttagagcgg acacccaaat atggcgacgg     240
ggcaggcagc aggtgttggg acacccaaat atggcgacgg ccgccaccgc ggtggagctc     300
ggtacctccc gggttatgtt agctcagtta cagtaccata agatacattg atgagtttgg     360
acaaaccaca actagaaatg cagttgaaaa aaatgcttta tttgttgaaa tttgttgatg     420
ctattgcttt atttgttaac ccattataag cctgcaataa acaatttaac aacaacaatt     480
gcattccatt ttatntttcc                                                500
```

<210> SEQ ID NO 52
<211> LENGTH: 239
<212> TYPE: DNA
<213> ORGANISM: Artificial Sequence
<220> FEATURE:
<223> OTHER INFORMATION: DNA SIS 4573-21g

<400> SEQUENCE: 52

```
attttacaac agtaccggaa tgccaagctt gatatcgaat tcctgcagcc cggggatcc       60 actagttcta gagcttggcg cctcccgctc ctccgggtag ctcgtgggcc gccgccggcc     120
ccggagcctt ttatcgaggc gggcgggagc accgcccggc ccccaggaat gcggccccgg     180
ccgtcgccat atttgggtgt cgggagttat ttttagaggt gaggaatggt gccgtccgc     239
```

<210> SEQ ID NO 53
<211> LENGTH: 500
<212> TYPE: DNA
<213> ORGANISM: Artificial Sequence
<220> FEATURE:
<223> OTHER INFORMATION: DNA SIS 4573-22g
<220> FEATURE:
<221> NAME/KEY: misc_feature
<222> LOCATION: (357)..(357)
<223> OTHER INFORMATION: "n" stands for a, g, c or t
<220> FEATURE:
<221> NAME/KEY: misc_feature
<222> LOCATION: (475)..(475)
<223> OTHER INFORMATION: "n" stands for a, g, c or t
<220> FEATURE:
<221> NAME/KEY: misc_feature
<222> LOCATION: (493)..(493)
<223> OTHER INFORMATION: "n" stands for a, g, c or t

<400> SEQUENCE: 53

```
attttacaac agtaccggaa tgccaagctt gatatcgaat tcctgcagcc cgggggatcc      60
actagttcta gagcttggcg cctcccgctc ctccgggtag ctcgtgggcc gccgccggcc     120
ccggagcctt ttatcgaggc gggcgggagc accgcccggc cccaggaatg cggccccgg     180
ccgtcgccat atttgggtgt cccgtcgcca tatttgggtg tcgggagtta ttttagagc     240
ggacacccaa atatggcgac ggccgccacc gcggtggagc tcggtacctc ccgggttatg    300
ttagctcagt tacagtacca taagatacat tgatgagttt ggacaaacca caactanaat    360
gcagtgaaaa aaatgcttta tttgtgaaat ttgtgatgct attgctttat ttgtaaccat   420
tataagctgc aataaacaag ttaacaacaa caattgcatt cattttatgt ttcangttca    480
aggggaagtg ttngaagttt                                                500
```

<210> SEQ ID NO 54
<211> LENGTH: 550
<212> TYPE: DNA
<213> ORGANISM: DNA SIS 4573-23g
<220> FEATURE:
<221> NAME/KEY: misc_feature
<222> LOCATION: (527)..(527)
<223> OTHER INFORMATION: "n" stands for a, g, c or t

<400> SEQUENCE: 54

```
attttacaac agtacggaat gccaagcttg atatcgaatt cctgcagccc ggggatcca      60
ctagttctag agcttggcgc ctcccgctcc tccgggtagc tcgtgggccg ccgccggccc    120
cggagccttt tatcgaggcg ggcgggagca ccgcccggcc cccaggaatg cggccccggc    180
cgtcgccata tttggtgtcg acacccaaat atggcgacgg gcaggcagc aggtgttggg     240
acacccaaat atggcgacgg gtgaggaatg gtggggagtt attttagag cggacaccca     300
aatatggcga cggccgccac cgcggtggag ctcggtacct cccgggttat gttagctcag    360
ttacagtacc ataagataca ttgatgagtt tggacaaacc acaactagaa tgcagtgaaa    420
aaaatgcttt atttgttgaa atttgtgatg ctattgcttt atttgtaacc attataagct    480
gcaataaaca atttaacaac aacaattgca ttcattttat gtttcangtt ccaggggaag    540
tttttggaag                                                           550
```

<210> SEQ ID NO 55
<211> LENGTH: 300
<212> TYPE: DNA
<213> ORGANISM: Artificial Sequence
<220> FEATURE:
<223> OTHER INFORMATION: C1-28 sequence: (pIF1719)
<220> FEATURE:
<221> NAME/KEY: mutation
<222> LOCATION: (75)..(77)
<223> OTHER INFORMATION: Instead of TGT: sequence is GTG

<400> SEQUENCE: 55

```
tcgccatatt tgggtgtcgg agttatttt agagcgggca ggcagcaggt gttggggag      60
ttatttttag agcggtgagg aatggtgcac cattcctcac gacacccaaa tatggcgacg    120
gcgctctaaa aataactccc gggagttatt tttagagcgg tgaggaatgg tggacaccca    180
aatatggcga cggaaatatg gcgacggcac cattcctcac gacacccaaa tatggcgacg    240
gggcaggcag caggtgttgg caccattcct caccgctcta aaataactcc cgagggcgga    300
```

<210> SEQ ID NO 56
<211> LENGTH: 207

```
<212> TYPE: DNA
<213> ORGANISM: Artificial Sequence
<220> FEATURE:
<223> OTHER INFORMATION: C5-12 Sequence: pIF1720
<220> FEATURE:
<221> NAME/KEY: mutation
<222> LOCATION: (112)..(112)
<223> OTHER INFORMATION: C instead of T

<400> SEQUENCE: 56
cttcggcacc atcctcacga cacccaaata tggcgacggg tgaggaatgg tggggagtta      60
tttttagagc ggtgaggaag gtgggcaggc agcaggtgtt ggcgctctaa aaataactcc     120
cgggagttat ttttagagcg gaggaatggt ggacacccaa atatggcgac ggttcctcac     180
ccgtcgccat atttgggtgt ccgccct                                         207
```